United States Patent
Elich et al.

(10) Patent No.: US 9,447,423 B2
(45) Date of Patent: Sep. 20, 2016

(54) REGULATORY POLYNUCLEOTIDES AND USES THEREOF

(75) Inventors: Tedd D. Elich, Durham, NC (US); Philip N. Benfey, Chapel Hill, NC (US); Jee W. Jung, Raleigh, NC (US)

(73) Assignee: Monsanto Technology LLC, St. Louis, MO (US)

( * ) Notice: Subject to any disclaimer, the term of this patent is extended or adjusted under 35 U.S.C. 154(b) by 593 days.

(21) Appl. No.: 13/808,510

(22) PCT Filed: Jul. 7, 2011

(86) PCT No.: PCT/US2011/043197
§ 371 (c)(1),
(2), (4) Date: Jan. 4, 2013

(87) PCT Pub. No.: WO2012/006426
PCT Pub. Date: Jan. 12, 2012

(65) Prior Publication Data
US 2013/0117883 A1    May 9, 2013

Related U.S. Application Data

(60) Provisional application No. 61/362,959, filed on Jul. 9, 2010.

(51) Int. Cl.
*C12N 15/82* (2006.01)
*C12N 15/113* (2010.01)
*C12N 15/63* (2006.01)
*C07H 21/00* (2006.01)

(52) U.S. Cl.
CPC ............ *C12N 15/8216* (2013.01); *C07H 21/00* (2013.01); *C12N 15/113* (2013.01); *C12N 15/63* (2013.01); *C12N 15/82* (2013.01); *C12N 15/8201* (2013.01); *C12N 15/8241* (2013.01)

(58) Field of Classification Search
CPC .................................................. C12N 230/50
See application file for complete search history.

(56) References Cited

U.S. PATENT DOCUMENTS

| | | | |
|---|---|---|---|
| 2008/0141585 A1 | 6/2008 | Benfey et al. | |
| 2009/0249512 A1 | 10/2009 | Broekaert et al. | |
| 2010/0107283 A1* | 4/2010 | Dasgupta et al. | 800/300 |

FOREIGN PATENT DOCUMENTS

| | | | |
|---|---|---|---|
| WO | WO01/98480 A2 | 12/2001 | |
| WO | WO 01/98480 A2 * | 12/2001 | C12N 15/00 |

OTHER PUBLICATIONS

Kim et al. 1994. A 20 nucleotide upstream element is esential for the nopaline synthase (nos) promoter activity. Plant Molecular Biology, 24:105-117.*
Rombauts et al. 2003. Computational approaches to identify promoters and cis-regulatory elements in plant genomes. Plant Physiology. 132:1162- 1176).*
Higo et al. 1998. PLACE: A database of plant cis-acting regulatory DNA elements. Nucl Acids Res. 26: 358-359.*
Brady et al., "A High-Resolution Root Spatiotemporal Map Reveals Dominant Expresson Patterns," *Science*, 318:801-806 (2007).
AtGeneExpress Expression Atlas of Arabidopsis Thaliana (Laubinger, Schmid, Weigel), available on the World Wide Web at weigelworld.org/resources/microarray/AtGenExpress, printed Jul. 25, 2012.
Schmid et al., "A Gene Expression Map of Arabidopsis Thaliana Development," *Nat. Genet.*, 37(5):501-506 (2005).
Development and Abiotic Stress datasets, http://www.weigelworld.org/resources/microarray/AtGenExpress, web resource, too long to print.
TAIR database, http://www.arabidopsis.org/, printed Feb. 28, 2013.
Kilian et al., "The AtGenExpress Global Stress Expression Data Set: Protocols, Evaluation and Model Data Analysis of UV-B Light, Drought and Cold Stress Responses," *Plant J.*, 50:347-363 (2007).
Lee et al., "Transcriptional and Posttranscriptional Regulation of Transcription Factor Expression in Arabidopsis Roots," *Proc Natl Acad Sci U S A*, 103(15):6055-6060 (2006).
Clough and Bent, "Floral Dip: A Simplified Method for Agrobacterium-Mediated Transformation of Arabidopsis Thaliana," *Plant J*, 16(6), 735-743 (1998).
Moreno-Hagelsieb and Latimer, "Choosing BLAST Options for Better Detection of Orthologs as Reciprocal Best Hits," *Bioinformatics*, 24(3):319-324 (2008).
International Search Report and Written Opinion received in PCT Application No. PCT/US11/43197 dated Feb. 14, 2012.
EMBL database entry ACO27134.4, http://www.ebi.ac.uk/ena/data/view/ACO27134, retrieved Jan. 14, 2012.
EMBL database entry ALO35709.1, http://www.ebi.ac.uk/ena/data/view/AL035709, retrieved Jan. 16, 2012.

* cited by examiner

Primary Examiner — Anne Kubelik
Assistant Examiner — Karen Redden
(74) *Attorney, Agent, or Firm* — Dentons US LLP; Carine M. Doyle, Esq.

(57) ABSTRACT

The present disclosure provides compositions and methods for regulating expression of transcribable polynucleotides in plant cells, plant tissues, and plants. Compositions include regulatory polynucleotide molecules capable of providing expression in plant tissues and plants. Methods for expressing polynucleotides in a plant cell, plant tissue, or plants using the regulatory polynucleotide molecules disclosed herein are also provided.

20 Claims, 37 Drawing Sheets

Figure 1  (SEQ ID NO: 1) AT1G13440, +first intron
gttttataaccattcacctaacaaaaatgaaatggaaaaagaaaagagagcaaataagaggaggagaagaagaag
acttttggcaaaagccaagagtcatacctattagtctattacataaggtgtgatgttttttttttgctgtcacatt
ccatctgacctaccaaagctctcaaagtggagcatctattgtgtcttggtatagagtcacgattagataaatata
caacaccatatgtacttgtgtcaaattataaatatttgaaacagtaagcaaccagtaattcgataaagacgtcta
caagcatctacacatctaaattgattaaaacaaaacacctttaaatatagtgtttatgaagtcaaatcttcacct
tgattattctaaaacaatggttggagtaatgttgctgaatgttgagtgagaattgacatttgagagtaactttca
ctataatgaactggatgataaagttgatccgataataattgaatttaccatgaatggtatcacaagatacatgta
tagaagacagtggtgttacttgttacgcaaaattaaaaaatgagcatactattgcagttactttggatttattaa
ggaaaattatggtttgacaacaacaataatacaaaatcttatgaaaattaaataaaaagaaaaacaaatttggct
attggcaaagctcattggctgtcaaaggaatatatacaaaatctgctacgttgcagtcttgcgtgcaccggccc
agcccataggattagagtattaaacctcgaatattccatcagcctgcgcgtgaatccaagcgccattagtttccc
caaatcagttcttaatcctacccataaacgatgggtaaaaatggtaaataagaaagaaagtaaagtacaatatag
taatattaattagtgaatctaatctattagccttttttcccaagaaaaaatctcaGccactcgatcatattttcaa
ttttcatcatcacgttcttcttctcttttaaataaccctaaatcctcaccaaacccaaaccctcactcactattt
tcacattctcttctctctcgatatcatctaaatctctctcgatctcaatttcgcaaacaggtaagcttctcgctc
ttgttgatctgcgattcttcgatttattgttctttcgttgatacttttgaatctgatcgtaattttggtttgtg
taggt

Figure 2  (SEQ ID NO: 2) AT1G13440
gttttataaccattcacctaacaaaaatgaaatggaaaaagaaaagagagcaaataagaggaggagaagaagaag
acttttggcaaaagccaagagtcatacctattagtctattacataaggtgtgatgttttttttttgctgtcacatt
ccatctgacctaccaaagctctcaaagtggagcatctattgtgtcttggtatagagtcacgattagataaatata
caacaccatatgtacttgtgtcaaattataaatatttgaaacagtaagcaaccagtaattcgataaagacgtcta
caagcatctacacatctaaattgattaaaacaaaacacctttaaatatagtgtttatgaagtcaaatcttcacct
tgattattctaaaacaatggttggagtaatgttgctgaatgttgagtgagaattgacatttgagagtaactttca
ctataatgaactggatgataaagttgatccgataataattgaatttaccatgaatggtatcacaagatacatgta
tagaagacagtggtgttacttgttacgcaaaattaaaaaatgagcatactattgcagttactttggatttattaa
ggaaaattatggtttgacaacaacaataatacaaaatcttatgaaaattaaataaaaagaaaaacaaatttggct
attggcaaagctcattggctgtcaaaggaatatatacaaaatctgctacgttgcagtcttgcgtgcaccggccc
agcccataggattagagtattaaacctcgaatattccatcagcctgcgcgtgaatccaagcgccattagtttccc
caaatcagttcttaatcctacccataaacgatgggtaaaaatggtaaataagaaagaaagtaaagtacaatatag
taatattaattagtgaatctaatctattagccttttttcccaagaaaaaatctcaGccactcgatcatattttcaa
ttttcatcatcacgttcttcttctcttttaaataaccctaaatcctcaccaaacccaaaccctcactcactattt
tcacattctcttctctctcgatatcatctaaatctctctcgatctcaatttcgcaaa Figure 3  (SEQ ID NO: 3) AT1G22840, +first intron
ttatatacaacaagttttaattgcatgatttcctgtaaacataagtttacatgaactaggggatggtccttcgca
agtatgagtaacaagcataaacagcattatatatgaaataaatatgagcccacctaaacccattaagggcccatt
aagattggagatactgcttttttaagagaggtcactttttccacaGtgaaaccctaaggaaacttcggcaagctc
cagagaaacgagagttccgtaatcattttctcttgttgttcctgatcgcgtagctcaagcgaaaaaacaggtttt
cactcatcgatctctctcactcttgaattctatttctatggttgattttcgcaatttatctgaattttatcggg
cctttgttttacatcgctttataatcgatttgttcatgttaatcaaaaatctctgatgtgatctggttaacggat
tcttcgattagatcatagatctgatccaataacctcgatgtcttactcgtgtttatccttaaatcttcagctcaa
tgcatgtgacgaatttctgaggttttttatatacaacttttcgcattttgtggaacttgattctcgaattctaag
taatgatacaacaatgatttgagctagtttgcgtcacagattctcattttttcttgaaattgcgtgaaattagaaa
acactgttgctcaatggtttctattgttttcgtagcttttgtagaatgtgatttgcgtcacattgttgctcaaca
cttgaccttgttgttttaatataggt

Figure 4  (SEQ ID NO: 4) AT1G22840
ttatatacaacaagttttaattgcatgatttcctgtaaacataagtttacatgaactaggggatggtccttcgca
agtatgagtaacaagcataaacagcattatatatgaaataaatatgagcccacctaaacccattaagggcccatt
aagattggagatactgcttttttaagagaggtcactttttccacaGtgaaaccctaaggaaacttcggcaagctc
cagagaaacgagagttccgtaatcattttctcttgttgttcctgatcgcgtagctcaagcgaaaaaa Figure 5 (SEQ ID NO: 5) AT1G22840, +first intron, +35S minimal promoter
ttatatacaacaagttttaattgcatgatttcctgtaaacataagtttacatgaactaggggatggtccttcgca
agtatgagtaacaagcataaacagcattatatatgaaataaatatgagcccacctaaacccattaagggcccatg
caagacccttcctctatataaggaagttcatttcatttggagagggGtgaaaccctaaggaaacttcggcaagctc
cagagaaacgagagttccgtaatcattttctcttgttgttcctgatcgcgtagctcaagcgaaaaaacaggtttt
cactcatcgatctctctcactcttgaattctatttctatggttgattttcgcaatttatctgaattttatcggg
cctttgttttacatcgctttataatcgatttgttcatgttaatcaaaaatctctgatgtgatctggttaacggat
tcttcgattagatcatagatctgatccaataacctcgatgtcttactcgtgtttatccttaaatcttcagctcaa
tgcatgtgacgaatttctgaggttttatatacaacttttcgcattttgtggaacttgattctcgaattctaag
taatgatacaacaatgatttgagctagttgcgtcacagattctcatttttcttgaaattgcgtgaaattagaaa
acactgttgctcaatggtttctattgttttcgtagcttttgtagaatgtgatttgcgtcacattgttgctcaaca
cttgaccttgttgttttaatataggt Figure 6 (SEQ ID NO: 6) AT1G52300, +first intron
cgacacataaaaattaaaacaaatcaaaaacaaacaattgatcaaattcttaagaaataaaaaaggtgaataaca
tacatgtagacttttatcacaccaaaaaaaacacacacacatgtagagaattttttgtggtatttttgtcttgtcct
cctaaaatcatatgctatgtgaaagtataacatcgacttgaatattagaaaattgggaaactcaaacaactagta
tataaaatattttgtatgtgaaccattgttctacttacatgttgtgattgtaaaatttatggaggcaaagagaga
aaaatgtaccatgaacgaggaatgatggattaatggttccttgacttgagaagaaggtttatgactctatcgtgt
ccaaaatcaaaacttctcttgacgatctcttgggagcttcttttgagactcaaagatatattaaaggaaaataca
agctgaaaaaaagtaaaaatcaaaatccctgtaatcgacgaccaaaaaaaaagatttattgatacttacttgga
ggaaaaaaccaacatttatggaataaaattgttccccaagtattcaattaatacttcagttgtgaaaatttgagac
tcaaatcacaaatttcttaatatatttttttttttatcatccgatttaatctgaggaatgttgtttacataaa
tgataggaaacggtttagtgcaaaattttctcaatataattgttattgcaattagtttttttattttttatttt
tatttttggtttaaaagttaaaacaacacaatttaataaagtataaaatataatactcacctaaattattgttac
aaattctattgtaaaccggcacaacaatggtaaaaagtaaaaacaaatcgtttcctggttaagtcttcgaaatga
gtcccgcacaaaaaggcttattaagtattaaggcccatgggcctgacttatcgatccaataaagaattcacaacc
ctaataaaaaggacgaaaccctagctttatataaacttttgTtaacctaccgtcgtcacttccttctcttgaagc
cggaaaccttaaggttttatatctgggaaaaaactcgcatccgcttcaggtgatctacgattctcctctctatct
ttctatttcatctctatgcttcgttgatttcattactctgatatctgttttatcgctttgttttttgagattctca
ggt Figure 7 (SEQ ID NO: 7) AT1G52300
cgacacataaaaattaaaacaaatcaaaaacaaacaattgatcaaattcttaagaaataaaaaaggtgaataaca
tacatgtagacttttatcacaccaaaaaaaacacacacacatgtagagaattttttgtggtatttttgtcttgtcct
cctaaaatcatatgctatgtgaaagtataacatcgacttgaatattagaaaattgggaaactcaaacaactagta
tataaaatattttgtatgtgaaccattgttctacttacatgttgtgattgtaaaatttatggaggcaaagagaga
aaaatgtaccatgaacgaggaatgatggattaatggttccttgacttgagaagaaggtttatgactctatcgtgt
ccaaaatcaaaacttctcttgacgatctcttgggagcttcttttgagactcaaagatatattaaaggaaaataca
agctgaaaaaaagtaaaaatcaaaatccctgtaatcgacgaccaaaaaaaaagatttattgatacttacttgga
ggaaaaaaccaacatttatggaataaaattgttccccaagtattcaattaatacttcagttgtgaaaatttgagac
tcaaatcacaaatttcttaatatatttttttttttatcatccgatttaatctgaggaatgttgtttacataaa
tgataggaaacggtttagtgcaaaattttctcaatataattgttattgcaattagtttttttattttttatttt
tatttttggtttaaaagttaaaacaacacaatttaataaagtataaaatataatactcacctaaattattgttac
aaattctattgtaaaccggcacaacaatggtaaaaagtaaaaacaaatcgtttcctggttaagtcttcgaaatga
gtcccgcacaaaaaggcttattaagtattaaggcccatgggcctgacttatcgatccaataaagaattcacaacc
ctaataaaaaggacgaaaccctagctttatataaacttttgTtaacctaccgtcgtcacttccttctcttgaagc
cggaaaccttaaggttttatatctgggaaaaaactcgcatccgcttca Figure 8 (SEQ ID NO: 8) AT1G52300, +first intron, +35S minimal promoter
cgacacataaaaattaaaacaaatcaaaaacaaacaattgatcaaattcttaagaaataaaaaaggtgaataaca
tacatgtagacttttatcacaccaaaaaaaacacacacacatgtagagaattttttgtggtatttttgtcttgtcct
cctaaaatcatatgctatgtgaaagtataacatcgacttgaatattagaaaattgggaaactcaaacaactagta
tataaaatattttgtatgtgaaccattgttctacttacatgttgtgattgtaaaatttatggaggcaaagagaga
aaaatgtaccatgaacgaggaatgatggattaatggttccttgacttgagaagaaggtttatgactctatcgtgt
ccaaaatcaaaacttctcttgacgatctcttgggagcttcttttgagactcaaagatatattaaaggaaaataca agctgaaaaaaagtaaaaatcaaaatccctgtaatcgacgaccaaaaaaaaagatttattgatacttacttgga
ggaaaaaaccaacatttatggaataaattgttccccaagtattcaattaatacttcagttgtgaaaatttgagac
tcaaatcacaaattttcttaatatatttttttttatcatccgattttaatctgaggaatgttgtttacataaa
tgataggaaacggtttagtgcaaaattttctcaatataattgttattgcaattagtttttttattttttattttt
tattttggttaaaagttaaaacaacacaatttaataaagtataaaatataatactcacctaaattattgttac
aaattctattgtaaaccggcacaacaatggtaaaagtaaaaacaaatcgtttcctggttaagtcttcgaaatga
gtcccgcacaaaaaggcttattaagtattaaggcccatgggcctgacttatcgatccaataaagaattcagcaag
acccttcctctatataaggaagttcatttcatttggagaggTtaacctaccgtcgtcacttccttctcttgaagc
cggaaaccttaaggttttatatctgggaaaaaactcgcatccgcttcaggtgatctacgattctcctctctatct
ttctatttcatctctatgcttcgttgatttcattactctgatatctgttttatcgctttgttttgagattctca
ggt Figure 9 (SEQ ID NO: 9) AT4G37830, +first intron
tgcgagtgggcgaattccggagcactctgattggctgaaaaaatagaaatagtagtgatgttgctcctcctctcc
tcctctattattaattttttcgtcgttcttcttctgaaagttgtgtggttttttagaggtcaccaaaaaaaatctat
tttgagatactaaaaatatttcgttttgcattttgttgtgcagccatttgttacacaggttga
agcttataactgaaaattggattcaaagaatcgtagatgaagaaatcgaagtgagttgaatattttctgaacata
tgaaaattggaacaagtttttctcatttgctagtttcctgtttttatgttttcttgactttaggagatgacat
atggaggtgaactatacaaaggttgttgcaacgataacattctccttaattcagttttgcaactcggttacaag
cactcagtggacttttggccaagacaattttttttttttttctctctctctaaaatgttatagatacgaatcct
ttgttgaataaaggaaaaagttgaacatttgattacacataagactttaacataatccaactttttttttatatga
agctacaaacaagatttaaaacatcaaagattccatctaaacttcattcatcttcaatcttcaacatccttcaat
gactagtatgtatgtacataagtaaaattgttgataagaaaacaaaacaatgatgggctaaaatagcccataaaa
ggcccattaaacttgggtttagactttagattcaacgacgccagattAgtgagtcacataaccctcttggaaaga
gtctcaacacttgcagagaaaaagaacaaggaagatcccggaaacaggtaatttctctcctctctattttttacca
ttttccattgacgacgatctaggttttctgatttgattttggagaacgcctcgatgagtttatagattcgtagat
tggttttgagattcagtataatttcacccggattccaattttttgaaccgatacctaattttgaattgatttggta
gatcgattggtcaaatttgaaattgattttttctccataatatctgaagcgtcttattggatcaaatctacaacat
ttctctgttgaaaggatcgatttttttttttcttggaacatgataacttttgattattcatcaaagtttttgttctt
tttaatatttcacaggt Figure 10 (SEQ ID NO: 10) AT4G37830
tgcgagtgggcgaattccggagcactctgattggctgaaaaaatagaaatagtagtgatgttgctcctcctctcc
tcctctattattaattttttcgtcgttcttcttctgaaagttgtgtggttttttagaggtcaccaaaaaaaatctat
tttgagatactaaaaatatttcgttttgcattttgttgtgcagccatttgttacacaggttga
agcttataactgaaaattggattcaaagaatcgtagatgaagaaatcgaagtgagttgaatattttctgaacata
tgaaaattggaacaagtttttctcatttgctagtttcctgtttttatgttttcttgactttaggagatgacat
atggaggtgaactatacaaaggttgttgcaacgataacattctccttaattcagttttgcaactcggttacaag
cactcagtggacttttggccaagacaattttttttttttttctctctctctaaaatgttatagatacgaatcct
ttgttgaataaaggaaaaagttgaacatttgattacacataagactttaacataatccaactttttttttatatga
agctacaaacaagatttaaaacatcaaagattccatctaaacttcattcatcttcaatcttcaacatccttcaat
gactagtatgtatgtacataagtaaaattgttgataagaaaacaaaacaatgatgggctaaaatagcccataaaa
ggcccattaaacttgggtttagactttagattcaacgacgccagattAgtgagtcacataaccctcttggaaaga
gtctcaacacttgcagagaaaaagaacaaggaagatcccggaaa Figure 11 (SEQ ID NO: 11) AT4G37830, +first intron, +35S minimal promoter
tgcgagtgggcgaattccggagcactctgattggctgaaaaaatagaaatagtagtgatgttgctcctcctctcc
tcctctattattaattttttcgtcgttcttcttctgaaagttgtgtggttttttagaggtcaccaaaaaaaatctat
tttgagatactaaaaatatttcgttttgcattttgttgtgcagccatttgttacacaggttga
agcttataactgaaaattggattcaaagaatcgtagatgaagaaatcgaagtgagttgaatattttctgaacata
tgaaaattggaacaagtttttctcatttgctagtttcctgtttttatgttttcttgactttaggagatgacat
atggaggtgaactatacaaaggttgttgcaacgataacattctccttaattcagttttgcaactcggttacaag
cactcagtggacttttggccaagacaattttttttttttttctctctctctaaaatgttatagatacgaatcct
ttgttgaataaaggaaaaagttgaacatttgattacacataagactttaacataatccaactttttttttatatga
agctacaaacaagatttaaaacatcaaagattccatctaaacttcattcatcttcaatcttcaacatccttcaat
gactagtatgtatgtacataagtaaaattgttgataagaaaacaaaacaatgatgggctaaaatagcccataaaa
ggcaagacccttcctctatataaggaagttcatttcatttggagaggAgtgagtcacataaccctcttggaaaga gtctcaacacttgcagagaaaaagaacaaggaagatcccggaaacaggtaatttctctcctctctattttacca
ttttccattgacgacgatctaggttttctgatttgattttggagaacgcctcgatgagtttatagattcgtagat
tggttttgagattcagtataatttcacccggattccaattttgaaccgatacctaattttgaatt gatttggta
gatcgattggtcaaatttgaaattgattttctccataatatctgaagcgtcttattggatcaaatctacaacat
ttctctgttgaaaggatcgattttttttttcttggaacatgataacttttgattattcatcaaagttttgttctt
tttaatatttcacaggt Figure 12 (SEQ ID NO: 12) AT3G08580
caaatatcatattcatatagaagaaaataaacaaagttgtaaaaatctggcatttaaaataaaattgaacacttc
aatttatttcctttcataataataattttggcataagatatttgcaaattgatctggttcggtatggtcgacaaa
ataattttccacgctacccttccagccgtccattcactatttgccctcaacgttaccaaataacggtccagattc
ctagggcaagatctaacggttagcaagtaaagtcgtaccatcagaaagaataacaattcttttcacaaagtaaaca
taaccaacggttaacaagttcttagggttaaatcagtaagatccaacggatattaaattgcaaggcccaaatagt
ttttttgcagcagataataactcgtccccactggcgagtgacgaccgagactctgtgaccctattttcgagacg
ataaaagggcaaacaatcgctcttttcaaagctcgcctcttcaccacagagaaaacttcgtctctcttctctgct
tcgccctctcatttcctgtgagataaaggcggagtctctctccagttattttgctcatccatcgattcttaggta
tgactcgtttctctcagatctgtgattctttataatctcgtcgttcttcaaatcattGttatattcgtttcttcg
atctgtgtttttagatctgtaaggtaaatgagacgtttcgatctgtagatctgattgttatattgatagattat
gttatctgctttgcttaaagtccgatcggaatgttttgtgctcattgtcgaatatctgatgtatcggtttcatag
atctgcttcttttgtgcgtttcgttgatctgataatcttctagtgatcaaaatcgtttggatctgttgacttta
gtttaaaatgtatccgatctgatgtcgaggcttcattattggaagttgttattgttgtaatcctgatttaagttg
ctgttcttaaatttatatgatctttgcgttataatatgacatggtagatcttggttcatggttcactgttttcca
ataaacttggtttgtttggttggatagcgttctgtgatacgaccatgtcttgtgttggataagaattctctgaat
ttccttggctggtttgtagtatgttattcacgtctggtttctcatcaatgattatgtgattttgcagagttcaaa Figure 13 (SEQ ID NO: 13) AT3G08580, +35S minimal promoter
caaatatcatattcatatagaagaaaataaacaaagttgtaaaaatctggcatttaaaataaaattgaacacttc
aatttatttcctttcataataataattttggcataagatatttgcaaattgatctggttcggtatggtcgacaaa
ataattttccacgctacccttccagccgtccattcactatttgccctcaacgttaccaaataacggtccagattc
ctagggcaagatctaacggttagcaagtaaagtcgtaccatcagaaagaataacaattcttttcacaaagtaaaca
taaccaacggttaacaagttcttagggttaaatcagtaagatccaacggatattaaattgcaaggcccaaatagt
ttttttgcagcagataataactcgtccccactggcgagtgacgaccgagactctgtgaccctattttcgagacg
ataaaagggcaaacaatcgctcttttcaaagctcgcctcttcaccacagagaaaacttcgtctctcttctctgct
tcgccctctcatttcctgtgagataaaggcggagtctctctccagttattttgctcatccatcgattcttaggta
tgactcgtttcgcaagacccttcctctatataaggaagttcatttcatttggagaggGttatattcgtttcttcg
atctgtgtttttagatctgtaaggtaaatgagacgtttcgatctgtagatctgattgttatattgatagattat
gttatctgctttgcttaaagtccgatcggaatgttttgtgctcattgtcgaatatctgatgtatcggtttcatag
atctgcttcttttgtgcgtttcgttgatctgataatcttctagtgatcaaaatcgtttggatctgttgacttta
gtttaaaatgtatccgatctgatgtcgaggcttcattattggaagttgttattgttgtaatcctgatttaagttg
ctgttcttaaatttatatgatctttgcgttataatatgacatggtagatcttggttcatggttcactgttttcca
ataaacttggtttgtttggttggatagcgttctgtgatacgaccatgtcttgtgttggataagaattctctgaat
ttccttggctggtttgtagtatgttattcacgtctggtttctcatcaatgattatgtgattttgcagagttcaaa Figure 14 (SEQ ID NO: 14) AT1G51650, +first intron
ggaggaggatatgattgttgcttcaacaactatatatggatttgataacaatcctttatcctcggaagataaacc
aaatttcttaccaaacccaccaaaataagtaattaccagtgttcttcttctaaagacttctataaaccaaaacaa
gatcacatataatcattaacttaaagcaaaacccaaagtcttgttttatttgttagtcagctcaaccatctttat
ctgaaactaaactgtttctctcttctttgtttctgacaagtcaatgagattggtgtcttctctctgttgcacatt
taatattaacttttgaaaaactacaaaacgaaacaaaacaaagaaaagcagacatttacacgaaattatgcagac
atatacacgaaattcaatctacctgaaaatgagaataagttttgagtaaatttcgtggagactcctggaaataag
tttgtttgttttcctatttttatgtaacttcgcttaaatttctaattgcctaatcaaggtattaaaatagcaaag
cttggtttggctcagtcttcgcgtaaactccaagaaacaatcataaaaacaataaaaaagacaagaaaccaaaa
aaaaaaaaagttgagagatttcagtagatgaaagttggatagaagattcgtgtagttagctacttaatgggcc
gttaaaatatttaataaggcccattgggtctaaactgtgttaggattactagggcacagaatcggtctctgtccc
Atttcgcgaactttctccttagaatcggaacggacgaaggaaggaagaaggaagaagatcggagcaggtaagcc
ttttcgatcctttaatcgtcgatgttggatcttagatctggattcttcacgttcttgtgttctcgattcctgatt
tgtttttgagtaaatttgttggaataatctgatttcctaaaagttatcggaattaagtggaaagtgaatcatctgc
ttctggatttgatcttcgattttgcatttaaccttcctctgcttctggatttgatcagttcaatactatcttca tacaatgttgttatgtccaaattgttgaattttttcatttagagttagcttcagagaaaacaacaaaactagtagt
atgtgtgaaacaagaacatgaagaagatggaaagctgattgggaacattgcatttagatgtcttttctcgtttat
gtttggatctgaattcttcatgttcttgttgtgtgtcattgaaattgttggaatacgtagatatcagagtaggtc
attttgggaaagctattgaatttaagaggaagatgaatcattttaacaagctccatcgattttgcgcttaatctg
tctctcttctgcttctggatttgattaatttcattctattttgttttctcataagttgttgttatgttcaaattg
ttgaatttggaatgatttcatttctcaaatagggtttactgagacaatgattccagatttagtctatctgaaaat
ggttcagctttcttcttgttgatccatttgtctaacattctctcatgttttgttttccttgacaggt Figure 15 (SEQ ID NO: 15) AT1G51650
ggaggaggatatgattgttgcttcaacaactatatatggatttgataacaatcctttatcctcggaagataaacc
aaatttcttaccaaacccaccaaaataagtaattaccagtgttcttcttctaaagacttctataaaccaaaacaa
gatcacatataatcattaacttaaagcaaaacccaaagtcttgttttatttgttagtcagctcaaccatctttat
ctgaaactaaactgtttctctcttctttgtttctgacaagtcaatgagattggtgtcttctctctgttgcacatt
taatattaacttttgaaaaactacaaaacgaaacaaaacaaagaaaagcagacatttacacgaaattatgcagac
atatacacgaaattcaatctacctgaaaatgagaataagttttgagtaaatttcgtggagactcctggaaataag
tttgtttgttttcctattttatgtaacttcgcttaaatttctaattgcctaatcaaggtattaaaatagcaaag
cttggtttggctcagtcttcgcgtaaactccaagaaacaatcataaaaacaataaaaaagacaagaaaccaaaa
aaaaaaaaaagttgagagatttcagtagatgaaagttggatagaagattcgtgtagttagctacttaatgggcc
gttaaaatatttaataaggcccattgggtctaaactgtgttaggattactagggcacagaatcggtctctgtccc
Atttcgcgaactttctccttagaatcggaacggacgaagaaggaagacaaggaagaagatcggag Figure 16 (SEQ ID NO: 16) AT1G51650, +first intron, +35S minimal promoter
ggaggaggatatgattgttgcttcaacaactatatatggatttgataacaatcctttatcctcggaagataaacc
aaatttcttaccaaacccaccaaaataagtaattaccagtgttcttcttctaaagacttctataaaccaaaacaa
gatcacatataatcattaacttaaagcaaaacccaaagtcttgttttatttgttagtcagctcaaccatctttat
ctgaaactaaactgtttctctcttctttgtttctgacaagtcaatgagattggtgtcttctctctgttgcacatt
taatattaacttttgaaaaactacaaaacgaaacaaaacaaagaaaagcagacatttacacgaaattatgcagac
atatacacgaaattcaatctacctgaaaatgagaataagttttgagtaaatttcgtggagactcctggaaataag
tttgtttgttttcctattttatgtaacttcgcttaaatttctaattgcctaatcaaggtattaaaatagcaaag
cttggtttggctcagtcttcgcgtaaactccaagaaacaatcataaaaacaataaaaaagacaagaaaccaaaa
aaaaaaaaaagttgagagatttcagtagatgaaagttggatagaagattcgtgtagttagctacttaatgggcc
gttaaaatatttaataaggcccattgggtgcaagacccttcctctatataaggaagttcatttcatttggagagg
Atttcgcgaactttctccttagaatcggaacggacgaagaaggaagacaaggaagaagatcggagcaggtaagcc
ttttcgatcctttaatcgtcgatgttggatcttagatctggattcttcacgttcttgtgttctcgattcctgatt
tgtttttgagtaatttgttggaataatctgatttcctaaaagttatcggaattaagtggaaagtgaatcatctgc
ttctggatttgatcttcgattttgcatttaacctttcctctgcttctggatttgatcagttcaatactatcttca
tacaatgttgttatgtccaaattgttgaattttttcatttagagttagcttcagagaaaacaacaaaactagtagt
atgtgtgaaacaagaacatgaagaagatggaaagctgattgggaacattgcatttagatgtcttttctcgtttat
gtttggatctgaattcttcatgttcttgttgtgtgtcattgaaattgttggaatacgtagatatcagagtaggtc
attttgggaaagctattgaatttaagaggaagatgaatcattttaacaagctccatcgattttgcgcttaatctg
tctctcttctgcttctggatttgattaatttcattctattttgttttctcataagttgttgttatgttcaaattg
ttgaatttggaatgatttcatttctcaaatagggtttactgagacaatgattccagatttagtctatctgaaaat
ggttcagctttcttcttgttgatccatttgtctaacattctctcatgttttgttttccttgacaggt Figure 17 (SEQ ID NO: 17) AT3G48140, +first intron
aaaattaatattaataaaataaatggcttttggcaagacggatttggaggaatgggttttggatcaacattaa
gaaaaagtaaaatataattaatccaccgtttcaatacgggttaaatctttaatttattattttttaagactacta
atattaaacatatcaaatcatcctaatttagaaaagattatataaaaccaaaaatgttatgtggtatgtataatg
ttactatatataaaattaaactataaaatatatattagagaatgatacaatttacaaaacttttatatataataa
ataattcttaaattttaaaaattactacttaaaaaaaattcacggaacgggtaaagaaattatagaataggttt
tattttggaattgagttatatggtggatgtatttgaatcaatatttataaaattctaaaatattattaatatga
tgttttaataaggattaaaacttcagttttttaacaattgtcgcatagattcgtggtatagcgttacttaataac
aattataaactgaaaaatttaaatattttataaaaataaaatttacaagtttaatatatattaactttaaaata
taaatcgtcccgcggtataccgcggattaaaatctagtttgctataaaaaaagtaacgtaaaaattgttgccaat
tagatattaccaataaagaaatttaaaatatatgggttgaaaaaagagaagaagataagaatcgtatcttattac
aacttgccaatttgctatcgtttcgtaacagctaaacagttcaaataaaacggtgtctcgaaacactaaatagac
agatgtcaatacctcattggatttaagcataacgcctcgctgccaattagaattcagcattccaatttcatttta
ttttctcacaaaattctccaaaaaaccctAaaagtcaaataaatataaagtgaggtcttttctacgtctcttcaac attctcagagaagccgtcttcttcctccttcaatctctctcgttcgtatcatctgctctgcgatttca<u>ggtacta</u>
<u>cttcatttttgatctttgattttccctaaatcgaaatccatcggttgattctctgttgactacgtcttatttctaa</u>
<u>atccttagatctagattcgattcttgtaagaattagcctcgtgaatcaatatgataacgtgtttcattgttttta</u>
ggt Figure 18 (SEQ ID NO: 18) AT3G48140
aaaattaatattaataaaataaatggcttttggcaagacggatttggaggaatgggttttggatcaacattaa
gaaaaagtaaaatataattaatccaccgtttcaatacgggttaaatctttaatttattattttttaagactacta
atattaaacatatcaaatcatcctaatttagaaaagattatataaaaccaaaaatgttatgtggtatgtataatg
ttactatatataaaattaaactataaaatatatattagagaatgatacaatttacaaaactttatatataataa
ataattcttaaattttaaaaattactactttaaaaaaaattcacggaacgggtaaagaaattatagaataggttt
tattttttggaattgagttatatggtggatgtatttgaatcaatatttataaaattctaaaatattattaatatga
tgttttaataaggattaaaacttcagttttttaacaattgtcgcatagattcgtggtatagcgttacttaataac
aattataaactgaaaaatttaaatatttatataaaaataaaatttacaagttttaatatatattaactttaaaata
taaatcgtcccgcggtataccgcggattaaaatctagtttgctataaaaaaagtaacgtaaaaattgttgccaat
tagatattaccaataaagaaatttaaaatatatgggttgaaaaaagagaagaagataagaatcgtatcttattac
aacttgccaatttgctatcgtttcgtaacagctaaacagttcaaataaaacggtgtctcgaaacactaaatagac
agatgtcaatacctcattggatttaagcataacgcctcgctgccaattagaattcagcattccaatttcatttta
ttttctcacaaaattctccaaaaaacctAaaagtcaaataaatataaagtgaggtcttttctacgtctcttcaac
attctcagagaagccgtcttcttcctccttcaatctctctcgttcgtatcatctgctctgcgatttca Figure 19 (SEQ ID NO: 19) AT3G48140, +first intron, +35S minimal promoter
aaaattaatattaataaaataaatggcttttggcaagacggatttggaggaatgggttttggatcaacattaa
gaaaaagtaaaatataattaatccaccgtttcaatacgggttaaatctttaatttattattttttaagactacta
atattaaacatatcaaatcatcctaatttagaaaagattatataaaaccaaaaatgttatgtggtatgtataatg
ttactatatataaaattaaactataaaatatatattagagaatgatacaatttacaaaactttatatataataa
ataattcttaaattttaaaaattactactttaaaaaaaattcacggaacgggtaaagaaattatagaataggttt
tattttttggaattgagttatatggtggatgtatttgaatcaatatttataaaattctaaaatattattaatatga
tgttttaataaggattaaaacttcagttttttaacaattgtcgcatagattcgtggtatagcgttacttaataac
aattataaactgaaaaatttaaatatttatataaaaataaaatttacaagttttaatatatattaactttaaaata
taaatcgtcccgcggtataccgcggattaaaatctagtttgctataaaaaaagtaacgtaaaaattgttgccaat
tagatattaccaataaagaaatttaaaatatatgggttgaaaaaagagaagaagataagaatcgtatcttattac
aacttgccaatttgctatcgtttcgtaacagctaaacagttcaaataaaacggtgtctcgaaacactaaatagac
agatgtcaatacctcattggatttaagcataacgcctcgctgccaattagaattcagg<u>caagacccttcctctat</u>
<u>ataaggaagttcatttcatttggagagg</u>Aaaagtcaaataaatataaagtgaggtcttttctacgtctcttcaac
attctcagagaagccgtcttcttcctccttcaatctctctcgttcgtatcatctgctctgcgatttca<u>ggtacta</u>
<u>cttcatttttgatctttgattttccctaaatcgaaatccatcggttgattctctgttgactacgtcttatttctaa</u>
<u>atccttagatctagattcgattcttgtaagaattagcctcgtgaatcaatatgataacgtgtttcattgttttta</u>
ggt Figure 20 (SEQ ID NO: 20) AT3G08610, +first intron
actaaaaccctacatttccttttgcgtttttatggccgtaacttccggttcacggtgttactttatcgtactaa
atataagttttaacgtctgatatatataaatcgtgtcaaacaagaaaatatatcattaataaacagagattttaa
tttgtaacgtgtcaatctgatataactgtccgtagattttctttatttactaatttatttgtgtatctcgtgtct
taaatatccgtagattctcgtttacttgcttagtttgacatatttcatttcttactcggtactcgccttttaatc
gatcgtgtttaatatcttctataagaaaacattacttccaagtgtatactgtcttcatcatccagcttcatacgg
ttgtgggataaaatttgattactagggaaagcttacatgtactaacttggggtcataagtcataacactagtact
accaagtaggttatctagttattaccaccgtccgtgaccatgtatccatccaatccatgaaaaagtcaaaaacat
ttcatttggatgtattgggctttgagatttacgtttcattaaaaatgaagcccaaaagcccattattatccaatt
gactagagtggtctctgatcccaaatctttaacttggatcttaacacaga<u>G</u>aagaagcacaatcggaagaaagga
gaagacgaagc<u>ag</u>gtatgaatttccccctttcgattcattgctctctctctcctagggtttgctcgatttg
atccggtttatacaaatttgggtactctattgaacatttggttgatgatttgatttgaatttgtgattgggcagg
t Figure 21 (SEQ ID NO: 21) AT3G08610
actaaaaccctacatttccttttgcgtttttatggccgtaacttccggttcacggtgttactttatcgtactaa
atataagttttaacgtctgatatatataaatcgtgtcaaacaagaaaatatatcattaataaacagagattttaa
tttgtaacgtgtcaatctgatataactgtccgtagattttctttatttactaatttatttgtgtatctcgtgtct

```
taaatatccgtagattctcgtttacttgcttagtttgacatatttcatttcttactcggtactcgccttttaatc
gatcgtgtttaatatcttctataagaaaacattacttccaagtgtatactgtcttcatcatccagcttcatacgg
ttgtgggataaaatttgattactagggaaagcttacatgtactaacttggggtcataagtcataacactagtact
accaagtaggttatctagttattaccaccgtccgtgaccatgtatccatccaatccatgaaaaagtcaaaaacat
ttcatttggatgtattgggctttgagatttacgtttcattaaaaatgaagcccaaaagcccattattatccaatt
gactagagtggtctctgatcccaaatctttaacttggatcttaacacagaGaagaagcacaatcggaagaaagga
gaagacgaag
```

Figure 22 (SEQ ID NO: 22) AT3G62250
```
tttttattttcttttttttataacttttggtgagcttaatggcccaatagactgctctgtgaaagcccaaaacta
agcccaaataaaataagggtagtaacgtaattgagctaagaaaccctagaggtctccttcgcctacAaaatcccc
attttgataatcttcagcagccgttgcctcaaaag
```

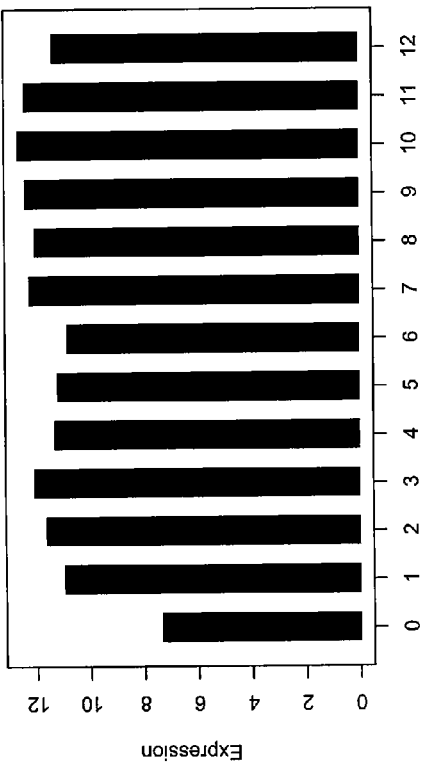
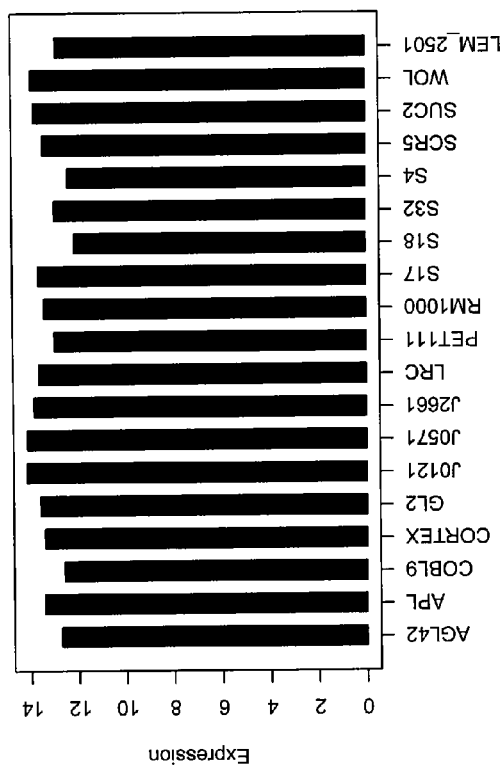
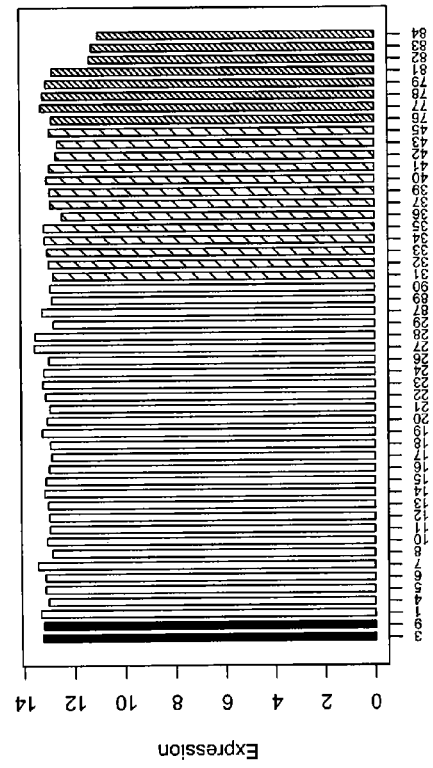

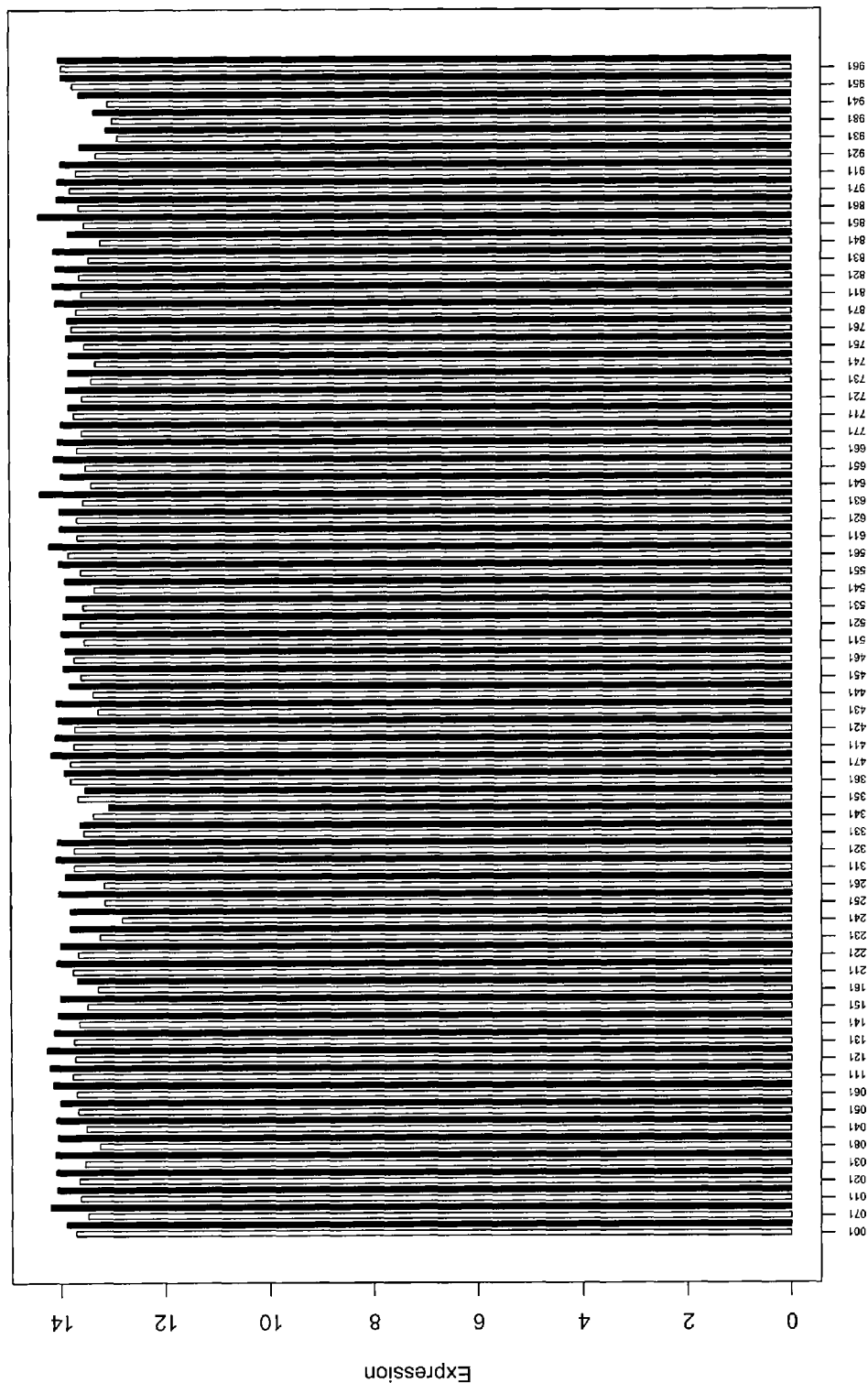
Fig. 23 (D) Abiotic stresses

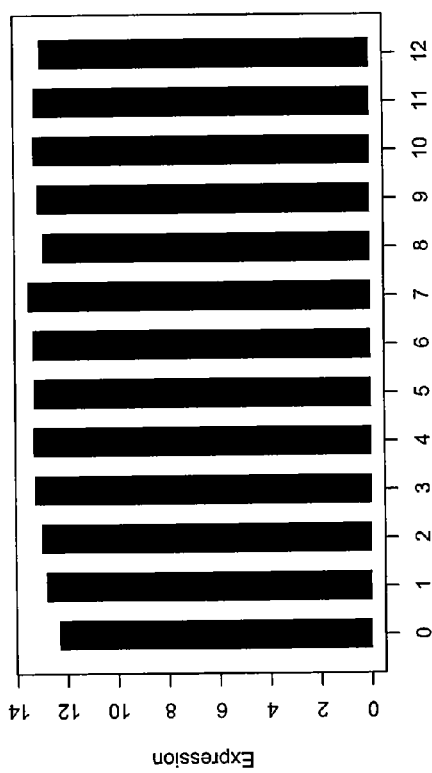
Fig. 24 (A) Root tissue markers
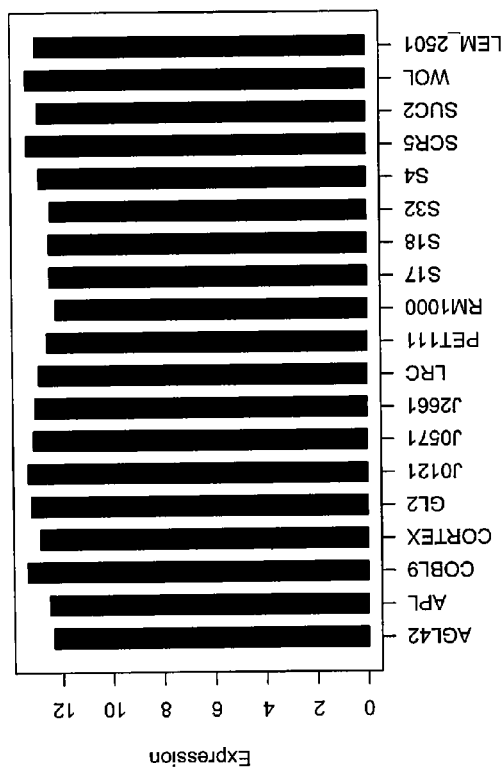
Fig. 24 (B) Root developmental zones
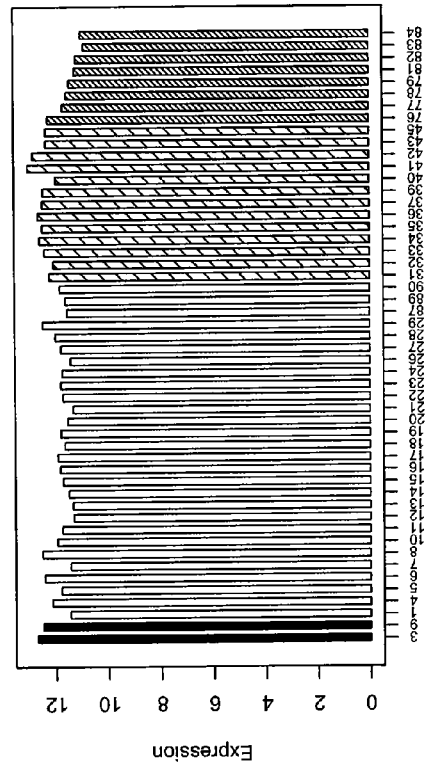
Fig. 24 (C) Roots, shoots, flowers, seeds

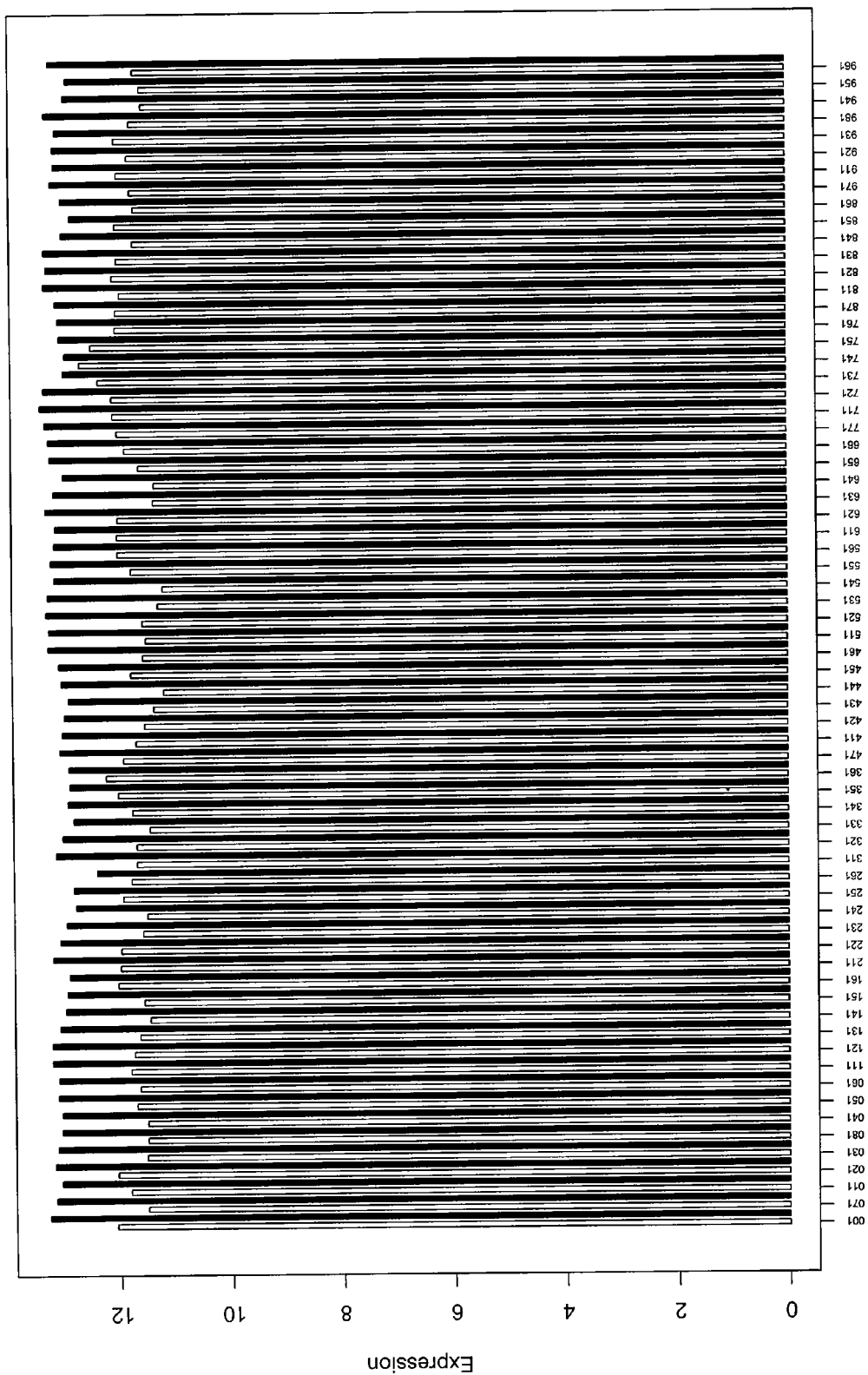
Fig. 24 (D) Abiotic stresses

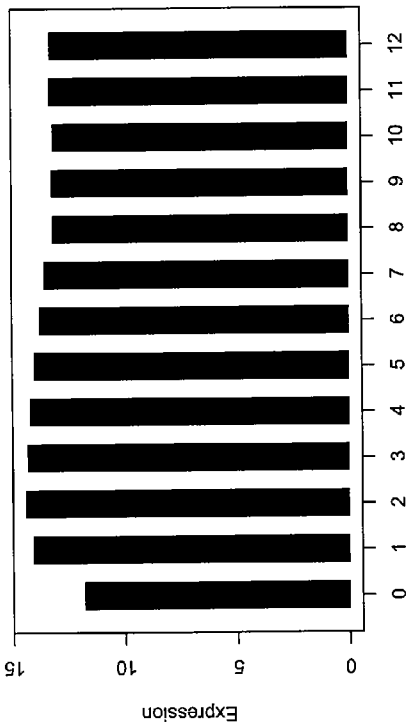
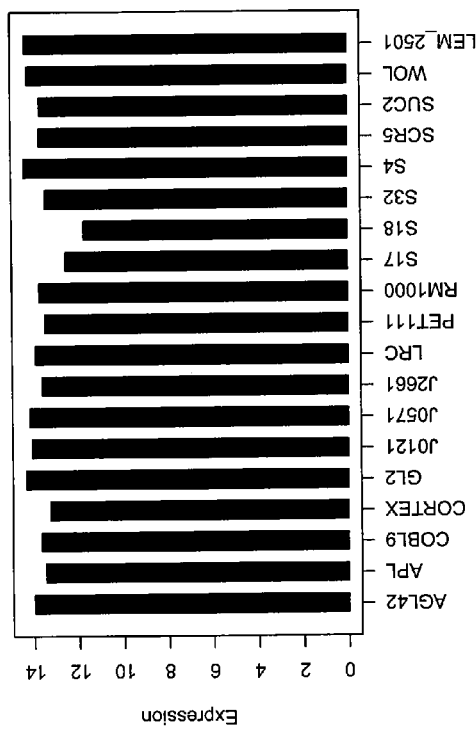
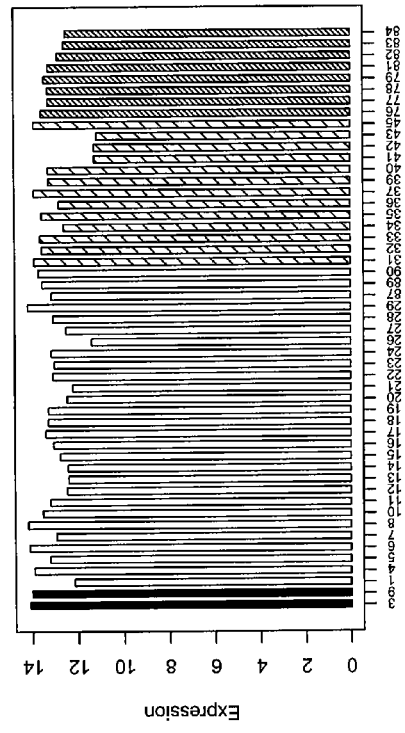

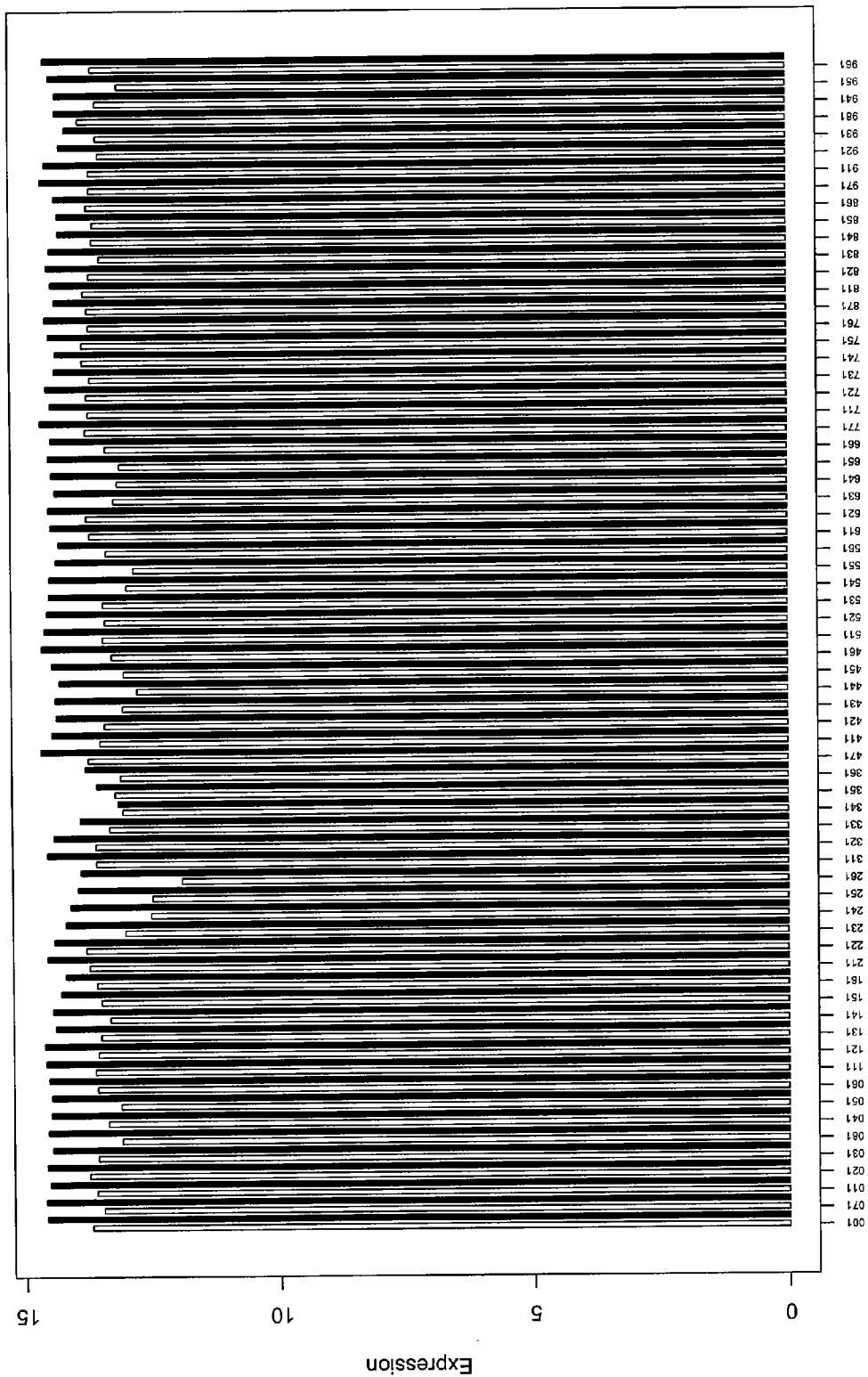
Fig. 25 (D) Abiotic stresses

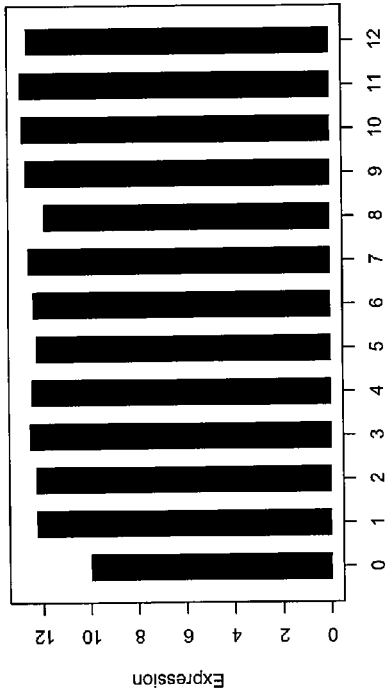
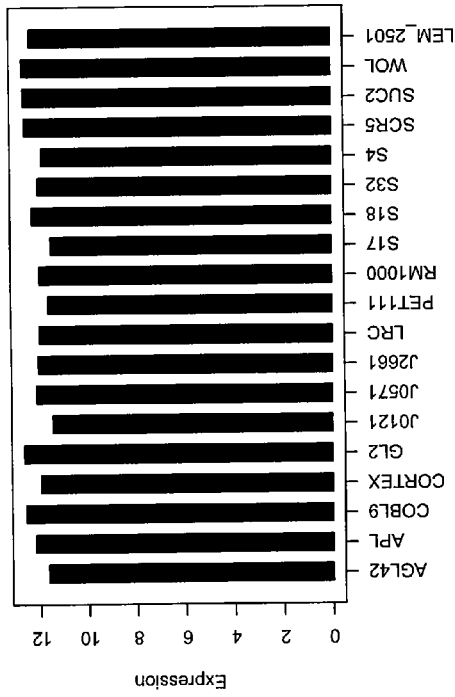
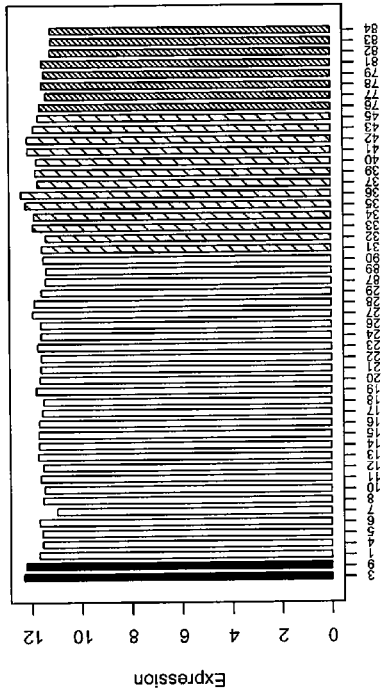
Fig. 26 (A) Root tissue markers
Fig. 26 (B) Root developmental zones
Fig. 26 (C) Roots, shoots, flowers, seeds

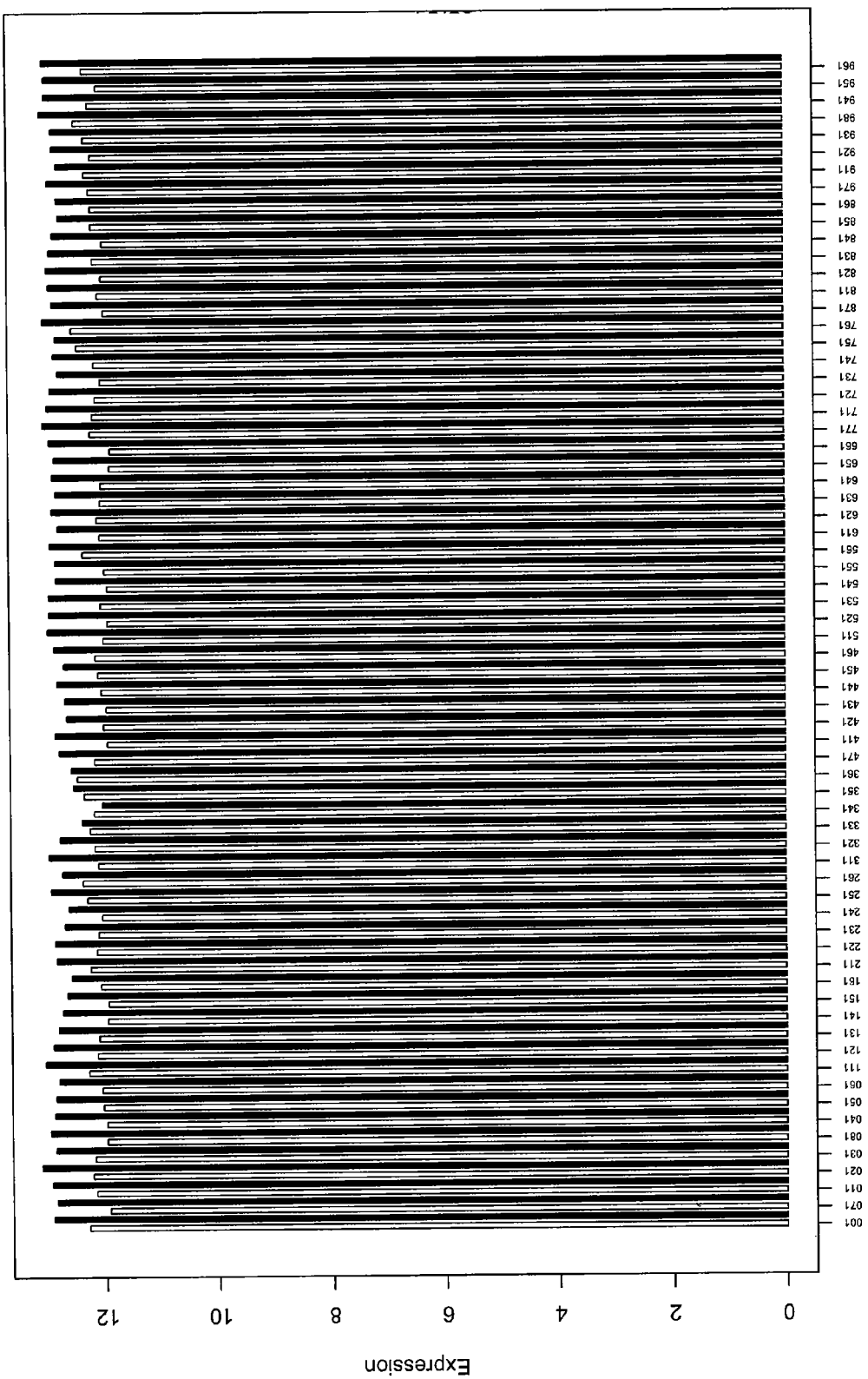
Fig. 26 (D) Abiotic stresses

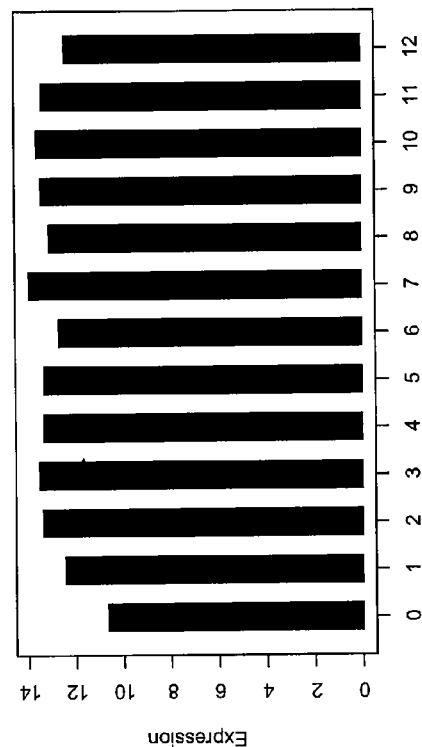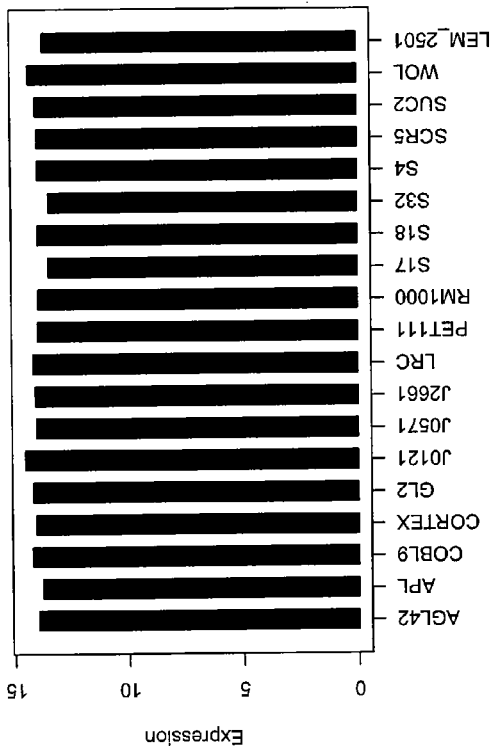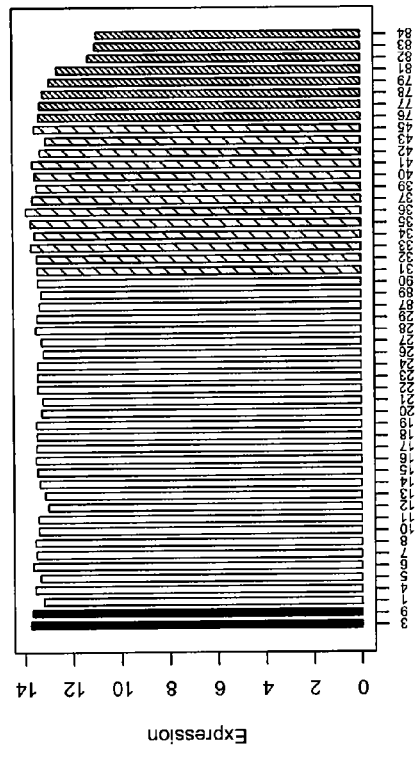
Fig. 27 (A) Root tissue markers
Fig. 27 (B) Root developmental zones
Fig. 27 (C) Roots, shoots, flowers, seeds

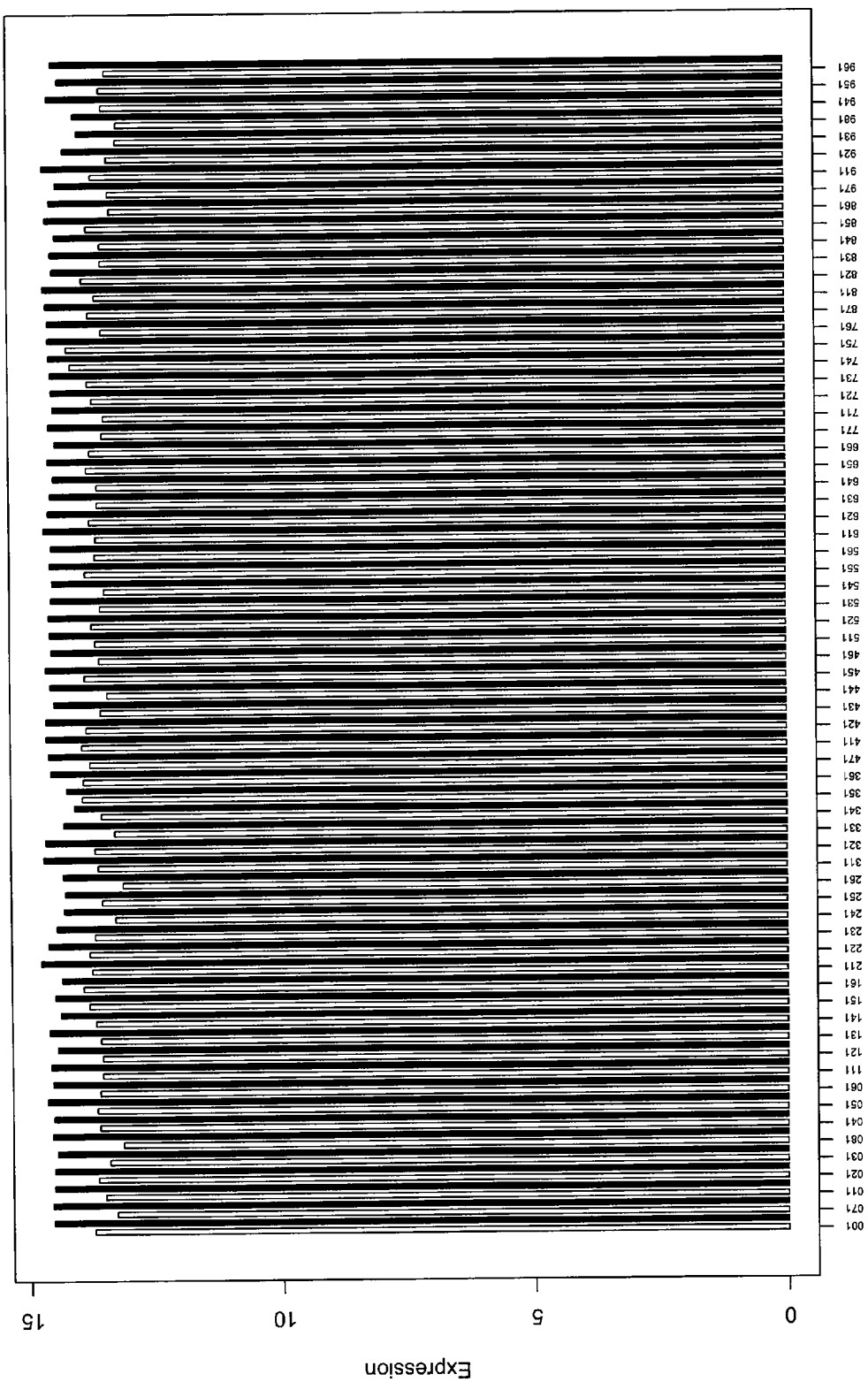
Fig. 27 (D) Abiotic stresses

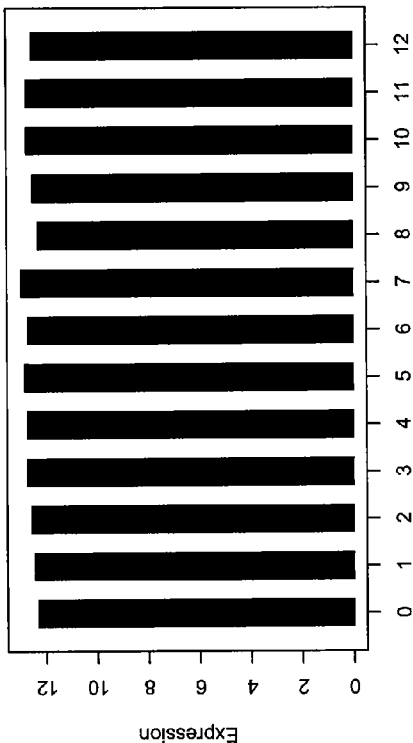
Fig. 28 (A) Root tissue markers
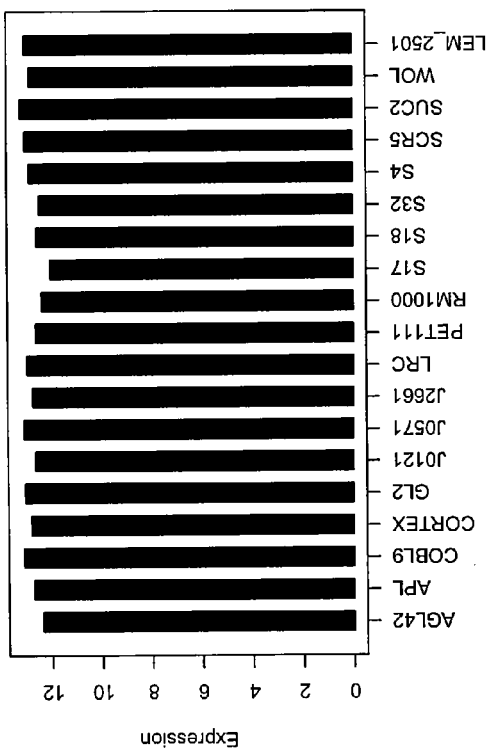
Fig. 28 (B) Root developmental zones
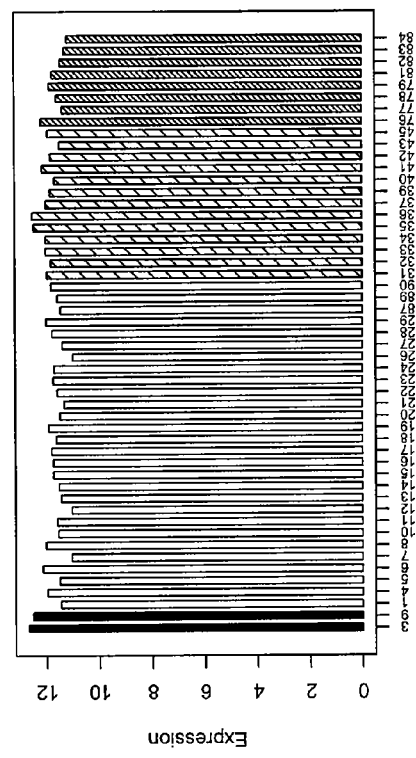
Fig. 28 (C) Roots, shoots, flowers, seeds

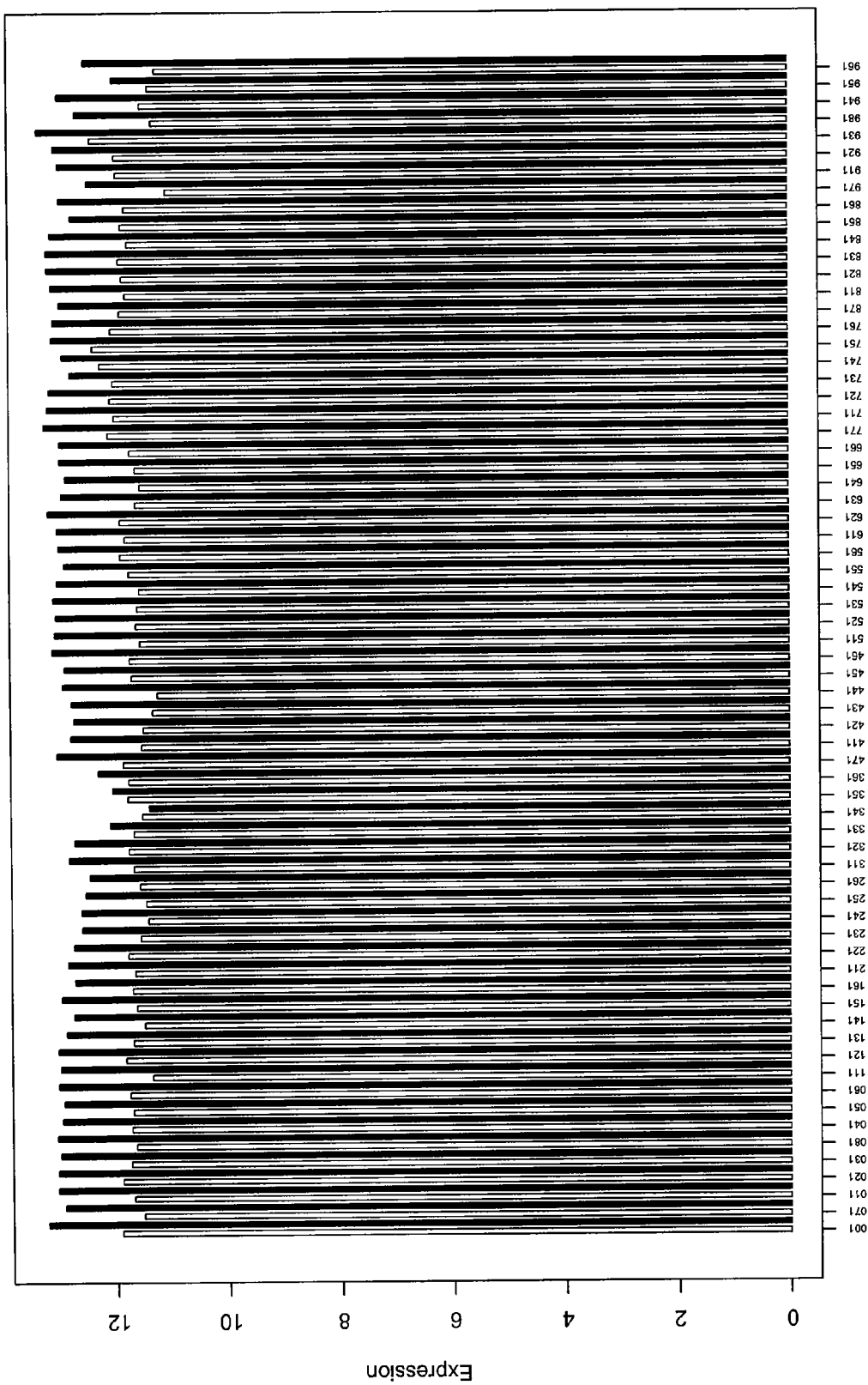
Fig. 28 (D) Abiotic stresses

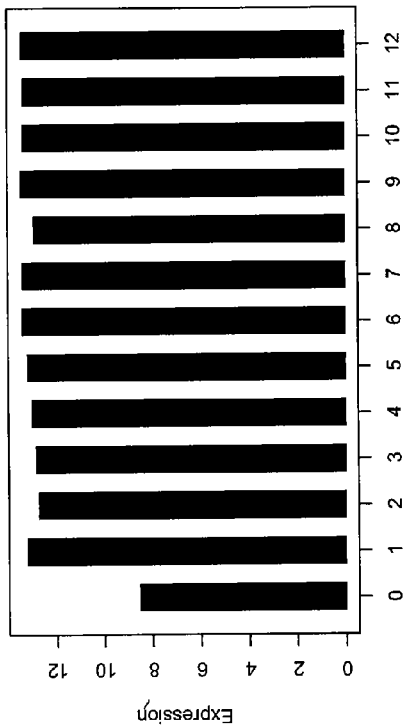
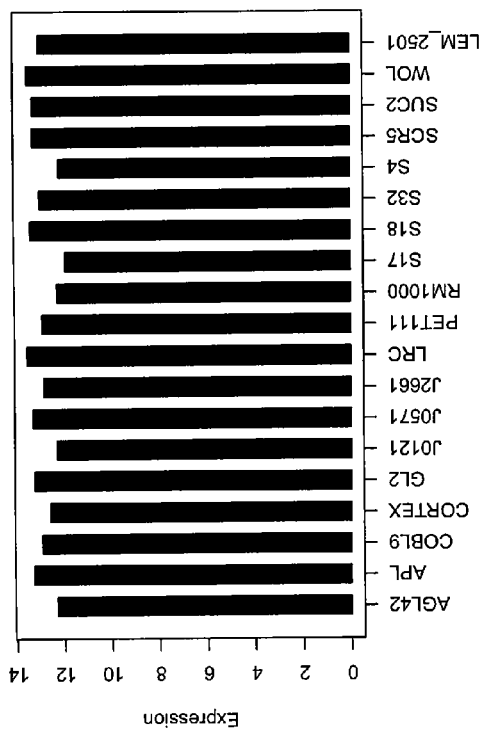
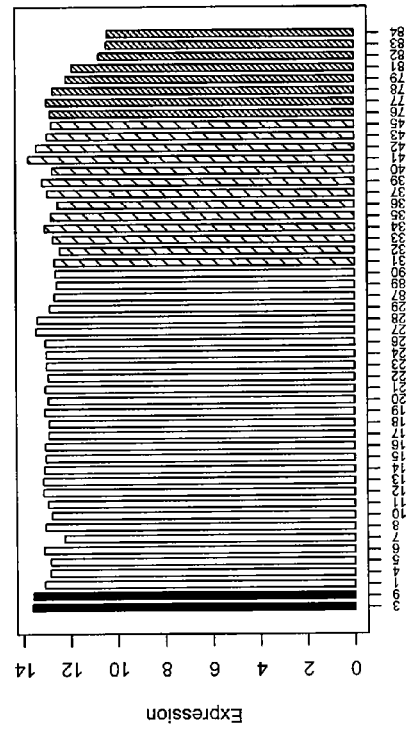

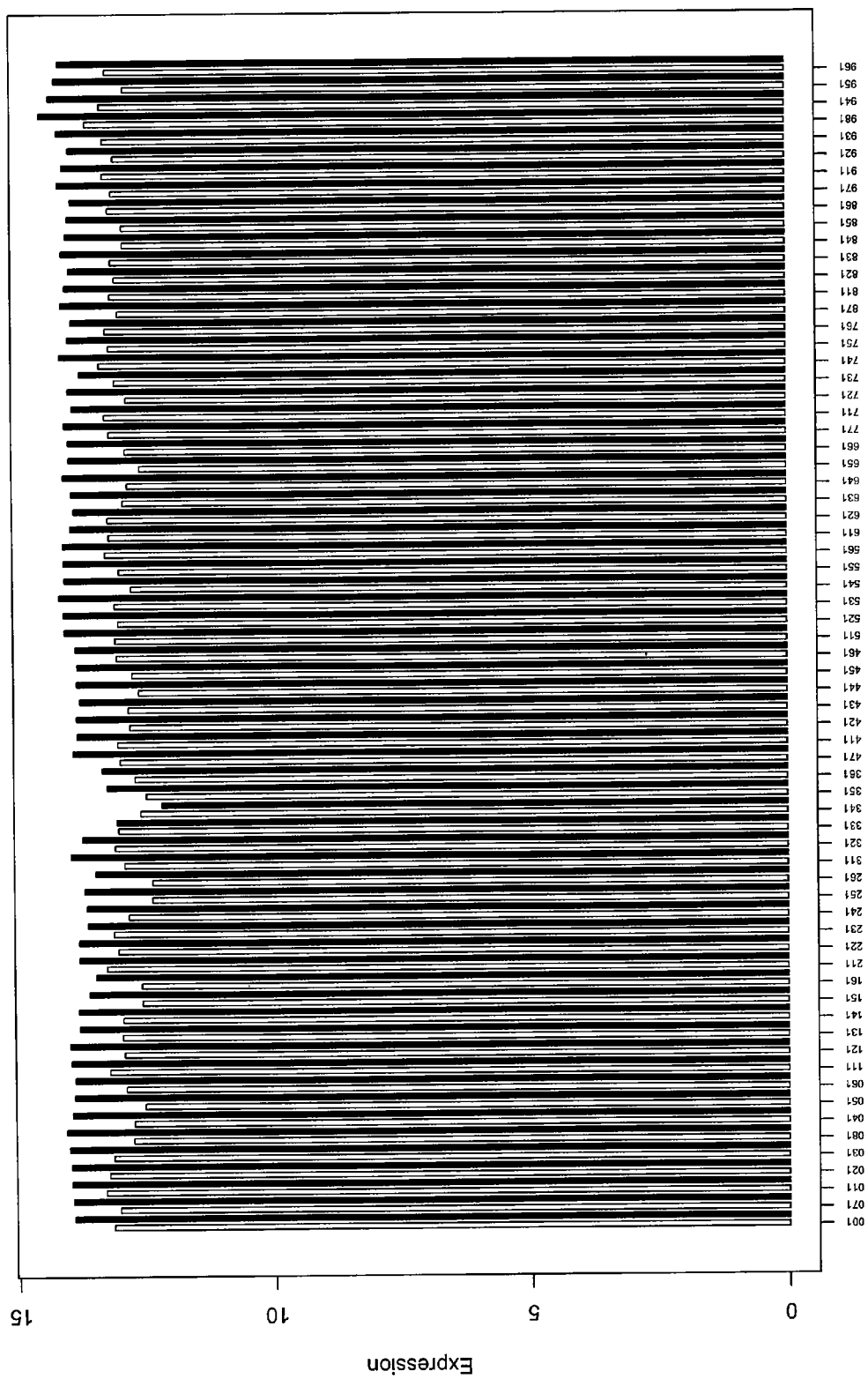
Fig. 29 (D) Abiotic stresses

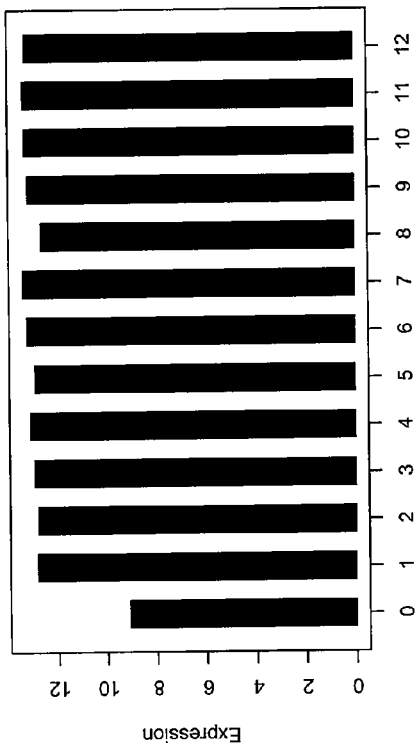
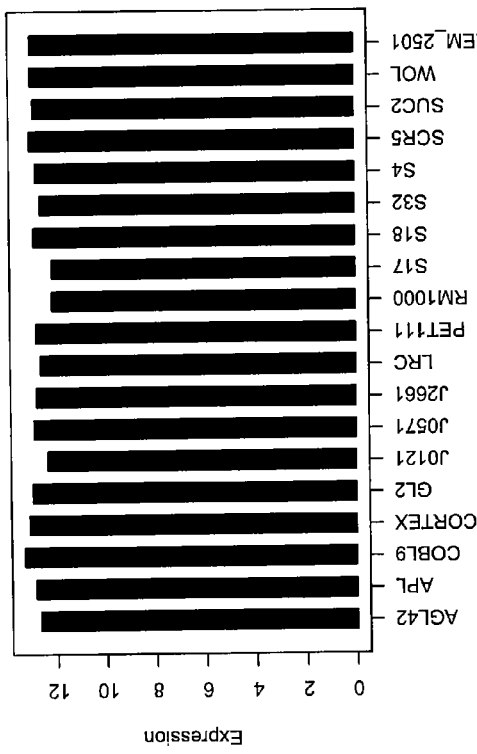
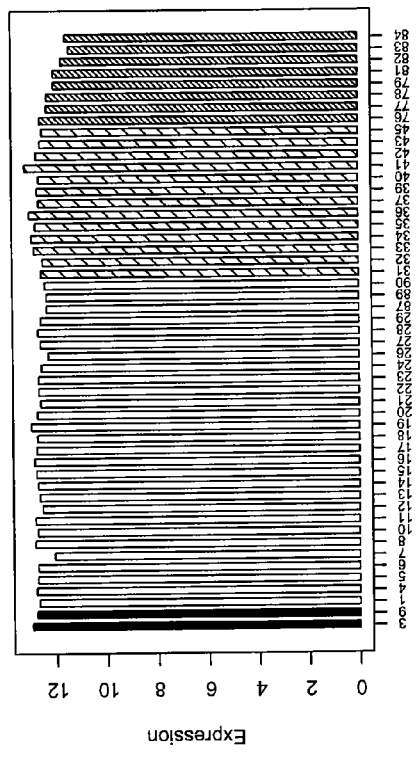

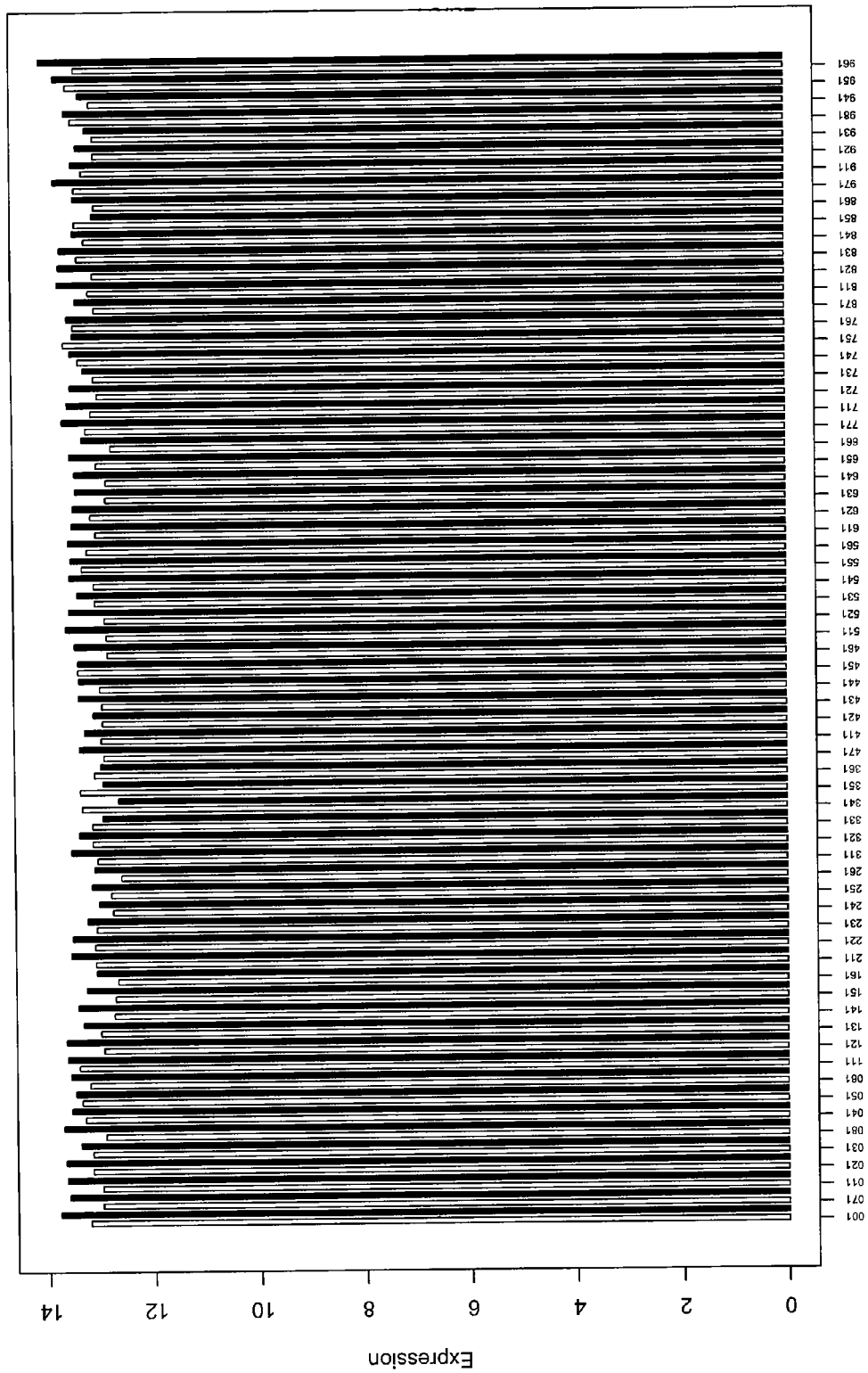
Fig. 30 (D) Abiotic stresses

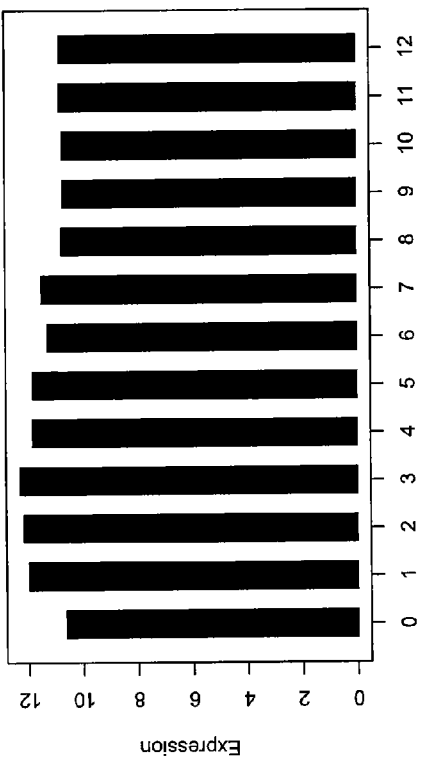
Fig. 31 (B) Root developmental zones
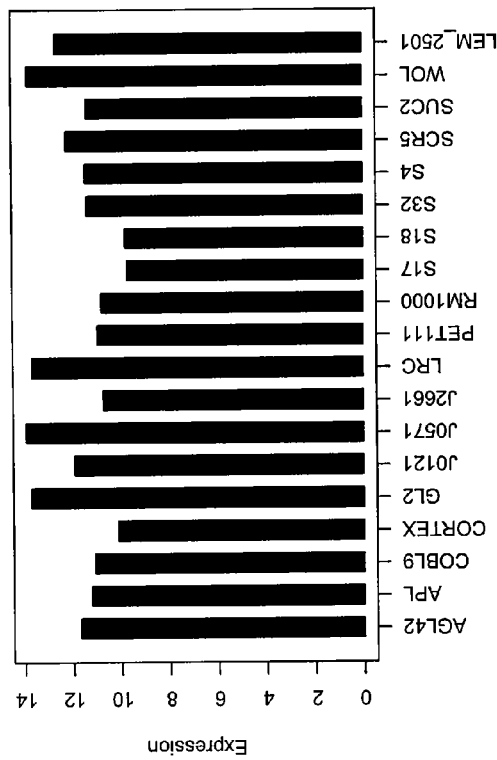
Fig. 31 (A) Root tissue markers
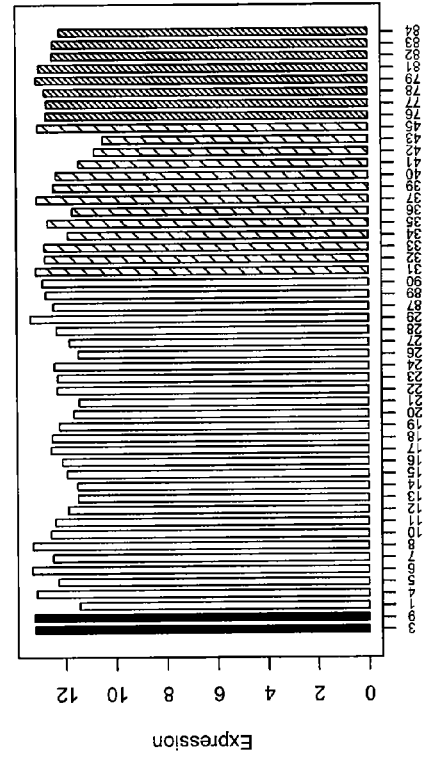
Fig. 31 (C) Roots, shoots, flowers, seeds

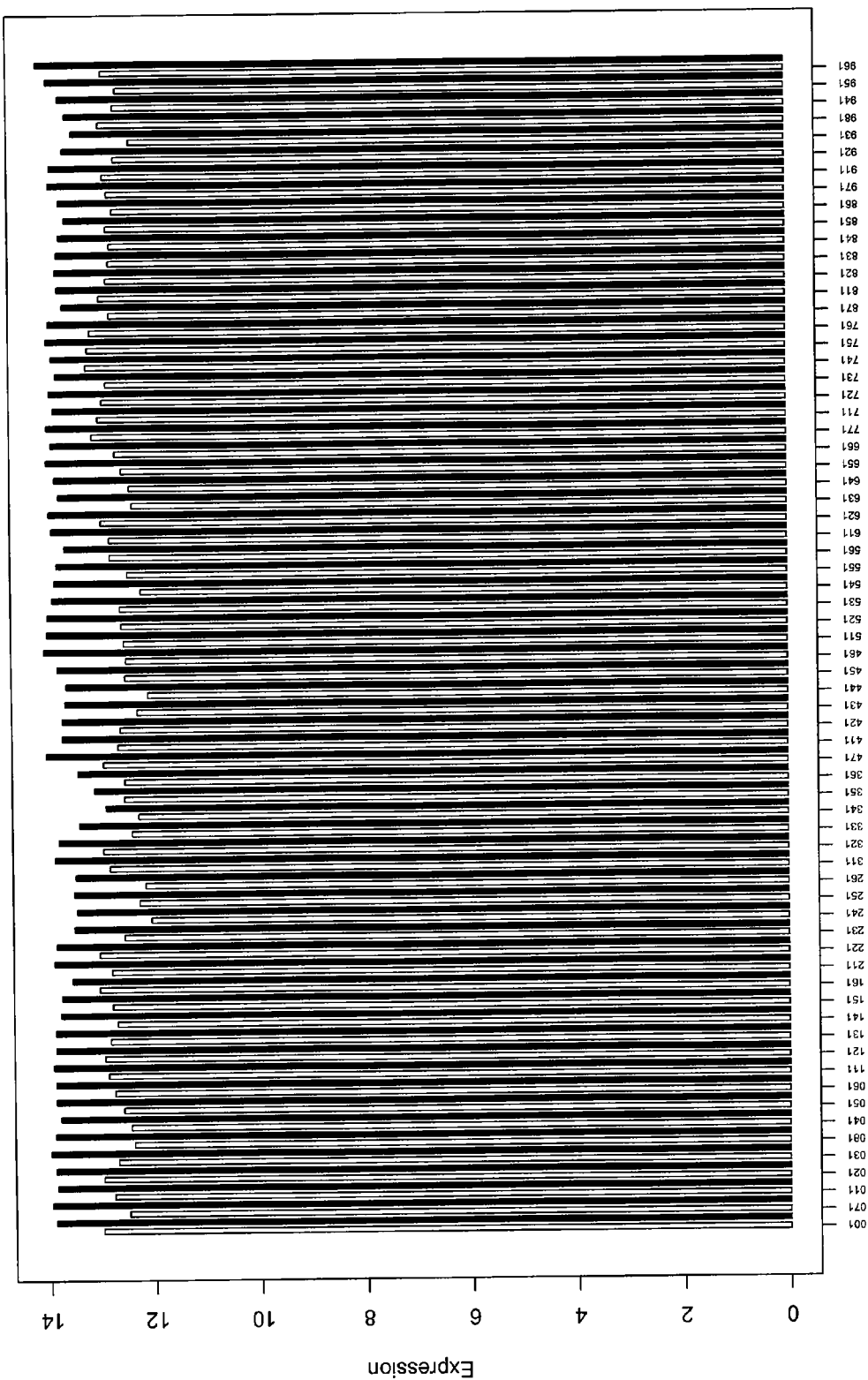
Fig. 31 (D) Abiotic stresses

Figure 32A (SEQ ID NO: 24), AT4G05320 (UBQ10)

gttttgtgtatcattcttgttacattgttattaatgaaaaaatattattggtcattggactg
aacacgagtgttaaatatggaccaggccccaaataagatccattgatatatgaattaaataa
caagaataaatcgagtcaccaaaccacttgccttttttaacgagacttgttcaccaacttga
tacaaaagtcattatcctatgcaaatcaataatcatacaaaaatatccaataacactaaaaa
attaaaagaaatggataatttcacaatatgttatacgataaagaagttacttttccaagaaa
ttcactgattttataagcccacttgcattagataaatggcaaaaaaaaacaaaaaggaaaag
aaataaagcacgaagaattctagaaaatacgaaatacgcttcaatgcagtgggacccacggt
tcaattattgccaattttcagctccaccgtatatttaaaaaataaaacgataatgctaaaaa
aatataaatcgtaacgatcgttaaatctcaacggctggatcttatgacgaccgttagaaatt
gtggttgtcgacgagtcagtaataaacggcgtcaaagtggttgcagccggcacacacgagtc
gtgtttatcaactcaaagcacaaatacttttcctcaacctaaaaataaggcaattagccaaa
aacaactttgcgtgtaaacaacgctcaatacacgtgtcattttattattagctattgcttca
ccgccttagctttctcgtgacctagtcgtcctcgtcttttcttcttcttcttctataaaaca
ataccCaaagagctcttcttcttcacaattcagatttcaatttctcaaaatcttaaaaactt
tctctcaattctctctaccgtgatcaag<u>gtaaatttctgtgttccttattctctcaaaatct</u>
<u>tcgatttt gtttt cgttcgatcccaatttcgtatatgttctttggtttagattctgttaatc</u>
<u>ttagatcgaagacgatttt ctgggtttgatcgttagatatcatcttaattctcgattagggt</u>
<u>ttcatagatatcatccgatttgttcaaataatttgagttttgtcgataattactcttcgat</u>
<u>ttgtgatttctatctagatctggtgttagtttctagtttgtgcgatcgaatttgtcgattaa</u>
<u>tctgagttttt ctgattaacag</u>gt

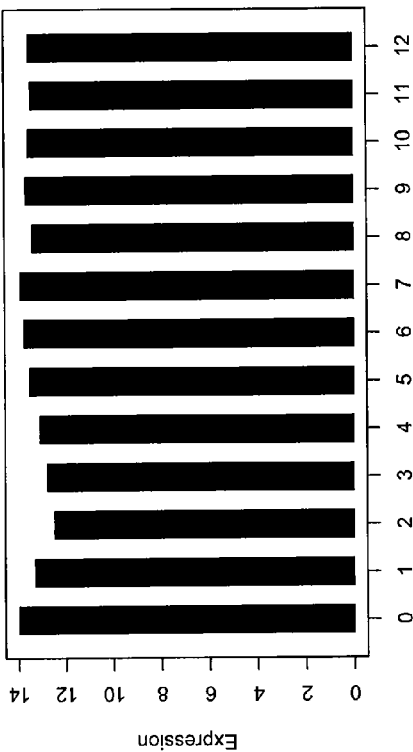
Fig. 32(C) Root developmental zones
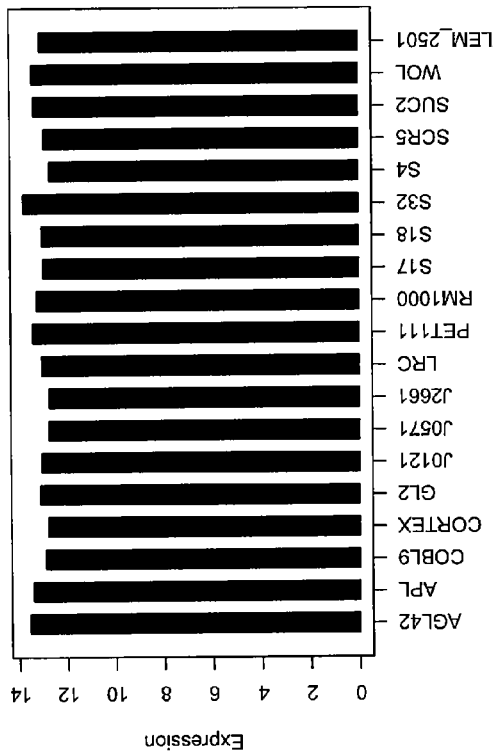
Fig. 32 (B) Root tissue markers
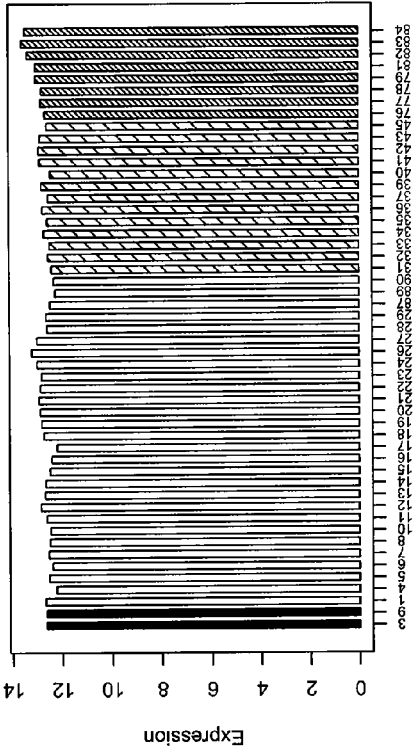
Fig. 32(D) Roots, shoots, flowers, seeds

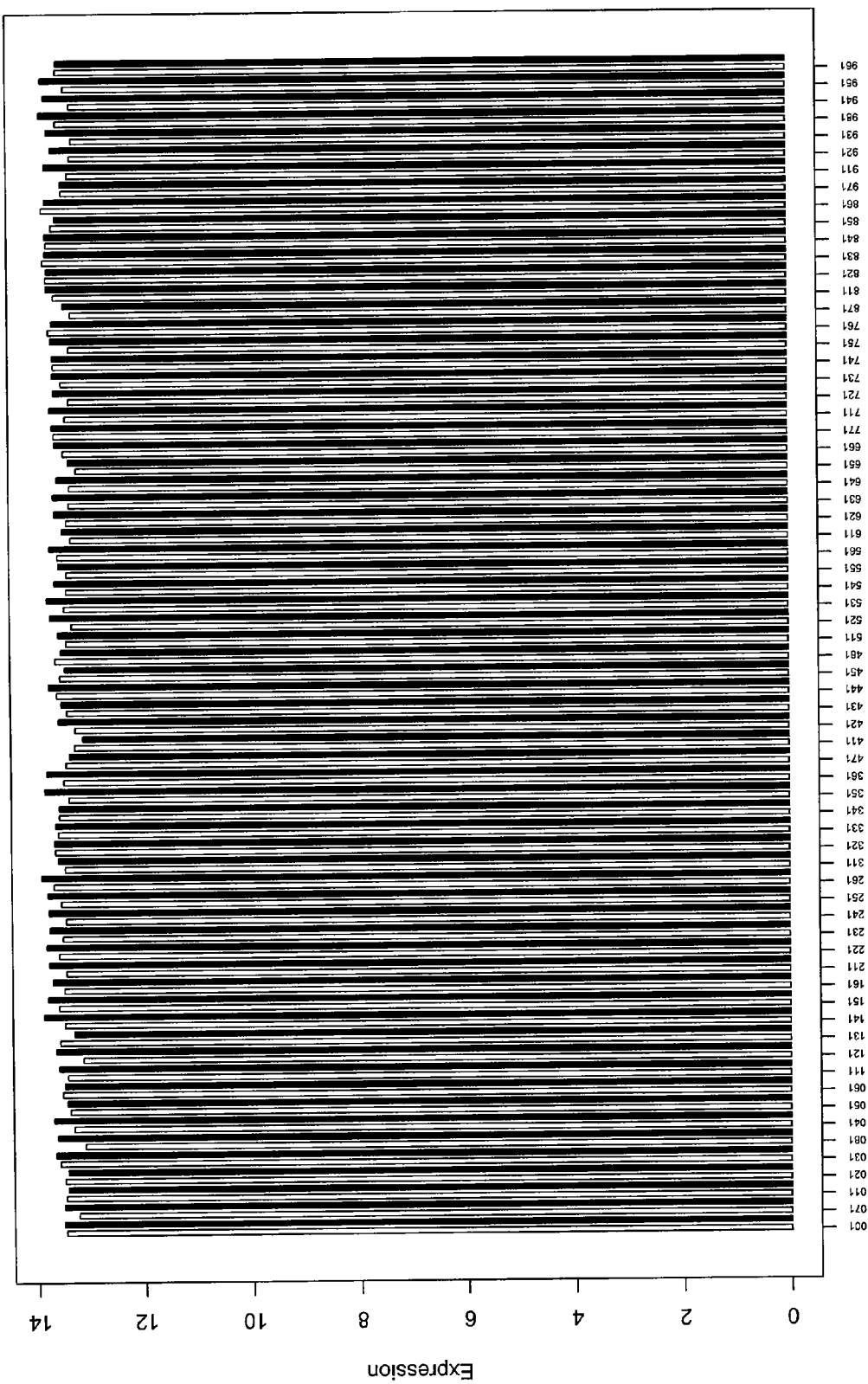
Fig. 32 (E) Abiotic stresses

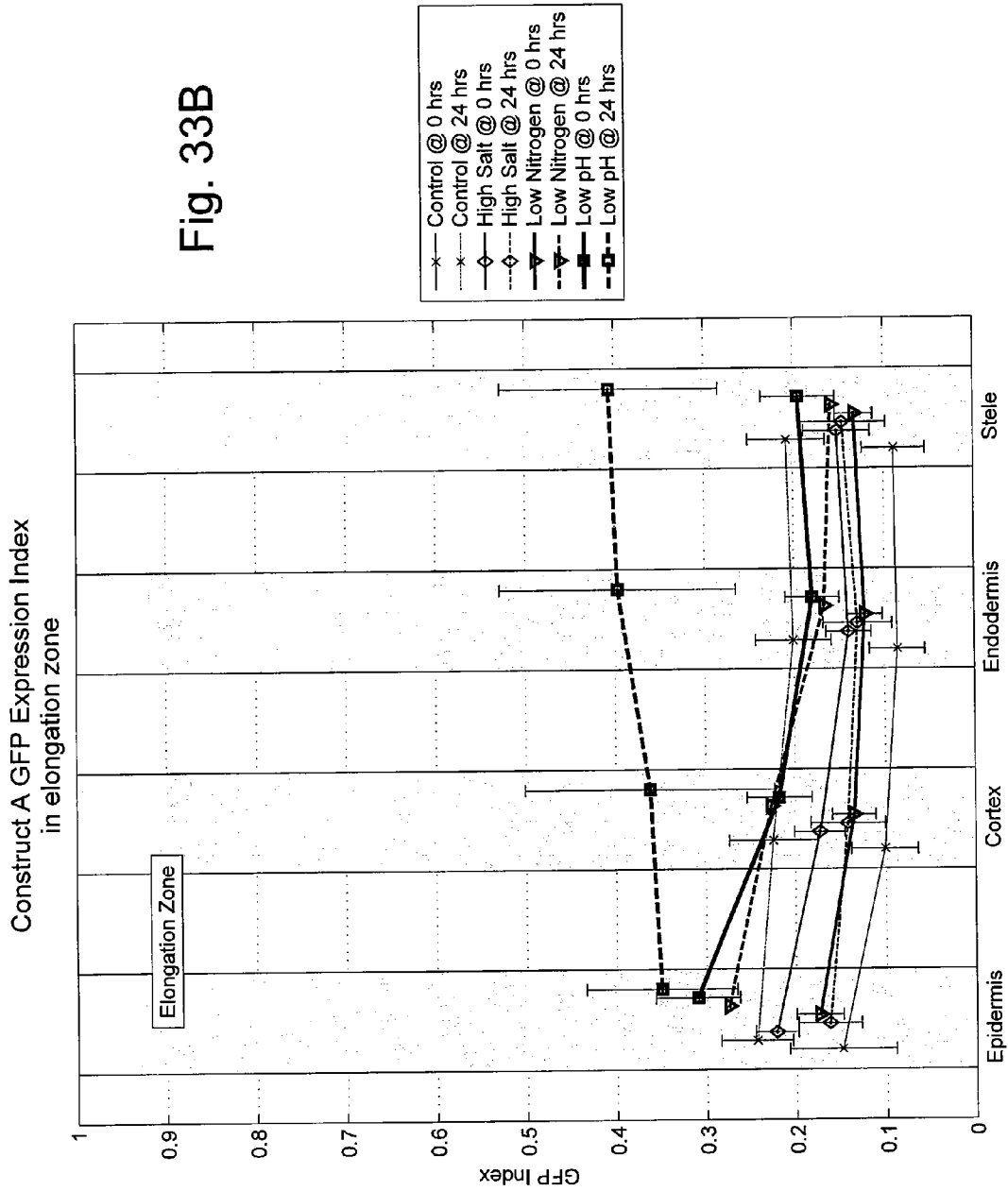

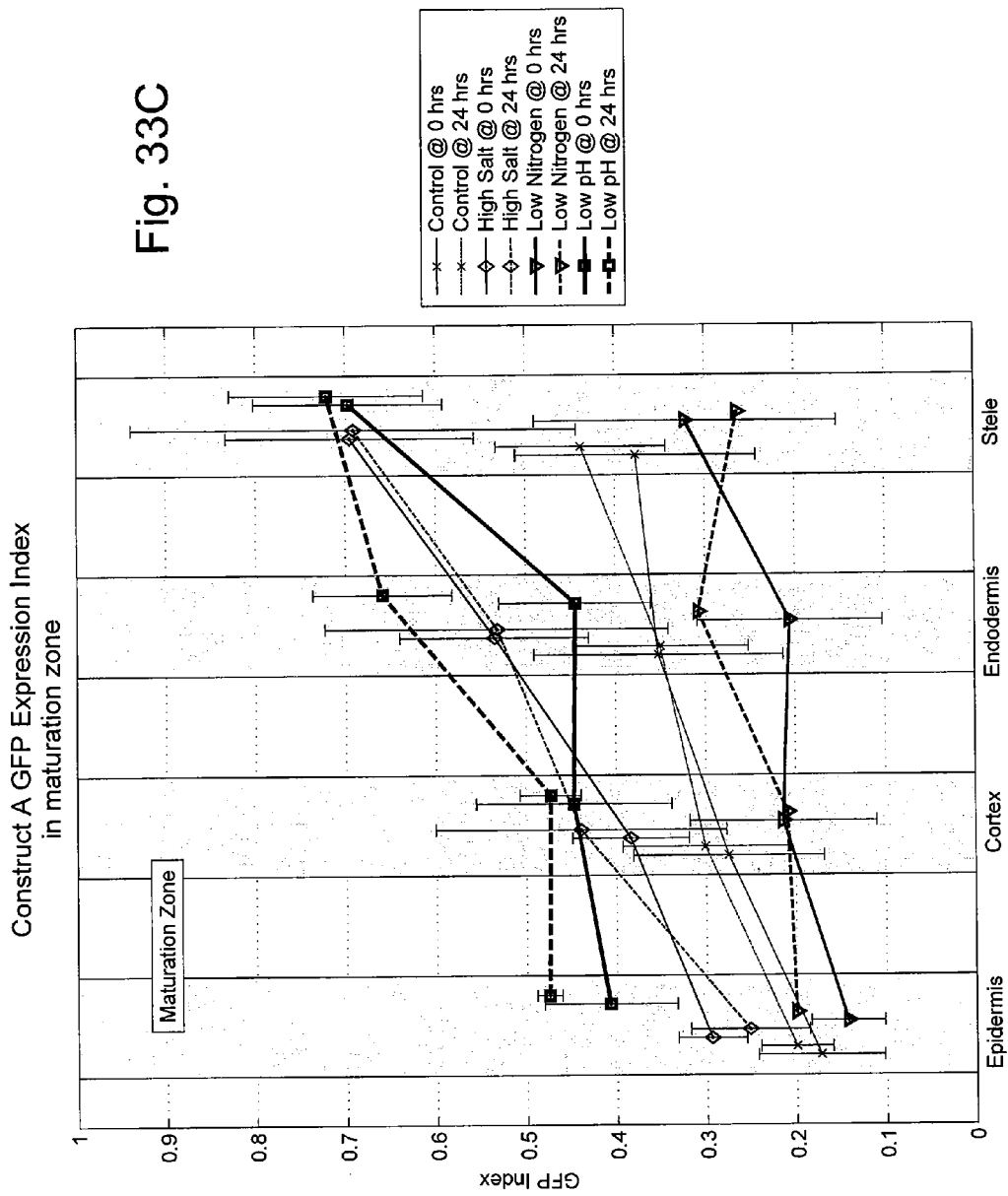

Fig. 34
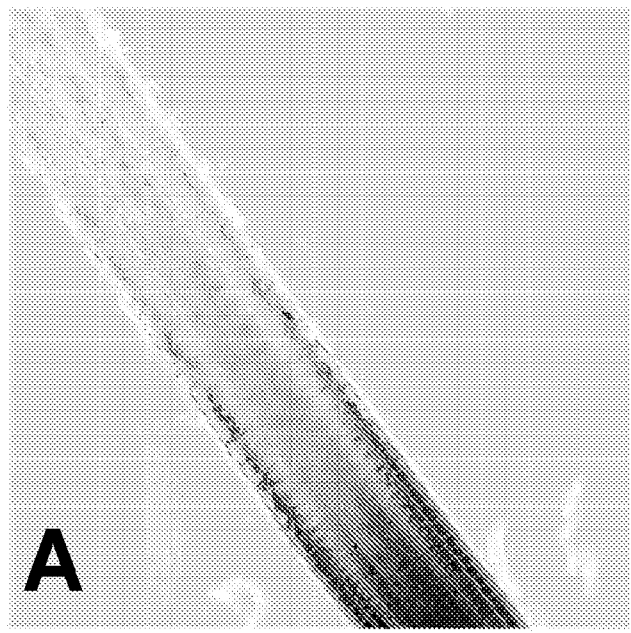
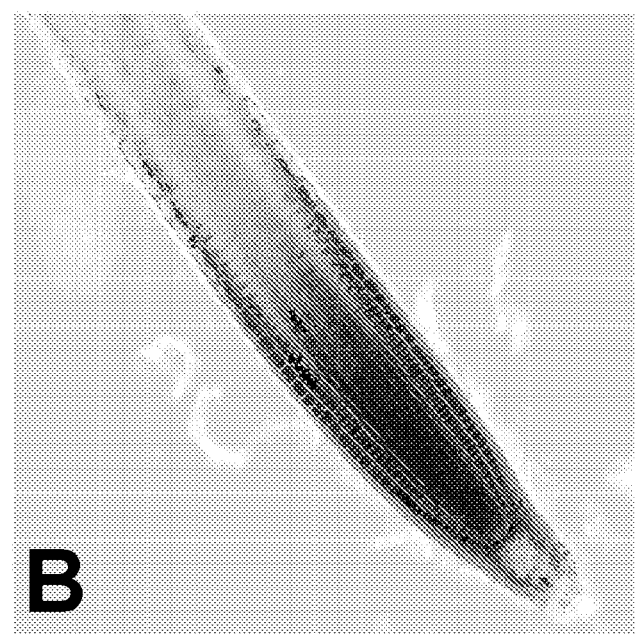

Fig. 35
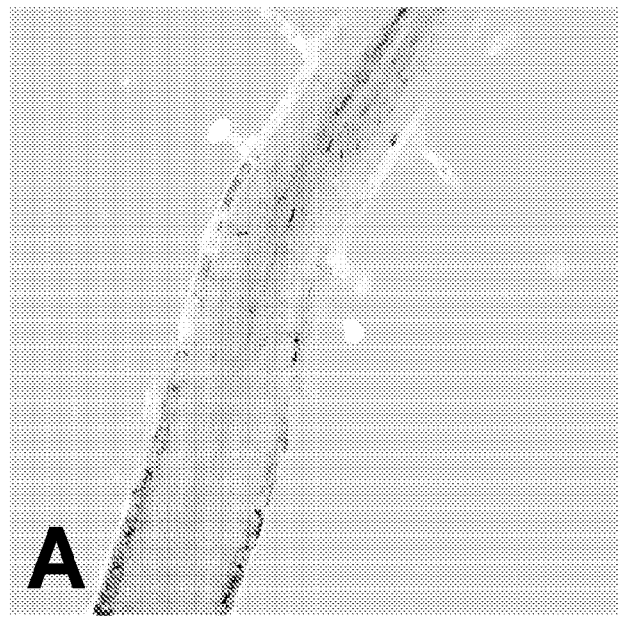
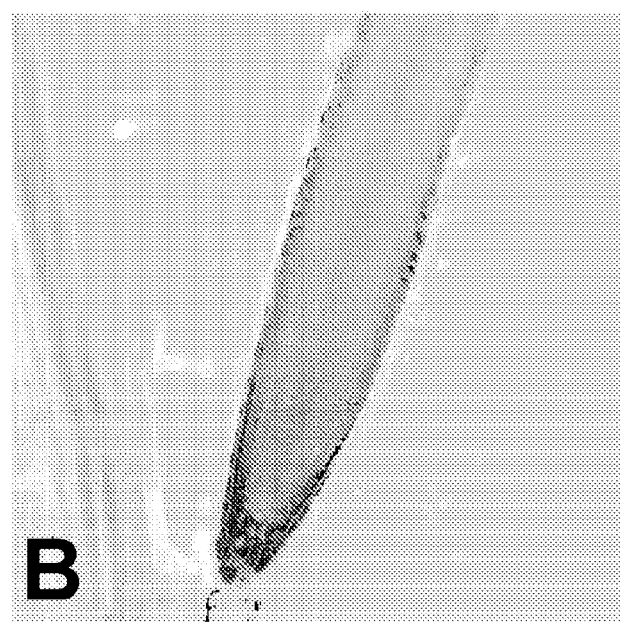

Fig. 36
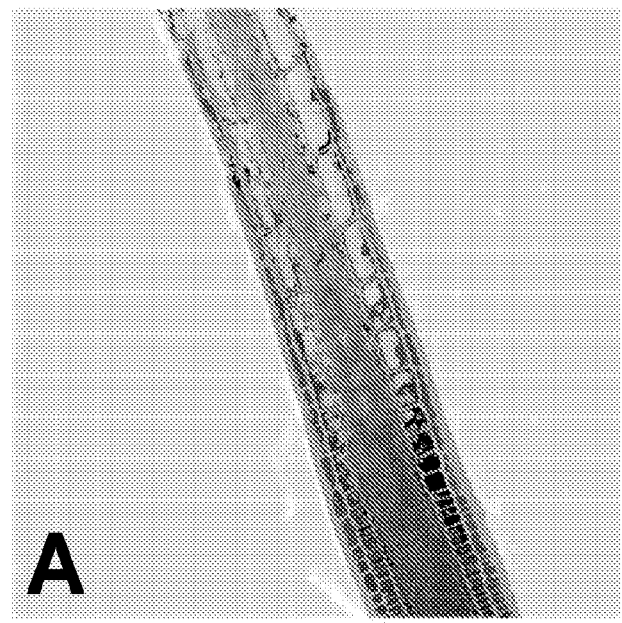
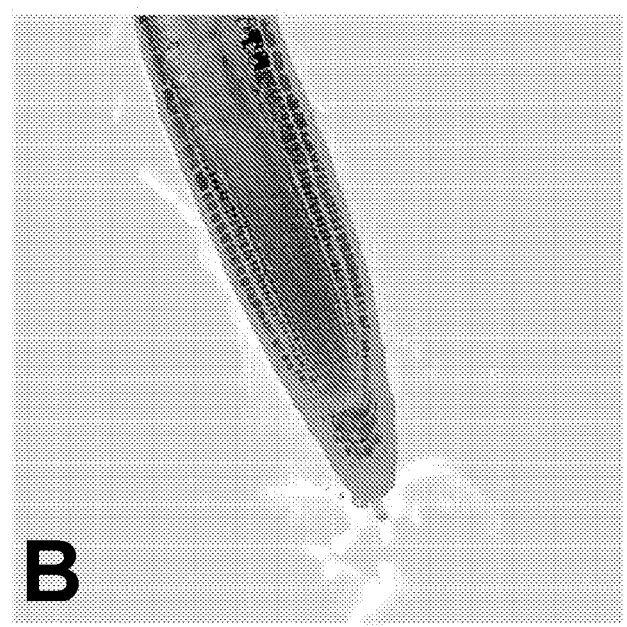

Fig. 37
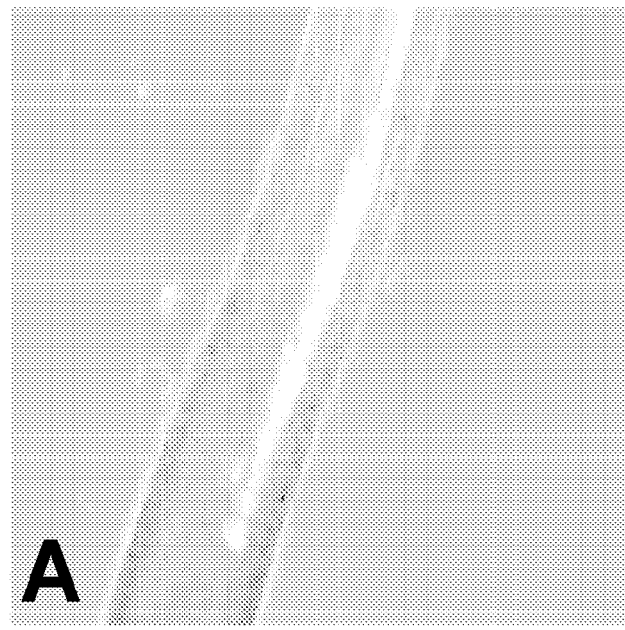
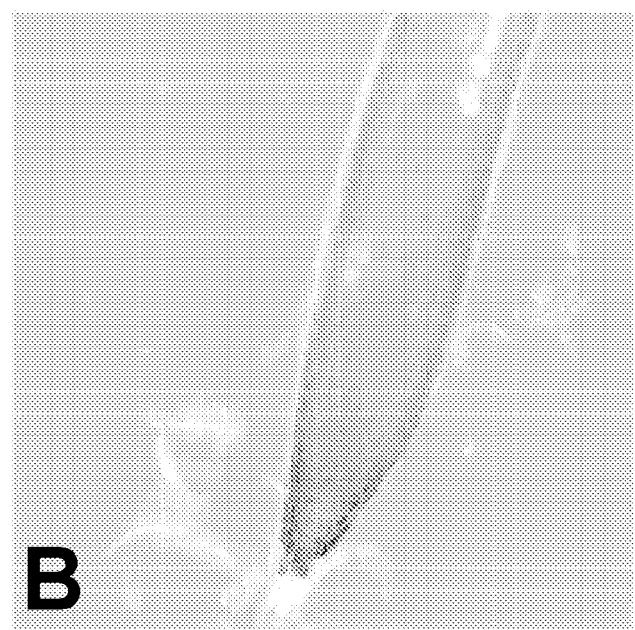

Fig. 38
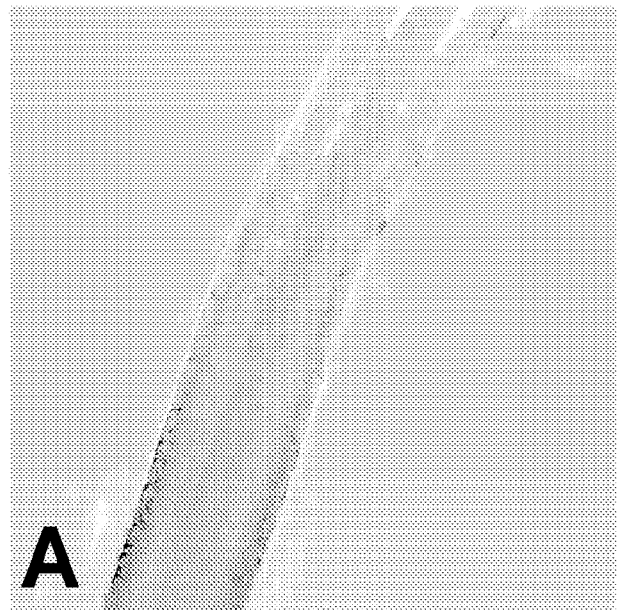
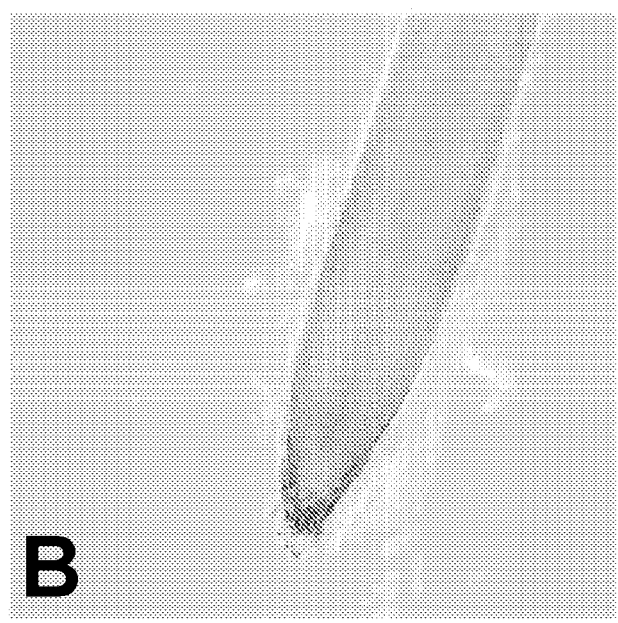

Fig. 39
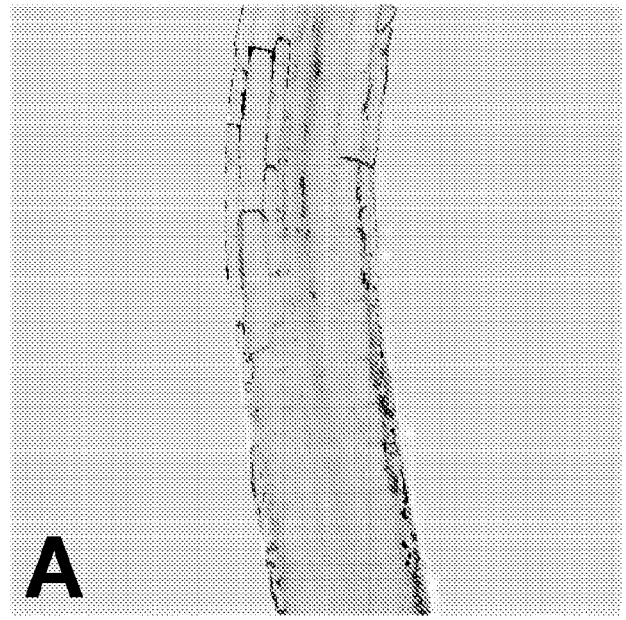
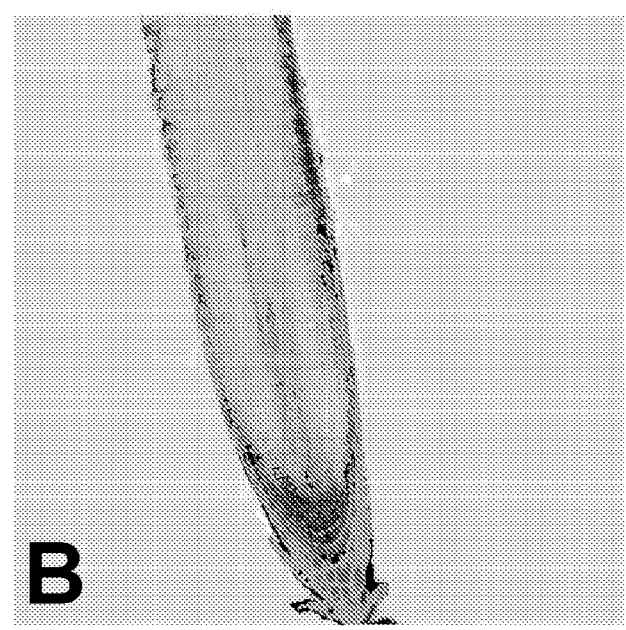

REGULATORY POLYNUCLEOTIDES AND USES THEREOF

This application is a §371 national phase application of International Application Serial No. PCT/US2011/043197, filed Jul. 7, 2011, designating the United States and published in English, which claims the benefit of U.S. Provisional Application No. 61/362,959, filed Jul. 9, 2010, the entire contents of which are hereby incorporated herein by reference.

FEDERALLY SPONSORED RESEARCH OR DEVELOPMENT

This invention was made with Government support under Contract No. 0810649, awarded by the National Science Foundation, STTR. The Government has certain rights in this invention

REFERENCE TO SEQUENCE LISTING SUBMITTED VIA EFS-WEB

This application is being filed electronically via EFS-Web and includes an electronically submitted Sequence Listing in .txt format. The .txt file contains a sequence listing entitled "1390416.txt" created on Jul. 5, 2011 and is 34,031 bytes in size. The sequence listing contained in this .txt file is part of the specification and is hereby incorporated by reference herein in its entirety.

FIELD

The present invention relates to polynucleotide molecules for regulating expression of transcribable polynucleotides in cells (including plant tissues and plants) and uses thereof.

BACKGROUND

The development of transgenic plants having agronomically desirable characteristics often depends on the ability to control the spatial and temporal expression of the polynucleotide responsible for the desired trait. The control of the expression is largely dependent on the availability and use of regulatory control sequences that are responsible for the expression of the operably linked polynucleotide. Where expression in specific tissues or organs is desired, tissue-preferred regulatory elements may be used. Where expression in response to a stimulus is desired, inducible regulatory polynucleotides are the regulatory element of choice. In contrast, where continuous expression is desired throughout the cells of a plant, constitutive regulatory polynucleotides are utilized.

The proper regulatory elements typically must be present and be in the proper location with respect to the polynucleotide in order to obtain expression of the newly inserted transcribable polynucleotide in the plant cell. These regulatory elements may include a promoter region, various cis-elements, regulatory introns, a 5'non-translated leader sequence and a 3' transcription termination/polyadenylation sequence.

Since the patterns of expression of transcribable polynucleotides introduced into a plant are controlled using regulatory elements, there is an ongoing interest in the isolation and identification of novel regulatory elements which are capable of controlling expression of such transcribable polynucleotides.

SUMMARY

In one aspect, an isolated regulatory polynucleotide is provided that comprises a polynucleotide molecule selected from the group consisting of: (a) a polynucleotide molecule comprising a nucleic acid molecule having a sequence selected from the group consisting of SEQ ID NOS: 1-22 that is capable of regulating transcription of an operably linked transcribable polynucleotide molecule; (b) a polynucleotide molecule having at least about 70% sequence identity to a sequence selected from the group consisting of SEQ ID NOS:1-22 that is capable of regulating transcription of an operably linked transcribable polynucleotide molecule; and (c) a fragment of the polynucleotide molecule of (a) or (b) capable of regulating transcription of an operably linked transcribable polynucleotide molecule. In some aspects, the isolated regulatory polynucleotide is capable of regulating constitutive transcription. The isolated regulatory polynucleotide may comprise an intron.

In another aspect, a recombinant polynucleotide construct is provided comprising a regulatory polynucleotide described herein operably linked to a heterologous transcribable polynucleotide molecule. The transcribable polynucleotide molecule may encode a protein of agronomic interest.

In other aspects, such a recombinant polynucleotide construct is used to provide a transgenic host cell comprising the recombinant polynucleotide construct and to provide a transgenic plant stably transformed with the recombinant polynucleotide construct. Seed produced by such transgenic plants are also provided.

In a further aspect, a chimeric polynucleotide molecule is provided that comprises:
(1) a first polynucleotide molecule selected from the group consisting of
  (a) a polynucleotide molecule comprising a nucleic acid molecule having a sequence selected from the group consisting of SEQ ID NOS: 1-22 that is capable of regulating transcription of an operably linked transcribable polynucleotide molecule;
  (b) a polynucleotide molecule having at least about 70% sequence identity to a sequence selected from the group consisting of SEQ ID NOS:1-22 that is capable of regulating transcription of an operably linked transcribable polynucleotide molecule; and
  (c) a fragment of the polynucleotide molecule of (a) or (b) capable of regulating transcription of an operably linked transcribable polynucleotide molecule, and
(2) a second polynucleotide molecule capable of regulating transcription of an operably linked polynucleotide molecule, wherein the first polynucleotide molecule is operably linked to the second polynucleotide molecule.

In yet a further aspect, an isolated polynucleotide molecule is provided that comprises a regulatory element derived from SEQ ID NOS: 1-22, wherein the regulatory element is capable of regulating transcription of an operably linked transcribable polynucleotide molecule.

In another aspect, a method of directing expression of a transcribable polynucleotide molecule in a host cell is provided that comprises:
  (a) introducing the recombinant nucleic acid construct described herein into a host cell to produce a transgenic host cell; and
  (b) selecting a transgenic host cell exhibiting expression of the transcribable polynucleotide molecule.

In a further aspect, a method of directing expression of a transcribable polynucleotide molecule in a plant is provided that comprises:

(a) introducing the recombinant nucleic acid construct described herein into a plant cell;

(b) regenerating a plant from the plant cell; and (c) selecting a transgenic plant exhibiting expression of the transcribable polynucleotide molecule.

BRIEF DESCRIPTION OF THE DRAWINGS

FIGS. 1-22 each provide the nucleotide sequence of a regulatory polynucleotide corresponding to the *Arabidopsis* gene having the accession number specified in the Figure. Where the regulatory polynucleotide has been modified to include the first intron from the coding sequence of the specified gene attached at the 3' end of the 5' UTR, the Figure indicates the gene accession number followed by the indicia "+first intron". Where the regulatory polynucleotide has been modified to include all of, or a portion of, a 35S-minimal promoter, the Figures indicate the gene accession number followed by the indicia "+35S minimal promoter". The figures are annotated to indicate one transcription start site (capital letter in bold), the endogenous 5'-UTR intron sequences (double underlining), the first intron from the coding sequence (single underlining), the 35S -minimal promoter from base −46 to base −1 as measured from the transcription start site (dashed underlining), and any added intron splice sequences (bold italics).

FIG. 1 provides the nucleotide sequence of a regulatory polynucleotide corresponding to the *Arabidopsis* gene having the accession number AT1G13440, +first intron.

FIG. 2 provides the nucleotide sequence of a regulatory polynucleotide corresponding to the *Arabidopsis* gene having the accession number AT1G13440.

FIG. 3 provides the nucleotide sequence of a regulatory polynucleotide corresponding to the *Arabidopsis* gene having the accession number AT1G22840, +first intron.

FIG. 4 provides the nucleotide sequence of a regulatory polynucleotide corresponding to the *Arabidopsis* gene having the accession number AT1G22840.

FIG. 5 provides the nucleotide sequence of a regulatory polynucleotide corresponding to the *Arabidopsis* gene having the accession number AT1G22840, +first intron, +35S minimal promoter.

FIG. 6 provides the nucleotide sequence of a regulatory polynucleotide corresponding to the *Arabidopsis* gene having the accession number AT1G52300, +first intron.

FIG. 7 provides the nucleotide sequence of a regulatory polynucleotide corresponding to the *Arabidopsis* gene having the accession number AT1G52300.

FIG. 8 provides the nucleotide sequence of a regulatory polynucleotide corresponding to the *Arabidopsis* gene having the accession number AT1G52300, +first intron, +35S minimal promoter.

FIG. 9 provides the nucleotide sequence of a regulatory polynucleotide corresponding to the *Arabidopsis* gene having the accession number AT4G37830, +first intron.

FIG. 10 provides the nucleotide sequence of a regulatory polynucleotide corresponding to the *Arabidopsis* gene having the accession number AT4G37830.

FIG. 11 provides the nucleotide sequence of a regulatory polynucleotide corresponding to the *Arabidopsis* gene having the accession number AT4G37830, +first intron, +35S minimal promoter.

FIG. 12 provides the nucleotide sequence of a regulatory polynucleotide corresponding to the *Arabidopsis* gene having the accession number AT3G08580.

FIG. 13 provides the nucleotide sequence of a regulatory polynucleotide corresponding to the *Arabidopsis* gene having the accession number AT3G08580, +35s minimal promoter.

FIG. 14 provides the nucleotide sequence of a regulatory polynucleotide corresponding to the *Arabidopsis* gene having the accession number AT1G51650, +first intron.

FIG. 15 provides the nucleotide sequence of a regulatory polynucleotide corresponding to the *Arabidopsis* gene having the accession number AT1G51650.

FIG. 16 provides the nucleotide sequence of a regulatory polynucleotide corresponding to the *Arabidopsis* gene having the accession number AT1G51650, +first intron, +35S minimal promoter.

FIG. 17 provides the nucleotide sequence of a regulatory polynucleotide corresponding to the *Arabidopsis* gene having the accession number AT3G48140, +first intron.

FIG. 18 provides the nucleotide sequence of a regulatory polynucleotide corresponding to the *Arabidopsis* gene having the accession number AT3G48140.

FIG. 19 provides the nucleotide sequence of a regulatory polynucleotide corresponding to the *Arabidopsis* gene having the accession number AT3G48140, +first intron, +35S minimal promoter.

FIG. 20 provides the nucleotide sequence of a regulatory polynucleotide corresponding to the *Arabidopsis* gene having the accession number AT3G08610, +first intron.

FIG. 21 provides the nucleotide sequence of a regulatory polynucleotide corresponding to the *Arabidopsis* gene having the accession number AT3G08610.

FIG. 22 provides the nucleotide sequence of a regulatory polynucleotide corresponding to the *Arabidopsis* gene having the accession number AT3G62250.

FIGS. 23A-D through 31A-D illustrate the expression data of the underlying *Arabidopsis* genes that correspond to the regulatory polynucleotides of FIGS. 1-22.

FIGS. 23A-23D provide a schematic representation of the endogenous expression data for the *Arabidopsis* gene having the accession number AT1G13440. FIG. 23A provides the expression values of this gene in different cell types which were sorted on the basis of expressing the indicated GFP markers. FIG. 23B provides the expression values of this gene from root sections along the longitudinal axis of the root. FIG. 23C provides the developmental specific expression of the gene. FIG. 23D provides the expression of the gene in response to various abiotic stresses.

FIGS. 24A-D provide a schematic representation of the endogenous expression data for the *Arabidopsis* gene having the accession number AT1G22840. FIG. 24A provides the expression values of this gene in different cell types which were sorted on the basis of expressing the indicated GFP markers. FIG. 24B provides the expression values of this gene from root sections along the longitudinal axis of the root. FIG. 24C provides the developmental specific expression of the gene. FIG. 24D provides the expression of the gene in response to various abiotic stresses.

FIGS. 25A-D provide a schematic representation of the endogenous expression data for the *Arabidopsis* gene having the accession number AT1G52300. FIG. 25A provides the expression values of this gene in different cell types which were sorted on the basis of expressing the indicated GFP markers. FIG. 25B provides the expression values of this gene from root sections along the longitudinal axis of the root. FIG. 25C provides the developmental specific expression of the gene. FIG. 25D provides the expression of the gene in response to various abiotic stresses.

FIGS. 26A-D provide a schematic representation of the endogenous expression data for the *Arabidopsis* gene having the accession number AT4G37830. FIG. 26A provides the expression values of this gene in different cell types which were sorted on the basis of expressing the indicated GFP markers. FIG. 26B provides the expression values of this gene from root sections along the longitudinal axis of the root. FIG. 26C provides the developmental specific expression of the gene. FIG. 26D provides the expression of the gene in response to various abiotic stresses.

FIGS. 27A-D provide a schematic representation of the endogenous expression data for the *Arabidopsis* gene having the accession number AT3G08580. FIG. 27A provides the expression values of this gene in different cell types which were sorted on the basis of expressing the indicated GFP markers. FIG. 27B provides the expression values of this gene from root sections along the longitudinal axis of the root. FIG. 27C provides the developmental specific expression of the gene. FIG. 27D provides the expression of the gene in response to various abiotic stresses.

FIGS. 28A-D provide a schematic representation of the endogenous expression data for the *Arabidopsis* gene having the accession number AT1G51650. FIG. 28A provides the expression values of this gene in different cell types which were sorted on the basis of expressing the indicated GFP markers. FIG. 28B provides the expression values of this gene from root sections along the longitudinal axis of the root. FIG. 28C provides the developmental specific expression of the gene. FIG. 28D provides the expression of the gene in response to various abiotic stresses.

FIGS. 29A-D provide a schematic representation of the endogenous expression data for the *Arabidopsis* gene having the accession number AT3G48140. FIG. 29A provides the expression values of this gene in different cell types which were sorted on the basis of expressing the indicated GFP markers. FIG. 29B provides the expression values of this gene from root sections along the longitudinal axis of the root. FIG. 29C provides the developmental specific expression of the gene. FIG. 289D provides the expression of the gene in response to various abiotic stresses.

FIGS. 30A-D provide a schematic representation of the endogenous expression data for the *Arabidopsis* gene having the accession number AT3G08610. FIG. 30A provides the expression values of this gene in different cell types which were sorted on the basis of expressing the indicated GFP markers. FIG. 30B provides the expression values of this gene from root sections along the longitudinal axis of the root. FIG. 30C provides the developmental specific expression of the gene. FIG. 30D provides the expression of the gene in response to various abiotic stresses.

FIGS. 31A-D provide a schematic representation of the endogenous expression data for the *Arabidopsis* gene having the accession number AT3G62250. FIG. 31A provides the expression values of this gene in different cell types which were sorted on the basis of expressing the indicated GFP markers. FIG. 31B provides the expression values of this gene from root sections along the longitudinal axis of the root. FIG. 31C provides the developmental specific expression of the gene. FIG. 31D provides the expression of the gene in response to various abiotic stresses.

FIG. 32A provides the nucleotide sequence of the regulatory polynucleotide of the *Arabidopsis* gene having Accession No. AT4G05320. FIGS. 32B-32E provide a schematic representation of the endogenous expression data for the *Arabidopsis* gene having Accession No. AT4G05320. FIG. 32B provides the expression values of this gene in different cell types which were sorted on the basis of expressing the indicated GFP markers. FIG. 32C provides the expression values of this gene from root sections along the longitudinal axis of the root. FIG. 32D provides the developmental specific expression of AT4G05320. FIG. 32E provides the expression of AT4G05320in response to various abiotic stresses.

FIGS. 33A, 33B, and 33C show average GFP Expression Index in different cell-types in 3 longitudinal zones under standard and 3 stress conditions using a regulatory polynucleotide from the *Arabidopsis* polyubiquitin gene UBQ10, which was identified using the methods described herein.

FIG. 34 provides representative images of GFP expression of *Arabidopsis* plants according to Example 4. As explained in Example 4, FIG. 34A shows GFP expression in the elongation zone and FIG. 34B shows GFP expression in the meristematic zone.

FIG. 35 provides representative images of GFP expression of *Arabidopsis* plants according to Example 4. As explained in Example 4, FIG. 35A shows GFP expression in the elongation zone and FIG. 35B shows GFP expression in the meristematic zone.

FIG. 36 provides representative images of GFP expression of *Arabidopsis* plants according to Example 4. As explained in Example 4, FIG. 36A shows GFP expression in the elongation zone and FIG. 36B shows GFP expression in the meristematic zone.

FIG. 37 provides representative images of GFP expression of *Arabidopsis* plants according to Example 4. As explained in Example 4, FIG. 37A shows GFP expression in the elongation zone and FIG. 37B shows GFP expression in the meristematic zone.

FIG. 38 provides representative images of GFP expression of *Arabidopsis* plants according to Example 4. As explained in Example 4, FIG. 38A shows GFP expression in the elongation zone and FIG. 38B shows GFP expression in the meristematic zone.

FIG. 39A shows GFP expression of construct A in the elongation zone and FIG. 39B shows GFP expression of construct A in the meristematic zone according to Example 8.

DETAILED DESCRIPTION

Figure 33A:
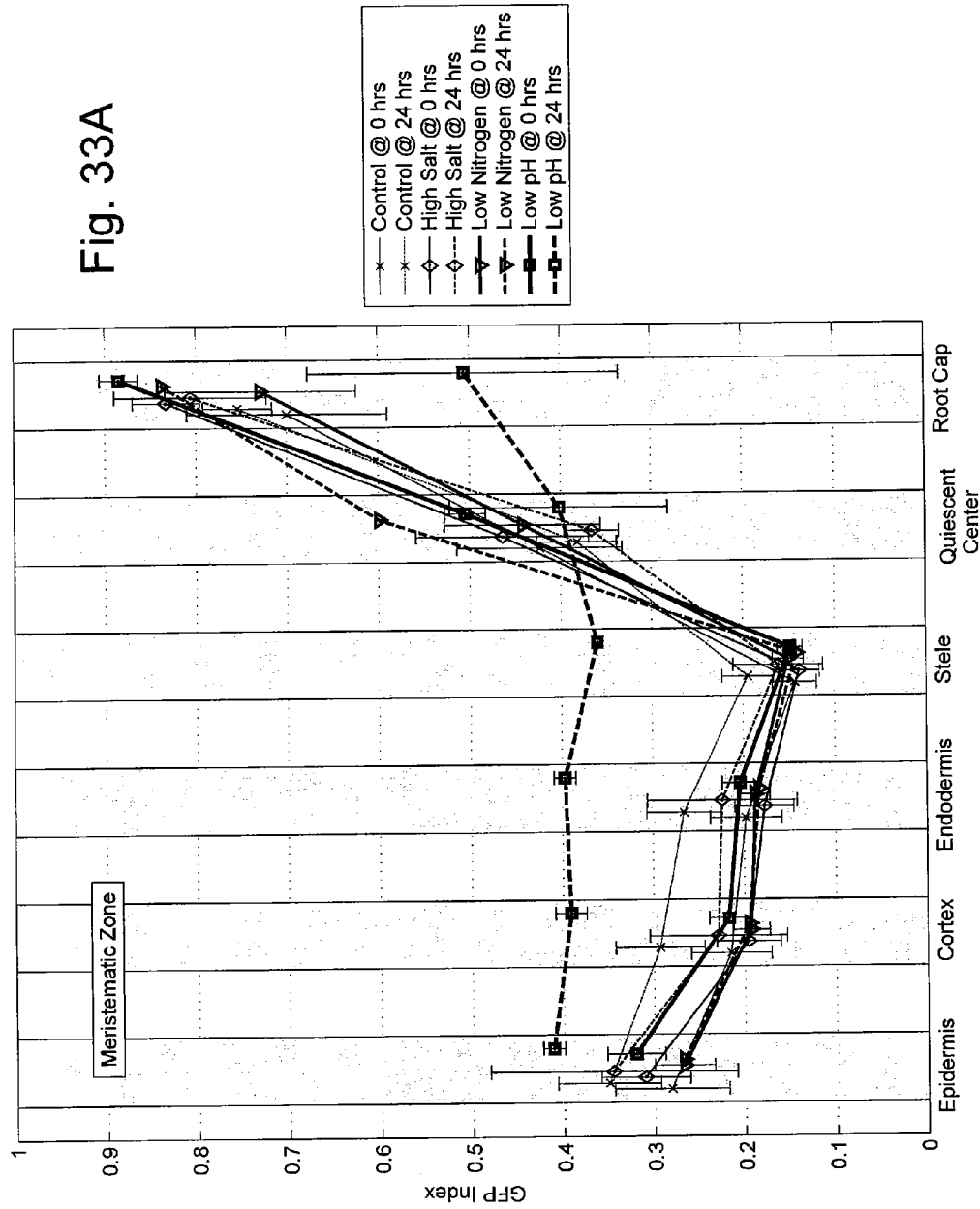

The present disclosure relates to regulatory polynucleotides that are capable of regulating expression of a transcribable polynucleotide in a host cell. In some embodiments, the regulatory polynucleotides are capable of regulating expression of a transcribable polynucleotide in a plant cell, plant tissue, plant, or plant seed. In other embodiments, the regulatory polynucleotides are capable of providing for constitutive expression of an operably linked polynucleotide in plants and plant tissues.

The present disclosure also provides recombinant constructs comprising such regulatory polynucleotides, as well as transgenic host cells, and organisms containing such recombinant constructs. Also provided are methods of directing expression of a transcribable polynucleotide in a host cell or organism.

Prior to describing this invention in further detail, however, the following terms will first be defined.

Definitions:

As used herein, the phrase "polynucleotide molecule" refers to a single- or double-stranded DNA or RNA of any origin (e.g., genomic or synthetic origin), i.e., a polymer of deoxyribonucleotide or ribonucleotide bases, respectively, read from the 5' (upstream) end to the 3' (downstream) end.

As used herein, the phrase "polynucleotide sequence" refers to the sequence of a polynucleotide molecule. The nomenclature for DNA bases as set forth at 37 CFR §1.822 is used.

As used herein, the term "transcribable polynucleotide molecule" refers to any polynucleotide molecule capable of being transcribed into a RNA molecule including, but not limited to, protein coding sequences (e.g., transgenes) and functional RNA sequences (e.g., a molecule useful for gene suppression).

As used herein, the terms "regulatory element" and "regulatory polynucleotide" refer to polynucleotide molecules having regulatory activity (i.e., one that has the ability to affect the transcription of an operably linked transcribable polynucleotide molecule). The terms refer to a polynucleotide molecule containing one or more elements such as core promoter regions, cis-elements, leaders or UTRs, enhancers, introns, and transcription termination regions, all of which have regulatory activity and may play a role in the overall expression of nucleic acid molecules in living cells. The "regulatory elements" determine if, when, and at what level a particular polynucleotide is transcribed. The regulatory elements may interact with regulatory proteins or other proteins or be involved in nucleotide interactions, for example, to provide proper folding of a regulatory polynucleotide.

As used herein, the term "core promoter" and "minimal promoter" refer to a minimal region of a regulatory polynucleotide required to properly initiate transcription. A core promoter typically contains the transcription start site (TSS), a binding site for RNA polymerase, and general transcription factor binding sites. Core promoters can include promoters produced through the manipulation of known core promoters to produce artificial, chimeric, or hybrid promoters, and can be used in combination with other regulatory elements, such as cis-elements, enhancers, or introns, for example, by adding a heterologous regulatory element to an active core promoter with its own partial or complete regulatory elements.

As used herein, the term "cis-element" refers to a cis-acting transcriptional regulatory element that confers an aspect of the overall control of the expression of an operably linked transcribable polynucleotide. A cis-element may function to bind transcription factors, which are trans-acting protein factors that regulate transcription. Some cis-elements bind more than one transcription factor, and transcription factors may interact with different affinities with more than one cis-element. Cis-elements including deletion analysis (i.e., deleting one or more nucleotides from the 5' end or internal to a promoter), DNA binding protein analysis using DNase I footprinting, methylation interference, electrophoresis mobility-shift assays, in vivo genomic footprinting by ligation-mediated PCR, and other conventional assays; or by DNA sequence similarity analysis with known cis-element motifs by conventional DNA sequence comparison methods. The fine structure of a cis-element can be further studied by mutagenesis (or substitution) of one or more nucleotides or by other conventional methods. Cis-elements can be obtained by chemical synthesis or by isolation from regulatory polynucleotides that include such elements, and they can be synthesized with additional flanking nucleotides that contain useful restriction enzyme sites to facilitate subsequence manipulation.

As used herein, the term "enhancer" refers to a transcriptional regulatory element, typically 100-200 base pairs in length, which strongly activates transcription, for example, through the binding of one or more transcription factors. Enhancers can be identified and studied by methods such as those described above for cis-elements. Enhancer sequences can be obtained by chemical synthesis or by isolation from regulatory elements that include such elements, and they can be synthesized with additional flanking nucleotides that contain useful restriction enzyme sites to facilitate subsequence manipulation.

As used herein, the term "intron" refers to a polynucleotide molecule that may be isolated or identified from the intervening sequence of a genomic copy of a transcribed polynucleotide which is spliced out during mRNA processing prior to translation. Introns may themselves contain sub-elements such as cis-elements or enhancer domains that affect the transcription of operably linked polynucleotide molecules. Some introns are capable of increasing gene expression through a mechanism known as intron mediated enhancement (IME). IME, as distinguished from the effects of enhancers, is based on introns residing in the transcribed region of a polynucleotide. In general, IME is mediated by the first intron of a gene, which can reside in either the 5'-UTR sequence of a gene or between the first and second protein coding (CDS) exons of a gene. Without being limited by theory, IME may be particularly important in highly expressed, constitutive genes.

As used herein, the terms "leader" or "5'-UTR" refer to a polynucleotide sequence between the transcription and translation start sites of a gene. 5'-UTRs may themselves contain sub-elements such as cis-elements, enhancer domains, or introns that affect the transcription of operably linked polynucleotide molecules.

As used herein, the term "ortholog" refers to a polynucleotide from a different species that encodes a similar protein that performs the same biological function. For example, the ubiquitin genes from, for example, *Arabidopsis* and rice, are orthologs. Orthologs may also exhibit similar tissue expression patterns (for example, constitutive expression in plant cells or plant tissues). Typically, orthologous nucleotide sequences are characterized by significant sequence similarity. A nucleotide sequence of an ortholog in one species (for example, *Arabidopsis*) can be used to isolate the nucleotide sequence of the ortholog in another species (for example, rice) using standard molecular biology techniques.

The term "expression" or "gene expression" means the transcription of an operably linked polynucleotide. The term "expression" or "gene expression" in particular refers to the transcription of an operably linked polynucleotide into structural RNA (rRNA, tRNA) or mRNA with or without subsequent translation of the latter into a protein. The process includes transcription of DNA and processing of the resulting mRNA product.

"Constitutive expression" refers to the transcription of a polynucleotide in all or substantially all tissues and stages of development and being minimally responsive to abiotic stimuli. "Constitutive plant regulatory polynucleotides" are regulatory polynucleotides that have regulatory activity in all or substantially all tissues of a plant throughout plant development. It is understood that for the terms "constitutive expression" and "constitutive plant regulatory polynucleotide" that some variation in absolute levels of expression or activity can exist among different plant tissues and stages of development.

As used herein, the term "chimeric" refers to the product of the fusion of portions of two or more different polynucleotide molecules. As used herein, the term "chimeric regulatory polynucleotide" refers to a regulatory polynucleotide produced through the manipulation of known promoters or other polynucleotide molecules, such as cis-elements. Such chimeric regulatory polynucleotides may combine enhancer domains that can confer or modulate expression from one or more regulatory polynucleotides, for example, by fusing a heterologous enhancer domain from a first regulatory polynucleotide to a promoter element (e.g. a core promoter) from a second regulatory polynucleotide with its own partial or complete regulatory elements.

As used herein, the term "operably linked" refers to a first polynucleotide molecule, such as a core promoter, connected with a second polynucleotide molecule, such as a transcribable polynucleotide (e.g., a polynucleotide encoding a protein of interest), where the polynucleotide molecules are so arranged that the first polynucleotide molecule affects the transcription of the second polynucleotide molecule. The two polynucleotide molecules may be part of a single contiguous polynucleotide molecule and may be adjacent. For example, a promoter is operably linked to a polynucleotide encoding a protein of interest if the promoter modulates transcription of the polynucleotide of interest in a cell.

An "isolated" or "purified" polynucleotide or polypeptide molecule, refers to a molecule that is not in its native environment such as, for example, a molecule not normally found in the genome of a particular host cell, or a DNA not normally found in the host genome in an identical context, or any two sequences adjacent to each other that are not normally or naturally adjacent to each other.

Regulatory Polynucleotide Molecules

The regulatory polynucleotide molecules described herein were discovered using bioinformatic screening techniques of databases containing expression and sequence data for genes in various plant species. Such bioinformatic techniques are described in more detail in the Examples set forth below.

In one embodiment, isolated regulatory polynucleotide molecules are provided. The regulatory polynucleotides provided herein include polynucleotide molecules having transcription regulatory activity in host cells, such as plant cells. In some embodiments, the regulatory polynucleotides are capable of regulating constitutive transcription of an operably linked transcribable polynucleotide molecule in transgenic plants and plant tissues.

The isolated regulatory polynucleotide molecules comprise a polynucleotide molecule selected from the group consisting of a) a polynucleotide molecule comprising a nucleic acid molecule having a sequence selected from the group consisting of SEQ ID NOs: 1-22 that is capable of regulating transcription of an operably linked transcribable polynucleotide molecule; b) a polynucleotide molecule having at least about 70% sequence identity to the sequence of SEQ ID NOs:1-22 that is capable of regulating transcription of an operably linked transcribable polynucleotide molecule; and c) a fragment of the polynucleotide molecule of a) or b) capable of regulating transcription of an operably linked transcribable polynucleotide molecule. Such fragments can be a UTR, a core promoter, an intron, an enhancer, a cis-element, or any other regulatory element.

Thus, the regulatory polynucleotide molecules include those molecules having sequences provided in SEQ ID NO: 1 through SEQ ID NO: 22. These polynucleotide molecules are capable of affecting the expression of an operably linked transcribable polynucleotide molecule in plant cells and plant tissues and therefore can regulate expression in transgenic plants. The present disclosure also provides methods of modifying, producing, and using such regulatory polynucleotides. Also included are compositions, transformed host cells, transgenic plants, and seeds containing the regulatory polynucleotides, and methods for preparing and using such regulatory polynucleotides.

The disclosed regulatory polynucleotides are capable of providing for expression of operably linked transcribable polynucleotides in any cell type, including, but not limited to plant cells. For example, the regulatory polynucleotides may be capable of providing for the expression of operably linked heterologous transcribable polynucleotides in plants and plant cells. In one embodiment, the regulatory polynucleotides are capable of directing constitutive expression in a transgenic plant, plant tissue(s), or plant cell(s).

In one embodiment, the regulatory polynucleotides may comprise multiple regulatory elements, each of which confers a different aspect to the overall control of the expression of an operably linked transcribable polynucleotide. In another embodiment, regulatory elements may be derived from the polynucleotide molecules of SEQ ID NOs:1-22. Thus, regulatory elements of the disclosed regulatory polynucleotides are also provided.

The disclosed polynucleotides include, but are not limited to, nucleic acid molecules that are between about 0.1 Kb and about 5 Kb, between about 0.1 Kb and about 4 Kb, between about 0.1 Kb and about 3 Kb, and between about 0.1 Kb and about 2 Kb, about 0.25 Kb and about 2 Kb, or between about 0.10 Kb and about 1.0 Kb.

The regulatory polynucleotides as provided herein also include fragments of SEQ ID NOs: 1-22. The fragment polynucleotides include those polynucleotides that comprise at least 50, at least 75, at least 100, at least 125, at least 150, at least 175, or at least 200 contiguous nucleotide bases where the fragment's complete sequence in its entirety is identical to a contiguous fragment of the referenced polynucleotide molecule. In some embodiments, the fragments contain one or more regulatory elements capable of regulating the transcription of an operably linked polynucleotide. Such fragments may include regulatory elements such as introns, enhancers, core promoters, leaders, and the like.

Thus also provided are regulatory elements derived from the polynucleotides having the sequences of SEQ ID NOs: 1-22. In some embodiments, the regulatory elements are capable of regulating transcription of operably linked transcribable polynucleotides in plants and plant tissues. The regulatory elements that may be derived from the polynucleotides of SEQ ID NOs:1-22 include, but are not limited to introns, enhancers, leaders, and the like. In addition, the regulatory elements may be used in recombinant constructs for the expression of operably linked transcribable polynucleotides of interest.

The present disclosure also includes regulatory polynucleotides that are substantially homologous to SEQ ID NOs:1-22. As used herein, the phrase "substantially homologous" refers to polynucleotide molecules that generally demonstrate a substantial percent sequence identity with the regulatory polynucleotides provided herein. Substantially homologous polynucleotide molecules include polynucleotide molecules that function in plants and plant cells to direct transcription and have at least about 70% sequence identity, at least about 80% sequence identity, at least about 90% sequence identity, or even greater sequence identity, specifically including about 73%, 75%, 78%, 83%, 85%, 88%, 92%, 94%, 95%, 96%, 97%, 98%, 99% or greater sequence identity with the regulatory polynucleotide molecules provided in SEQ ID NOs:1-22. Polynucleotide molecules that are capable of regulating transcription of operably linked transcribable polynucleotide molecules and are substantially homologous to the polynucleotide sequences of the regulatory polynucleotides provided herein are encompassed herein.

As used herein, the "percent sequence identity" is determined by comparing two optimally aligned sequences over a comparison window, where the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, divided by the number of matched positions by the total number of positions in the window of comparison and multiplying the result by 100 to yield the percentage of sequence identity. Alignment for the purposes of determining the percentage identity can be achieved in various ways that are within the skill in the art, for example, using publicly available computer software such as BLAST. Those skilled in the art can determine appropriate parameters for measuring alignment, including any algorithms needed to achieve optimal alignment over the full length of the sequences being compared.

Additional regulatory polynucleotides substantially homologous to those identified herein may be identified by a variety of methods. For example, cDNA libraries may be constructed using cells or tissues of interest and screened to identify genes having an expression pattern similar to that of the regulatory elements described herein. The cDNA sequence for the identified gene may then be used to isolate the gene's regulatory sequences for further characterization. Alternately, transcriptional profiling or electronic northern techniques may be used to identify genes having an expression pattern similar to that of the regulatory polynucleotides described herein. Once these genes have been identified, their regulatory polynucleotides may be isolated for further characterization. The electronic northern technique refers to a computer-based sequence analysis which allows sequences from multiple cDNA libraries to be compared electronically based on parameters the researcher identifies including abundance in EST populations in multiple cDNA libraries, or exclusively to EST sets from one or combinations of libraries. The transcriptional profiling technique is a high-throughput method used for the systematic monitoring of expression profiles for thousands of genes. This DNA chip-based technology arrays thousands of oligonucleotides on a support surface. These arrays are simultaneously hybridized to a population of labeled cDNA or cRNA probes prepared from RNA samples of different cell or tissue types, allowing direct comparative analysis of expression. This approach may be used for the isolation of regulatory sequences such as promoters associated with those sequences.

In some embodiments, substantially homologous polynucleotide molecules may be identified when they specifically hybridize to form a duplex molecule under certain conditions. Under these conditions, referred to as stringency conditions, one polynucleotide molecule can be used as a probe or primer to identify other polynucleotide molecules that share homology. Accordingly, the nucleotide sequences of the present invention may be used for their ability to selectively form duplex molecules with complementary stretches of polynucleotide molecule fragments. Substantially homologous polynucleotide molecules may also be determined by computer programs that align polynucleotide sequences and estimate the ability of polynucleotide molecules to form duplex molecules under certain stringency conditions or show sequence identity with a reference sequence.

In some embodiments, the regulatory polynucleotides disclosed herein can be modified from their wild-type sequences to create regulatory polynucleotides that have variations in the polynucleotide sequence. The polynucleotide sequences of the regulatory elements of SEQ ID NOs: 1-22 may be modified or altered. One method of alteration of a polynucleotide sequence includes the use of polymerase chain reactions (PCR) to modify selected nucleotides or regions of sequences. These methods are well known to those of skill in the art. Sequences can be modified, for example, by insertion, deletion, or replacement of template sequences in a PCR-based DNA modification approach. In the context of the present invention, a "variant" is a regulatory polynucleotide containing changes in which one or more nucleotides of an original regulatory polynucleotide is deleted, added, and/or substituted. In one example, a variant regulatory polynucleotide substantially maintains its regulatory function. For example, one or more base pairs may be deleted from the 5' or 3' end of a regulatory polynucleotide to produce a "truncated" polynucleotide. One or more base pairs can also be inserted, deleted, or substituted internally to a regulatory polynucleotide. Variant regulatory polynucleotides can be produced, for example, by standard DNA mutagenesis techniques or by chemically synthesizing the variant regulatory polynucleotide or a portion thereof.

The methods and compositions provided for herein may be used for the efficient expression of transgenes in plants. The regulatory polynucleotide molecules useful for directing expression (including constitutive expression) of transcribable polynucleotides, may provide enhancement of expression (including enhancement of constitutive expression) (e.g., through the use of IME with the introns of the regulatory polynucleotides disclosed herein), and/or may provide for increased levels of expression of transcribable polynucleotides operably linked to a regulatory polynucleotide described herein. In addition, the introns identified in the regulatory polynucleotide molecules provided herein may also be included in conjunction with any other plant promoter (or plant regulatory polynucleotide) for the enhancement of the expression of selected transcribable polynucleotides.

Also provided are chimeric regulatory polynucleotide molecules. Such chimeric regulatory polynucleotides may contain one or more regulatory elements disclosed herein in operable combination with one or more additional regulatory elements. The one or more additional regulatory elements can be any additional regulatory elements from any source, including those disclosed herein, as well as those known in the art, for example, the actin 2 intron. In addition, the chimeric regulatory polynucleotide molecules may comprise any number of regulatory elements such as, for example, 2, 3, 4, 5, or more regulatory elements.

In some embodiments, the chimeric regulatory polynucleotides contain at least one core promoter molecule provided herein operably linked to one or more additional regulatory elements, such as one or more regulatory introns and/or enhancer elements. Alternatively, the chimeric regulatory polynucleotides may contain one or more regulatory elements as provided herein in combination with a minimal promoter sequence, for example, the CaMV 35S minimal promoter. Thus, the design, construction, and use of chimeric regulatory polynucleotides according to the methods disclosed herein for modulating the expression of operably linked transcribable polynucleotide molecules are also provided.

The chimeric regulatory polynucleotides as provided herein can be designed or engineered using any method. Many regulatory regions contain elements that activate, enhance, or define the strength and/or specificity of the regulatory region. Thus, for example, chimeric regulatory polynucleotides of the present invention may comprise core promoter elements containing the site of transcription initiation (e.g., RNA polymerase II binding site) combined with heterologous cis-elements located upstream of the transcription initiation site that modulate transcription levels. Thus, in one embodiment, a chimeric regulatory polynucleotide may be produced by fusing a core promoter fragment polynucleotide described herein to a cis-element from another regulatory polynucleotide; the resultant chimeric regulatory polynucleotide may cause an increase in expression of an operably linked transcribable polynucleotide molecule. Chimeric regulatory polynucleotides can be constructed such that regulatory polynucleotide fragments or elements are operably linked, for example, by placing such a fragment upstream of a minimal promoter. The core promoter regions, regulatory elements and fragments of the present invention can be used for the construction of such chimeric regulatory polynucleotides.

Thus, also provided are chimeric regulatory polynucleotide molecules comprising (1) a first polynucleotide molecule selected from the group consisting of a) a polynucleotide molecule comprising a nucleic acid molecule having the sequence of SEQ ID NOs: 1-22 that is capable of regulating transcription of an operably linked transcribable polynucleotide molecule; b) a polynucleotide molecule having at least about 70% sequence identity to the sequence of SEQ ID NOs:1-22 that is capable of regulating transcription of an operably linked transcribable polynucleotide molecule; and c) a fragment of the polynucleotide molecule of a) or b) capable of regulating transcription of an operably linked transcribable polynucleotide molecule, and (2) a second polynucleotide molecule capable of regulating transcription of an operably linked polynucleotide molecule, wherein the first polynucleotide molecule is operably linked to the second polynucleotide molecule. The chimeric regulatory polynucleotide molecules may further comprise at least a third, fourth, fifth, or more additional polynucleotide molecules capable of regulating transcription of an operably linked polynucleotide, where the at least a third, fourth, fifth, or more additional polynucleotide molecules is/are operably linked to the first and second polynucleotide molecules.

The first and second polynucleotide molecules may be any combination of regulatory elements, including those provided herein. In one embodiment, the first polynucleotide comprises at least a core promoter element and the second polynucleotide comprises at least one additional regulatory element, including, but not limited to, an enhancer, an intron, and a leader molecule.

Methods for construction of chimeric and variant regulatory polynucleotides include, but are not limited to, combining elements of different regulatory polynucleotides or duplicating portions or regions of a regulatory polynucleotide. Those of skill in the art are familiar with the standard resource materials that describe specific conditions and procedures for the construction, manipulation, and isolation of macromolecules (e.g., polynucleotide molecules, plasmids, etc.), as well as the generation of recombinant organisms and the screening and isolation of polynucleotide molecules.

Thus, also provided are novel methods and compositions for the efficient expression of transcribable polynucleotides in plants through the use of the regulatory polynucleotides described herein. The regulatory polynucleotides described herein include constitutive promoters which may find wide utility in directing the expression of potentially any polynucleotide which one desires to have expressed in a plant. The regulatory elements disclosed herein may be used as promoters within expression constructs in order to increase the level of expression of transcribable polynucleotides operably linked to any one of the disclosed regulatory polynucleotides. Alternatively, the regulatory elements disclosed herein may be included in expression constructs in conjunction with any other plant promoter for the enhancement of the expression of one or more selected polynucleotides.

Recombinant Constructs

The disclosed regulatory polynucleotide molecules find use in the production of recombinant polynucleotide constructs, for example to express transcribable polynucleotides encoding proteins of interest in a host cell.

The recombinant constructs comprise (1) an isolated regulatory polynucleotide molecule comprising a polynucleotide molecule selected from the group consisting of a) a polynucleotide molecule comprising a nucleic acid molecule having the sequence of SEQ ID NOs: 1-22 that is capable of regulating transcription of an operably linked transcribable polynucleotide molecule; b) a polynucleotide molecule having at least about 70% sequence identity to the sequence of SEQ ID NOs:1-22 that is capable of regulating transcription of an operably linked transcribable polynucleotide molecule; and c) a fragment of the polynucleotide molecule of a) or b) capable of regulating transcription of an operably linked transcribable polynucleotide molecule operably linked to (2) a transcribable polynucleotide molecule.

The constructs provided herein may contain any recombinant polynucleotide molecule having a combination of regulatory elements linked together in a functionally operative manner. For example, the constructs may contain a regulatory polynucleotide operably linked to a transcribable polynucleotide molecule operably linked to a 3' transcription termination polynucleotide molecule. In addition, the constructs may include, but are not limited to, additional regulatory polynucleotide molecules from the 3'-untranslated region (3' UTR) of plant genes (e.g., a 3' UTR to increase mRNA stability, such as the PI-II termination region of potato or the octopine or nopaline synthase 3' termination regions). Constructs may also include but are not limited to the 5' untranslated regions (5' UTR) of an mRNA polynucleotide molecule which can play an important role in translation initiation and can also be a regulatory component in a plant expression construct. For example, non-translated 5' leader polynucleotide molecules derived from heat shock protein genes have been demonstrated to enhance expression in plants. These additional upstream and downstream regulatory polynucleotide molecules may be derived from a source that is native or heterologous with respect to the other elements present on the promoter construct.

Thus, constructs generally comprise regulatory polynucleotides such as those provided herein (including modified and chimeric regulatory polynucleotides), operatively linked to a transcribable polynucleotide molecule so as to direct transcription of the transcribable polynucleotide molecule at a desired level or in a desired tissue or developmental pattern upon introduction of the construct into a plant cell. In some cases, the transcribable polynucleotide molecule comprises a protein-coding region, and the promoter provides for transcription of a functional mRNA molecule that is translated and expressed as a protein product. Constructs may also be constructed for transcription of antisense RNA molecules or other similar inhibitory RNA in order to inhibit expression of a specific RNA molecule of interest in a target host cell.

Exemplary transcribable polynucleotide molecules for incorporation into the disclosed constructs include, for example, transcribable polynucleotides from a species other than the target species, or even transcribable polynucleotides that originate with or are present in the same species, but are incorporated into recipient cells by genetic engineering methods rather than classical reproduction or breeding techniques. Exogenous polynucleotide or regulatory element is intended to refer to any polynucleotide molecule or regulatory polynucleotide that is introduced into a recipient cell. The type of polynucleotide included in the exogenous polynucleotide can include polynucleotides that are already present in the plant cell, polynucleotides from another plant, polynucleotides from a different organism, or polynucleotides generated externally, such as a polynucleotide molecule containing an antisense message of a protein-encoding molecule, or a polynucleotide molecule encoding an artificial or modified version of a protein.

The disclosed regulatory polynucleotides can be incorporated into a construct using marker genes and can be tested in transient analyses that provide an indication of expression in stable plant systems. As used herein, the term "marker gene" refers to any transcribable polynucleotide molecule whose expression can be screened for or scored in some way.

Methods of testing for marker expression in transient assays are known to those of skill in the art. Transient expression of marker genes has been reported using a variety of plants, tissues, and DNA delivery systems. For example, types of transient analyses include but are not limited to direct DNA delivery via electroporation or particle bombardment of tissues in any transient plant assay using any plant species of interest. Such transient systems would include but are not limited to electroporation of protoplasts from a variety of tissue sources or particle bombardment of specific tissues of interest. Any transient expression system may be used to evaluate regulatory polynucleotides or regulatory polynucleotide fragments operably linked to any transcribable polynucleotide molecule including, but not limited to, selected reporter genes, marker genes, or polynucleotides encoding proteins of agronomic interest. Any plant tissue may be used in the transient expression systems and include but are not limited to leaf base tissues, callus, cotyledons, roots, endosperm, embryos, floral tissue, pollen, and epidermal tissue.

Any scorable or screenable marker can be used in a transient assay as provided herein. For example, markers for transient analyses of the regulatory polynucleotides or regulatory polynucleotide fragments of the present invention include GUS or GFP. The constructs containing the regulatory polynucleotides or regulatory polynucleotide fragments of the present invention operably linked to a marker are delivered to the tissues and the tissues are analyzed by the appropriate mechanism, depending on the marker. The quantitative or qualitative analyses are used as a tool to evaluate the potential expression profile of the promoters or promoter fragments when operatively linked to polynucleotides encoding proteins of agronomic interest in stable plants.

Thus, in one embodiment, a regulatory polynucleotide molecule, or a variant, or derivative thereof, capable of regulating transcription, is operably linked to a transcribable polynucleotide molecule that provides for a selectable, screenable, or scorable marker. Markers for use in the practice of the present invention include, but are not limited to, transcribable polynucleotide molecules encoding β-glucuronidase (GUS), green fluorescent protein (GFP), luciferase (LUC), proteins that confer antibiotic resistance, or proteins that confer herbicide tolerance. Useful antibiotic resistance markers, including those encoding proteins conferring resistance to kanamycin (nptII), hygromycin B (aph IV), streptomycin or spectinomycin (aad, spec/strep), and gentamycin (aac3 and aacC4), are known in the art. Herbicides for which transgenic plant tolerance has been demonstrated and for which the methods disclosed herein can be applied include, but are not limited to, glyphosate, glufosinate, sulfonylureas, imidazolinones, bromoxynil, delapon, cyclohezanedione, protoporphyrionogen oxidase inhibitors, and isoxasflutole herbicides. Polynucleotide molecules encoding proteins involved in herbicide tolerance are known in the art, and include, but are not limited to, a polynucleotide molecule encoding 5-enolpyruvylshikimate-3-phosphate synthase (EPSP synthase); and aroA for glyphosate tolerance; a polynucleotide molecule encoding bromoxynil nitrilase (Bxn) for Bromoxynil tolerance; a polynucleotide molecule encoding phytoene desaturase (crtI) for norflurazon tolerance; a polynucleotide molecule encoding acetohydroxyacid synthase (AHAS, aka ALS) for tolerance to sulfonylurea herbicides; and the bar gene for glufosinate and bialaphos tolerance.

The regulatory polynucleotide molecules can be operably linked to any transcribable polynucleotide molecule of interest. Such transcribable polynucleotide molecules include, for example, polynucleotide molecules encoding proteins of agronomic interest. Proteins of agronomic interest can be any protein desired to be expressed in a host cell, such as, for example, proteins that provide a desirable characteristic associated with plant morphology, physiology, growth and development, yield, nutritional content, disease or pest resistance, or environmental or chemical tolerance. The expression of a protein of agronomic interest is desirable in order to confer an agronomically important trait on the plant containing the polynucleotide molecule. Proteins of agronomic interest that provide a beneficial agronomic trait to crop plants include, but are not limited to for example, proteins conferring herbicide resistance, insect control, fungal disease resistance, virus resistance, nematode resistance, bacterial disease resistance, starch production, modified oils production, high oil production, modified fatty acid content, high protein production, fruit ripening, enhanced animal and human nutrition, biopolymers, environmental stress resistance, pharmaceutical peptides, improved processing traits, improved digestibility, low raffinose, industrial enzyme production, improved flavor, nitrogen fixation, hybrid seed production, and biofuel production.

In other embodiments, the transcribable polynucleotide molecules can affect an agronomically important trait by encoding an RNA molecule that causes the targeted inhibition, or substantial inhibition, of expression of an endogenous gene (e.g., via antisense, RNAi, and/or cosuppression-mediated mechanisms). The RNA could also be a catalytic RNA molecule (i.e., a ribozyme) engineered to cleave a desired endogenous RNA product. Thus, any polynucleotide molecule that encodes a protein or mRNA that expresses a phenotype or morphology change of interest is useful for the practice of the present invention.

The constructs of the present invention may be double Ti plasmid border DNA constructs that have the right border (RB) and left border (LB) regions of the Ti plasmid isolated from *Agrobacterium tumefaciens* comprising a transfer DNA (T-DNA), that along with transfer molecules provided by the *Agrobacterium* cells, permits the integration of the T-DNA into the genome of a plant cell. The constructs also may contain the plasmid backbone DNA segments that provide replication function and antibiotic selection in bacterial cells, for example, an *E. coli* origin of replication such as ori322, a broad host range origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker. For plant transformation, the host bacterial strain is often *Agrobacterium tumefaciens* ABI, C58, or LBA4404, however, other strains known to those skilled in the art of plant transformation can function in the present invention.

Transgenic Cells, Host Cells, Plants and Plant Cells

The polynucleotides and constructs as provided herein can be used in the preparation of transgenic host cells, tissues, organs, and organisms. Thus, also provided are transgenic host cells, tissues, organs, and organisms that contain an introduced regulatory polynucleotide molecule as provided herein.

The transgenic host cells, tissues, organs, and organisms disclosed herein comprise a recombinant polynucleotide construct having (1) an isolated regulatory polynucleotide molecule comprising a polynucleotide molecule selected from the group consisting of a) a polynucleotide molecule comprising a nucleic acid molecule having the sequence of SEQ ID NOs: 1-22 that is capable of regulating transcription of an operably linked transcribable polynucleotide molecule; b) a polynucleotide molecule having at least about 70% sequence identity to the sequence of SEQ ID NOs:1-22 that is capable of regulating transcription of an operably linked transcribable polynucleotide molecule; and c) a fragment of the polynucleotide molecule of a) or b) capable of regulating transcription of an operably linked transcribable polynucleotide molecule, operably linked to (2) a transcribable polynucleotide molecule.

A plant transformation construct containing a regulatory polynucleotide as provided herein may be introduced into plants by any plant transformation method. The polynucleotide molecules and constructs provided herein may be introduced into plant cells or plants to direct transient expression of operably linked transcribable polynucleotides or be stably integrated into the host cell genome. Methods and materials for transforming plants by introducing a plant expression construct into a plant genome in the practice of this invention can include any of the well-known and demonstrated methods including electroporation; microprojectile bombardment; *Agrobacterium*-mediated transformation; and protoplast transformation.

Plants and plant cells for use in the production of the transgenic plants and plant cells include both monocotyledonous and dicotyledonous plants and plant cells. Methods for specifically transforming monocots and dicots are well known to those skilled in the art. Transformation and plant regeneration using these methods have been described for a number of crops including, but not limited to, soybean (*Glycine max*), *Brassica* sp., *Arabidopsis thaliana*, cotton (*Gossypium hirsutum*), peanut (*Arachis hypogae*), sunflower (*Helianthus annuus*), potato (*Solanum tuberosum*), tomato (*Lycopersicon esculentum* L.), rice, (*Oryza sativa*), corn (*Zea mays*), and alfalfa (*Medicago sativa*). It is apparent to those of skill in the art that a number of transformation methodologies can be used and modified for production of stable transgenic plants from any number of target crops of interest.

The transformed plants may be analyzed for the presence of the transcribable polynucleotides of interest and the expression level and/or profile conferred by the regulatory polynucleotides of the present invention. Those of skill in the art are aware of the numerous methods available for the analysis of transformed plants. For example, methods for plant analysis include, but are not limited to Southern blots or northern blots, PCR-based approaches, biochemical analyses, phenotypic screening methods, field evaluations, and immunodiagnostic assays.

The seeds of this invention can be harvested from fertile transgenic plants and be used to grow progeny generations of the transformed plants disclosed herein. The terms "seeds" and "kernels" are understood to be equivalent in meaning. In the context of the present invention, the seed refers to the mature ovule consisting of a seed coat, embryo, aleurone, and an endosperm.

Thus, also provided are methods for expressing transcribable polynucleotides in host cells, plant cells, and plants. In some embodiments, such methods comprise stably incorporating into the genome of a host cell, plant cell, or plant, a regulatory polynucleotide operably linked to a transcribable polynucleotide molecule of interest and regenerating a stably transformed plant that expresses the transcribable polynucleotide molecule. In other embodiments, such methods comprise the transient expression of a transcribable polynucleotide operably linked to a regulatory polynucleotide molecule provided herein in a host cell, plant cell, or plant.

Such methods of directing expression of a transcribable polynucleotide molecule in a host cell, such as a plant cell, include: A) introducing a recombinant nucleic acid construct into a host cell, the construct having (1) an isolated regulatory polynucleotide molecule comprising a polynucleotide molecule selected from the group consisting of a) a polynucleotide molecule comprising a nucleic acid molecule having the sequence of SEQ ID NOs: 1-22 that is capable of regulating transcription of an operably linked transcribable polynucleotide molecule; b) a polynucleotide molecule having at least about 70% sequence identity to the sequence of SEQ ID NOs:1-22 that is capable of regulating transcription of an operably linked transcribable polynucleotide molecule; and c) a fragment of the polynucleotide molecule of a) or b) capable of regulating transcription of an operably linked transcribable polynucleotide molecule, operably linked to (2) a transcribable polynucleotide molecule; and B) selecting a transgenic host cell exhibiting expression of the transcribable polynucleotide molecule.

The articles "a" and "an" are used herein to refer to one or more than one (i.e., to at least one) of the grammatical object of the article. By way of example, "an element" means one or more elements.

As used herein, the word "comprising," or variations such as "comprises" or "comprising," will be understood to imply the inclusion of a stated element, integer or step, or group of elements, integers or steps, but not the exclusion of any other element, integer or step, or group of elements, integers or steps.

The following examples are offered by way of illustration and not by way of limitation.

EXAMPLES

Example 1

Identification of *Arabidopsis* Constitutive Regulatory Sequences

A bioinformatics approach was used to identify regulatory polynucleotides that have putative constitutive activity. Most plant regulatory polynucleotides (such as promoters) that are considered to have constitutive expression have been identified by their expression characteristics at the organ level (i.e., roots, shoots, leaves, seeds) and may not be truly constitutive at the cell type/tissue level. The method used to identify the regulatory polynucleotides described herein was used to identify regulatory polynucleotides having constitutive expression activity at the cell type and/or tissue level.

Using existing microarray expression data, a bioinformatics analysis method was used to identify genes from this data collection that are highly expressed in all cell types and longitudinal zones of the *Arabidopsis* root.

Such existing data includes microarray expression profiles of all cell-types and developmental stages within *Arabidopsis* root tissue (Brady et al., *Science*, 318:801-806 (2007)). The radial dataset comprehensively profiles expression of 14 non-overlapping cell-types in the root, while the longitudinal data set profiles developmental stages by measuring expression in 13 longitudinal sections. This detailed expression profiling has mapped the spatiotemporal expression patterns of nearly all genes in the *Arabidopsis* root.

The bioinformatics analysis method identified genes based on their published absolute expression level (see Brady et al, 2007, Science. 318: 801-6). This selection process used expression values that are similar to the Robust Microchip Average (RMA) expression values where a value of approximately 1.0 corresponds to the gene being expressed. The identified genes were then filtered with expression values above a certain threshold in every expression measurement. The selection resulted in *Arabidopsis* gene candidates that are broadly expressed in all cell-types and development stages of root tissue.

To assess expression in aerial tissue and responsiveness to abiotic stress, the expression profiles of these candidates were also analyzed in the AtGenExpress Development and Abiotic Stress datasets (available on the World Wide Web at the site weigelworld.org/resources/microarray/AtGenExpress). Candidates were further selected that showed significant expression in aerial tissue throughout development and also demonstrated little or no response to abiotic stresses according to these databases.

To identify regulatory polynucleotide molecules responsible for driving high constitutive expression of these candidate genes, upstream sequences of 1500 bp or less of the selected gene candidates were determined. Because transcription start sites are not always known, sequences upstream of the translation start site were used in all cases. Therefore, the selected regulatory polynucleotide molecules contain an endogenous 5'-UTR, and some of the endogenous 5'-UTRs contain introns. The use of such introns in expression constructs containing these regulatory sequences may increase expression through IME. Without being limited by theory, IME may be important for highly expressed constitutive genes, such as those identified here. To capture these regulatory molecules in genes that do not contain a 5'-UTR intron, chimeric regulatory polynucleotide molecules may be constructed wherein the first intron from the gene of interest is fused to the 3'-end of the 5'-UTR of the regulatory polynucleotide (which may be from the same or a different (e.g., exogenous) gene). To ensure efficient intron splicing, the introns in these chimeric molecules may be flanked by consensus splice sites.

The regulatory polynucleotides listed in Table 1 below were selected. Sequences including the regulatory polynucleotides plus the first intron from the coding region added at the 3' end of the 5' UTR are indicated by the corresponding gene accession number and the indicator "+first intron". Chimeric regulatory polynucleotides prepared in which the 35S-minimal promoter sequence (5'-gcaagacccttcctctatataaggaagttcatttcatttggagagg-3') (SEQ ID NO: 23) was substituted for the −46 to −1 endogenous minimal promoter sequence relative to the transcription start site (as annotated in the TAIR database, http://www.Arabidopsis.org/) have the indicator "+35S minimal promoter".

TABLE 1

| Figure | SEQ ID NO: | Corresponding Gene Accession No. |
|---|---|---|
| 1 | 1 | AT1G13440 + first intron |
| 2 | 2 | AT1G13440 |
| 3 | 3 | AT1G22840 + first intron |
| 4 | 4 | AT1G22840 |
| 5 | 5 | AT1G22840 + first intron + 35S minimal promoter |
| 6 | 6 | AT1G52300 + first intron |
| 7 | 7 | AT1G52300 |
| 8 | 8 | AT1G52300 + first intron + 35S minimal promoter |
| 9 | 9 | AT4G37830 + first intron |
| 10 | 10 | AT4G37380 |
| 11 | 11 | AT4G37830 + first intron + 35S minimal promoter |
| 12 | 12 | AT3G08580 |
| 13 | 13 | AT3G08580 + 35S minimal promoter |
| 14 | 14 | AT1G51650 + first intron |
| 15 | 15 | AT1G51650 |
| 16 | 16 | AT1G51650 + first intron + 35S minimal promoter |
| 17 | 17 | AT3G48140 + first intron |
| 18 | 18 | AT3G48140 |
| 19 | 19 | AT3G48140 + first intron + 35S minimal promoter |
| 20 | 20 | AT3G08610 + first intron |
| 21 | 21 | AT3G08610 |
| 22 | 22 | AT3G62250 |

The nucleic acid sequences provided in FIGS. 1 through 22 are annotated to indicate one transcription start site (Capital letter in bold), the endogenous 5'-UTR intron sequences (double underlining), the first intron from the coding sequence (single underlining), the 35S-minimal promoter from base −46 to base −1 as measured from the transcription start site (dashed underlining); and any added intron splice sequences (bold italics). All *Arabidopsis* genome sequences and annotations (i.e. transcription start sites, translation start sites, and introns) are from the *Arabidopsis* Information Resource (TAIR, available on the worldwide web at the address Arabidopsis.org/indexjsp).

Example 2

Endogenous Expression of Candidate *Arabidopsis* Genes

This example shows the endogenous expression data of the genes identified through the bioinformatics filtering of Example 1. Endogenous gene expression data is provided for each gene corresponding to each of the identified *Arabidopsis* regulatory polynucleotides is provided in FIGS. 23-31. All data shown in the figures are GC-RMA (GeneChip-RMA®) normalized expression values (log 2 scale) from Affymetrix® ATH1 microarrays which allow the detection of about 24,000 protein-encoding genes from *Arabidopsis thaliana*. For each gene, four plots labeled A-D are shown in the figures. Table 2 below shows the correspondence between the regulatory polynucleotides in Example 1 and the expression plots of FIGS. 23-31.

TABLE 2

| Expression Figure (Gene Accession No.) | Regulatory Polynucleotide SEQ ID NOS (Corresponding Gene Accession No.) |
|---|---|
| 23 (AT1G13440) | 1 (AT1G13440 + first intron) |
|  | 2 (AT1G13440) |
| 24 (AT1G22840) | 3 (AT1G22840 + first intron) |
|  | 4 (AT1G22840) |
|  | 5 (AT1G22840 + first intron + 35S minimal promoter) |
| 25 (AT1G52300) | 6 (AT1G52300 + first intron) |
|  | 7 (AT1G52300) |
|  | 8 (AT1G52300 + first intron + 35S minimal promoter) |
| 26 (AT4G37830) | 9 (AT4G37830 + first intron) |
|  | 10 (AT4G37830) |
|  | 11 (AT4G37830 + first intron + 35S minimal promoter) |
| 27 (AT3G08580) | 12 (AT3G08580) |
|  | 13 (AT3G08580 + 35S minimal promoter) |
| 28 (AT1G51650) | 14 (AT1G51650 + first intron) |
|  | 15 (AT1G51650) |
|  | 16 (AT1G51650 + first intron + 35S minimal promoter) |
| 29 (AT3G48140) | 17 (AT3G48140 + first intron) |
|  | 18 (AT3G48140) |
|  | 19 (AT3G48140 + first intron + 35S minimal promoter) |
| 30 (AT3G08610) | 20 (AT3G08610 + first intron) |
|  | 21 (AT3G08610) |
| 31 (AT3G62250) | 22 (AT3G62250) |

Plots A and B are derived from data published by Brady et al. (*Science*, 318:801-806 (2007)). Plot A in each figure shows expression values from cells sorted on the basis of expressing the indicated GFP marker. Table 3 contains a key showing the specific cell types in which each marker is expressed. The table provides a description of cell types together with the associated markers. This table defines the relationship between cell-type and marker line, including which longitudinal sections of each cell-type are included. Lateral Root Primordia is included as a cell-type in this table, even though it may be a collection of multiple immature cell types. There are also no markers that differentiate between metaxylem and protoxylem or between metaphloem and protophloem, so those cell types are labeled Xylem and Phloem respectively. Together, these data provide expression information for virtually all cell-types found in the *Arabidopsis* root.

TABLE 3

| Cell Type | Markers | Longitudinal Section |
|---|---|---|
| Lateral root cap | LRC | 0-5 |
| Columella | PET111 | 0 |
| Quiescent centre | AGL42 | 1 |
|  | RM1000 | 1 |
|  | SCR5 | 1 |
| Hair cell | N/A | 1-6 |
|  | COBL9 | 7-12 |
| Non-hair cell | GL2 | 1-12 |
| Cortex | J0571 | 1-12 |
|  | CORTEX | 6-12 |
| Endodermis | J0571 | 1-12 |
|  | SCR5 | 1-12 |
| Xylem pole pericycle | WOL | 1-8 |
|  | JO121 | 8-12 |
|  | J2661 | 12 |
| Phloem pole pericycle | WOL | 1-8 |
|  | S17 | 7-12 |
|  | J2661 | 12 |
| Phloem | S32 | 1-12 |
|  | WOL | 1-8 |
| Phloem ccs | SUC2 | 9-12 |
|  | WOL | 1-8 |
| Xylem | S4 | 1-6 |
|  | S18 | 7-12 |
|  | WOL | 1-8 |
| Lateral root primordial | RM1000 | 11 |
| Procambium | WOL | 1-8 |

Plot B in each figure shows expression values from root sections along the longitudinal axis. Different regions along this axis correspond to different developmental stages of root cell development. In particular, section 0 corresponds to the columella, sections 1-6 correspond to the meristematic zone, sections 7-8 correspond to the elongation zone, and sections 9-12 correspond to the maturation zone.

Plots C and D in each figure are derived from publically available expression data of the AtGeneExpress project (available on the World Wide Web at weigelworld.org/resources/microarray/AtGenExpress). Plot C shows developmental specific expression as described by Schmid et al. (*Nat. Genet.*, 37: 501-506 (2005)). A key for the samples in this dataset is provided in Table 4. For ease of visualization, root expression values are indicated with black bars, shoot expression with white bars, flower expression with coarse hatched bars, and seed expression with fine hatched bars.

TABLE 4

| No | Sample ID | Experiment Description | Genotype | Tissue | Age | Photoperiod | Substrate |
|---|---|---|---|---|---|---|---|
| 1 | ATGE_1 | development baseline | Wt | cotyledons | 7 days | continuous light | soil |
| 2 | ATGE_2 | development baseline | Wt | hypocotyl | 7 days | continuous light | soil |
| 3 | ATGE_3 | development baseline | Wt | roots | 7 days | continuous light | soil |
| 4 | ATGE_4 | development baseline | Wt | shoot apex, vegetative + young leaves | 7 days | continuous light | soil |
| 5 | ATGE_5 | development baseline | Wt | leaves 1 + 2 | 7 days | continuous light | soil |
| 6 | ATGE_6 | development baseline | Wt | shoot apex, vegetative | 7 days | continuous light | soil |
| 7 | ATGE_7 | development baseline | Wt | seedling, green parts | 7 days | continuous light | soil |

TABLE 4-continued

| No | Sample ID | Experiment Description | Genotype | Tissue | Age | Photoperiod | Substrate |
|---|---|---|---|---|---|---|---|
| 8 | ATGE_8 | development baseline | Wt | shoot apex, transition (before bolting) | 14 days | continuous light | soil |
| 9 | ATGE_9 | development baseline | Wt | roots | 17 days | continuous light | soil |
| 10 | ATGE_10 | development baseline | Wt | rosette leaf #4, 1 cm long | 10 days | continuous light | soil |
| 11 | ATGE_11 | development baseline | gl1-T | rosette leaf #4, 1 cm long | 10 days | continuous light | soil |
| 12 | ATGE_12 | development baseline | Wt | rosette leaf # 2 | 17 days | continuous light | soil |
| 13 | ATGE_13 | development baseline | Wt | rosette leaf # 4 | 17 days | continuous light | soil |
| 14 | ATGE_14 | development baseline | Wt | rosette leaf # 6 | 17 days | continuous light | soil |
| 15 | ATGE_15 | development baseline | Wt | rosette leaf # 8 | 17 days | continuous light | soil |
| 16 | ATGE_16 | development baseline | Wt | rosette leaf # 10 | 17 days | continuous light | soil |
| 17 | ATGE_17 | development baseline | Wt | rosette leaf # 12 | 17 days | continuous light | soil |
| 18 | ATGE_18 | development baseline | gl1-T | rosette leaf # 12 | 17 days | continuous light | soil |
| 19 | ATGE_19 | development baseline | Wt | leaf 7, petiole | 17 days | continuous light | soil |
| 20 | ATGE_20 | development baseline | Wt | leaf 7, proximal half | 17 days | continuous light | soil |
| 21 | ATGE_21 | development baseline | Wt | leaf 7, distal half | 17 days | continuous light | soil |
| 22 | ATGE_22 | development baseline | Wt | developmental drift, entire rosette after transition to flowering, but before bolting | 21 days | continuous light | soil |
| 23 | ATGE_23 | development baseline | Wt | as above | 22 days | continuous light | soil |
| 24 | ATGE_24 | development baseline | Wt | as above | 23 days | continuous light | soil |
| 25 | ATGE_25 | development baseline | Wt | senescing leaves | 35 days | continuous light | soil |
| 26 | ATGE_26 | development baseline | Wt | cauline leaves | 21+ days | continuous light | soil |
| 27 | ATGE_27 | development baseline | Wt | stem, 2nd internode | 21+ days | continuous light | soil |
| 28 | ATGE_28 | development baseline | Wt | 1st node | 21+ days | continuous light | soil |
| 29 | ATGE_29 | development baseline | Wt | shoot apex, inflorescence (after bolting) | 21 days | continuous light | soil |
| 30 | ATGE_31 | development baseline | Wt | flowers stage 9 | 21+ days | continuous light | soil |
| 31 | ATGE_32 | development baseline | Wt | flowers stage 10/11 | 21+ days | continuous light | soil |
| 32 | ATGE_33 | development baseline | Wt | flowers stage 12 | 21+ days | continuous light | soil |
| 33 | ATGE_34 | development baseline | Wt | flowers stage 12, sepals | 21+ days | continuous light | soil |
| 34 | ATGE_35 | development baseline | Wt | flowers stage 12, petals | 21+ days | continuous light | soil |
| 35 | ATGE_36 | development baseline | Wt | flowers stage 12, stamens | 21+ days | continuous light | soil |
| 36 | ATGE_37 | development baseline | Wt | flowers stage 12, carpels | 21+ days | continuous light | soil |
| 37 | ATGE_39 | development baseline | Wt | flowers stage 15 | 21+ days | continuous light | soil |
| 38 | ATGE_40 | development baseline | Wt | flowers stage 15, pedicels | 21+ days | continuous light | soil |
| 39 | ATGE_41 | development baseline | Wt | flowers stage 15, sepals | 21+ days | continuous light | soil |
| 40 | ATGE_42 | development baseline | Wt | flowers stage 15, petals | 21+ days | continuous light | soil |
| 41 | ATGE_43 | development baseline | Wt | flowers stage 15, stamen | 21+ days | continuous light | soil |
| 42 | ATGE_45 | development baseline | Wt | flowers stage 15, carpels | 21+ days | continuous light | soil |

TABLE 4-continued

| No | Sample ID | Experiment Description | Genotype | Tissue | Age | Photoperiod | Substrate |
|---|---|---|---|---|---|---|---|
| 43 | ATGE_46 | development baseline | clv3-7 | shoot apex, inflorescence (after bolting) | 21+ days | continuous light | soil |
| 44 | ATGE_47 | development baseline | lfy-12 | shoot apex, inflorescence (after bolting) | 21+ days | continuous light | soil |
| 45 | ATGE_48 | development baseline | ap1-15 | shoot apex, inflorescence (after bolting) | 21+ days | continuous light | soil |
| 46 | ATGE_49 | development baseline | ap2-6 | shoot apex, inflorescence (after bolting) | 21+ days | continuous light | soil |
| 47 | ATGE_50 | development baseline | ap3-6 | shoot apex, inflorescence (after bolting) | 21+ days | continuous light | soil |
| 48 | ATGE_51 | development baseline | ag-12 | shoot apex, inflorescence (after bolting) | 21+ days | continuous light | soil |
| 49 | ATGE_52 | development baseline | ufo-1 | shoot apex, inflorescence (after bolting) | 21+ days | continuous light | soil |
| 50 | ATGE_53 | development baseline | clv3-7 | flower stage 12; multi-carpel gynoeceum; enlarged meristem; increased organ number | 21+ days | continuous light | soil |
| 51 | ATGE_54 | development baseline | lfy-12 | flower stage 12; shoot characteristics; most organs leaf-like | 21+ days | continuous light | soil |
| 52 | ATGE_55 | development baseline | ap1-15 | flower stage 12; sepals replaced by leaf-like organs, petals mostly lacking, 2° flowers | 21+ days | continuous light | soil |
| 53 | ATGE_56 | development baseline | ap2-6 | flower stage 12; no sepals or petals | 21+ days | continuous light | soil |
| 54 | ATGE_57 | development baseline | ap3-6 | flower stage 12; no petals or stamens | 21+ days | continuous light | soil |
| 55 | ATGE_58 | development baseline | ag-12 | flower stage 12; no stamens or carpels | 21+ days | continuous light | soil |
| 56 | ATGE_59 | development baseline | ufo-1 | flower stage 12; filamentous organs in whorls two and three | 21+ days | continuous light | soil |
| 57 | ATGE_73 | pollen | Wt | mature pollen | 6 wk | continuous light | soil |
| 58 | ATGE_76 | seed & silique development | Wt | siliques, w/ seeds stage 3; mid globular to early heart embryos | 8 wk | long day (16/8) | soil |
| 59 | ATGE_77 | seed & silique development | Wt | siliques, w/ seeds stage 4; early to late heart embryos | 8 wk | long day (16/8) | soil |
| 60 | ATGE_78 | seed & silique development | Wt | siliques, w/ seeds stage 5; late heart to mid torpedo embryos | 8 wk | long day (16/8) | soil |
| 61 | ATGE_79 | seed & silique development | Wt | seeds, stage 6, w/o siliques; mid to late torpedo embryos | 8 wk | long day (16/8) | soil |
| 62 | ATGE_81 | seed & silique development | Wt | seeds, stage 7, w/o siliques; late torpedo to early walking-stick embryos | 8 wk | long day (16/8) | soil |

TABLE 4-continued

| No | Sample ID | Experiment Description | Genotype | Tissue | Age | Photoperiod | Substrate |
|---|---|---|---|---|---|---|---|
| 63 | ATGE_82 | seed & silique development | Wt | seeds, stage 8, w/o siliques; walking-stick to early curled cotyledons embryos | 8 wk | long day (16/8) | soil |
| 64 | ATGE_83 | seed & silique development | Wt | seeds, stage 9, w/o siliques; curled cotyledons to early green cotyledons embryos | 8 wk | long day (16/8) | soil |
| 65 | ATGE_84 | seed & silique development | Wt | seeds, stage 10, w/o siliques; green cotyledons embryos | 8 wk | long day (16/8) | soil |
| 66 | ATGE_87 | phase change | Wt | vegetative rosette | 7 days | short day (10/14) | soil |
| 67 | ATGE_89 | phase change | Wt | vegetative rosette | 14 days | short day (10/14) | soil |
| 68 | ATGE_90 | phase change | Wt | vegetative rosette | 21 days | short day (10/14) | soil |
| 69 | ATGE_91 | comparison with CAGE | Wt | leaf | 15 days | long day (16/8) | 1x MS agar, 1% sucrose |
| 70 | ATGE_92 | comparison with CAGE | Wt | flower | 28 days | long day (16/8) | soil |
| 71 | ATGE_93 | comparison with CAGE | Wt | root | 15 days | long day (16/8) | 1x MS agar, 1% sucrose |
| 72 | ATGE_94 | development on MS agar | Wt | root | 8 days | continuous light | 1x MS agar |
| 73 | ATGE_95 | development on MS agar | Wt | root | 8 days | continuous light | 1x MS agar, 1% sucrose |
| 74 | ATGE_96 | development on MS agar | Wt | seedling, green parts | 8 days | continuous light | 1x MS agar |
| 75 | ATGE_97 | development on MS agar | Wt | seedling, green parts | 8 days | continuous light | 1x MS agar, 1% sucrose |
| 76 | ATGE_98 | development on MS agar | Wt | root | 21 days | continuous light | 1x MS agar |
| 77 | ATGE_99 | development on MS agar | Wt | root | 21 days | continuous light | 1x MS agar, 1% sucrose |
| 78 | ATGE_100 | development on MS agar | Wt | seedling, green parts | 21 days | continuous light | 1x MS agar |
| 79 | ATGE_101 | development on MS agar | Wt | seedling, green parts | 21 days | continuous light | 1x MS agar, 1% sucrose |

Plot D in each figure shows expression in response to abiotic stress as described by Kilian et al. (*Plant J.*, 50: 347-363 (2007)). The data are presented as expression values from pairs of shoots (white bars) and roots (black bars) per treatment. A key for the samples in this dataset is presented in Table 5. The table identifies the codes that are used along the x-axis in plot D in each figure. The codes are presented in 4 digit format, where the first digit represents the treatment (i.e., control=0, cold=1, osmotic stress=2, etc.), the second digit represents the time point, the third digit represents the tissue (1=shoot and 2=root), and the fourth digit represents the replication number. Since the figures provide the averages of the first and second replication, the last digit is not shown in the figures.

TABLE 5

Abiotic Stress Key

| Code | Treatment | Time point | Organ | Sample |
|---|---|---|---|---|
| 0011 | Control | 0 h | Shoots | 1 |
| 0012 | Control | 0 h | Shoots | 2 |
| 0021 | Control | 0 h | Roots | 1 |
| 0022 | Control | 0 h | Roots | 2 |
| 0711 | Control | 0.25 h | Shoots | 1 |
| 0712 | Control | 0.25 h | Shoots | 2 |
| 0721 | Control | 0.25 h | Roots | 1 |
| 0722 | Control | 0.25 h | Roots | 2 |
| 0111 | Control | 0.5 h | Shoots | 1 |

TABLE 5-continued

Abiotic Stress Key

| Code | Treatment | Time point | Organ | Sample |
|---|---|---|---|---|
| 0112 | Control | 0.5 h | Shoots | 2 |
| 0121 | Control | 0.5 h | Roots | 1 |
| 0122 | Control | 0.5 h | Roots | 2 |
| 0211 | Control | 1.0 h | Shoots | 1 |
| 0212 | Control | 1.0 h | Shoots | 2 |
| 0221 | Control | 1.0 h | Roots | 1 |
| 0222 | Control | 1.0 h | Roots | 2 |
| 0311 | Control | 3.0 h | Shoots | 1 |
| 0312 | Control | 3.0 h | Shoots | 2 |
| 0321 | Control | 3.0 h | Roots | 1 |
| 0322 | Control | 3.0 h | Roots | 2 |
| 0811 | Control | 4.0 h | Shoots | 1 |
| 0812 | Control | 4.0 h | Shoots | 2 |
| 0821 | Control | 4.0 h | Roots | 1 |
| 0822 | Control | 4.0 h | Roots | 2 |
| 0411 | Control | 6.0 h | Shoots | 1 |
| 0412 | Control | 6.0 h | Shoots | 2 |
| 0421 | Control | 6.0 h | Roots | 1 |
| 0422 | Control | 6.0 h | Roots | 2 |
| 0511 | Control | 12.0 h | Shoots | 1 |
| 0512 | Control | 12.0 h | Shoots | 2 |
| 0521 | Control | 12.0 h | Roots | 1 |
| 0522 | Control | 12.0 h | Roots | 2 |
| 0611 | Control | 24.0 h | Shoots | 1 |
| 0612 | Control | 24.0 h | Shoots | 2 |
| 0621 | Control | 24.0 h | Roots | 1 |
| 0622 | Control | 24.0 h | Roots | 2 |
| 1111 | Cold (4° C.) | 0.5 h | Shoots | 1 |
| 1112 | Cold (4° C.) | 0.5 h | Shoots | 2 |
| 1121 | Cold (4° C.) | 0.5 h | Roots | 1 |
| 1122 | Cold (4° C.) | 0.5 h | Roots | 2 |
| 1211 | Cold (4° C.) | 1.0 h | Shoots | 1 |
| 1212 | Cold (4° C.) | 1.0 h | Shoots | 2 |
| 1221 | Cold (4° C.) | 1.0 h | Roots | 1 |
| 1222 | Cold (4° C.) | 1.0 h | Roots | 2 |
| 1311 | Cold (4° C.) | 3.0 h | Shoots | 1 |
| 1312 | Cold (4° C.) | 3.0 h | Shoots | 2 |
| 1321 | Cold (4° C.) | 3.0 h | Roots | 1 |
| 1322 | Cold (4° C.) | 3.0 h | Roots | 2 |
| 1411 | Cold (4° C.) | 6.0 h | Shoots | 1 |
| 1412 | Cold (4° C.) | 6.0 h | Shoots | 2 |
| 1421 | Cold (4° C.) | 6.0 h | Roots | 1 |
| 1422 | Cold (4° C.) | 6.0 h | Roots | 2 |
| 1511 | Cold (4° C.) | 12.0 h | Shoots | 1 |
| 1512 | Cold (4° C.) | 12.0 h | Shoots | 2 |
| 1521 | Cold (4° C.) | 12.0 h | Roots | 1 |
| 1522 | Cold (4° C.) | 12.0 h | Roots | 2 |
| 1611 | Cold (4° C.) | 24.0 h | Shoots | 1 |
| 1612 | Cold (4° C.) | 24.0 h | Shoots | 2 |
| 1621 | Cold (4° C.) | 24.0 h | Roots | 1 |
| 1622 | Cold (4° C.) | 24.0 h | Roots | 2 |
| 2111 | Osmotic stress | 0.5 h | Shoots | 1 |
| 2112 | Osmotic stress | 0.5 h | Shoots | 2 |
| 2121 | Osmotic stress | 0.5 h | Roots | 1 |
| 2122 | Osmotic stress | 0.5 h | Roots | 2 |
| 2211 | Osmotic stress | 1.0 h | Shoots | 1 |
| 2212 | Osmotic stress | 1.0 h | Shoots | 2 |
| 2221 | Osmotic stress | 1.0 h | Roots | 1 |
| 2222 | Osmotic stress | 1.0 h | Roots | 2 |
| 2311 | Osmotic stress | 3.0 h | Shoots | 1 |
| 2312 | Osmotic stress | 3.0 h | Shoots | 2 |
| 2321 | Osmotic stress | 3.0 h | Roots | 1 |
| 2322 | Osmotic stress | 3.0 h | Roots | 2 |
| 2411 | Osmotic stress | 6.0 h | Shoots | 1 |
| 2412 | Osmotic stress | 6.0 h | Shoots | 2 |
| 2421 | Osmotic stress | 6.0 h | Roots | 1 |
| 2422 | Osmotic stress | 6.0 h | Roots | 2 |
| 2511 | Osmotic stress | 12.0 h | Shoots | 1 |
| 2512 | Osmotic stress | 12.0 h | Shoots | 2 |
| 2521 | Osmotic stress | 12.0 h | Roots | 1 |
| 2522 | Osmotic stress | 12.0 h | Roots | 2 |
| 2611 | Osmotic stress | 24.0 h | Shoots | 1 |
| 2612 | Osmotic stress | 24.0 h | Shoots | 2 |
| 2621 | Osmotic stress | 24.0 h | Roots | 1 |
| 2622 | Osmotic stress | 24.0 h | Roots | 2 |
| 3111 | Salt stress | 0.5 h | Shoots | 1 |
| 3112 | Salt stress | 0.5 h | Shoots | 2 |
| 3121 | Salt stress | 0.5 h | Roots | 1 |
| 3122 | Salt stress | 0.5 h | Roots | 2 |
| 3211 | Salt stress | 1.0 h | Shoots | 1 |
| 3212 | Salt stress | 1.0 h | Shoots | 2 |
| 3221 | Salt stress | 1.0 h | Roots | 1 |
| 3222 | Salt stress | 1.0 h | Roots | 2 |
| 3311 | Salt stress | 3.0 h | Shoots | 1 |
| 3312 | Salt stress | 3.0 h | Shoots | 2 |
| 3321 | Salt stress | 3.0 h | Roots | 1 |
| 3322 | Salt stress | 3.0 h | Roots | 2 |
| 3411 | Salt stress | 6.0 h | Shoots | 1 |
| 3412 | Salt stress | 6.0 h | Shoots | 2 |
| 3421 | Salt stress | 6.0 h | Roots | 1 |
| 3422 | Salt stress | 6.0 h | Roots | 2 |
| 3511 | Salt stress | 12.0 h | Shoots | 1 |
| 3512 | Salt stress | 12.0 h | Shoots | 2 |
| 3521 | Salt stress | 12.0 h | Roots | 1 |
| 3522 | Salt stress | 12.0 h | Roots | 2 |
| 3611 | Salt stress | 24.0 h | Shoots | 1 |
| 3612 | Salt stress | 24.0 h | Shoots | 2 |
| 3621 | Salt stress | 24.0 h | Roots | 1 |
| 3622 | Salt stress | 24.0 h | Roots | 2 |
| 4711 | Drought stress | 0.25 h | Shoots | 1 |
| 4712 | Drought stress | 0.25 h | Shoots | 2 |
| 4721 | Drought stress | 0.25 h | Roots | 1 |
| 4722 | Drought stress | 0.25 h | Roots | 2 |
| 4111 | Drought stress | 0.5 h | Shoots | 1 |
| 4112 | Drought stress | 0.5 h | Shoots | 2 |
| 4121 | Drought stress | 0.5 h | Roots | 1 |
| 4122 | Drought stress | 0.5 h | Roots | 2 |
| 4211 | Drought stress | 1.0 h | Shoots | 1 |
| 4212 | Drought stress | 1.0 h | Shoots | 2 |
| 4221 | Drought stress | 1.0 h | Roots | 1 |
| 4222 | Drought stress | 1.0 h | Roots | 2 |
| 4311 | Drought stress | 3.0 h | Shoots | 1 |
| 4312 | Drought stress | 3.0 h | Shoots | 2 |
| 4321 | Drought stress | 3.0 h | Roots | 1 |
| 4322 | Drought stress | 3.0 h | Roots | 2 |
| 4411 | Drought stress | 6.0 h | Shoots | 1 |
| 4412 | Drought stress | 6.0 h | Shoots | 2 |
| 4421 | Drought stress | 6.0 h | Roots | 1 |
| 4422 | Drought stress | 6.0 h | Roots | 2 |
| 4511 | Drought stress | 12.0 h | Shoots | 1 |
| 4512 | Drought stress | 12.0 h | Shoots | 2 |
| 4521 | Drought stress | 12.0 h | Roots | 1 |
| 4522 | Drought stress | 12.0 h | Roots | 2 |
| 4611 | Drought stress | 24.0 h | Shoots | 1 |
| 4612 | Drought stress | 24.0 h | Shoots | 2 |
| 4621 | Drought stress | 24.0 h | Roots | 1 |
| 4622 | Drought stress | 24.0 h | Roots | 2 |
| 5111 | Genotoxic stress | 0.5 h | Shoots | 1 |
| 5112 | Genotoxic stress | 0.5 h | Shoots | 2 |
| 5121 | Genotoxic stress | 0.5 h | Roots | 1 |
| 5122 | Genotoxic stress | 0.5 h | Roots | 2 |
| 5211 | Genotoxic stress | 1.0 h | Shoots | 1 |
| 5212 | Genotoxic stress | 1.0 h | Shoots | 2 |
| 5221 | Genotoxic stress | 1.0 h | Roots | 1 |
| 5222 | Genotoxic stress | 1.0 h | Roots | 2 |
| 5311 | Genotoxic stress | 3.0 h | Shoots | 1 |
| 5312 | Genotoxic stress | 3.0 h | Shoots | 2 |
| 5321 | Genotoxic stress | 3.0 h | Roots | 1 |
| 5322 | Genotoxic stress | 3.0 h | Roots | 2 |
| 5411 | Genotoxic stress | 6.0 h | Shoots | 1 |
| 5412 | Genotoxic stress | 6.0 h | Shoots | 2 |
| 5421 | Genotoxic stress | 6.0 h | Roots | 1 |
| 5422 | Genotoxic stress | 6.0 h | Roots | 2 |
| 5511 | Genotoxic stress | 12.0 h | Shoots | 1 |
| 5512 | Genotoxic stress | 12.0 h | Shoots | 2 |
| 5521 | Genotoxic stress | 12.0 h | Roots | 1 |
| 5522 | Genotoxic stress | 12.0 h | Roots | 2 |
| 5611 | Genotoxic stress | 24.0 h | Shoots | 1 |
| 5612 | Genotoxic stress | 24.0 h | Shoots | 2 |
| 5621 | Genotoxic stress | 24.0 h | Roots | 1 |

TABLE 5-continued

Abiotic Stress Key

| Code | Treatment | Time point | Organ | Sample |
|---|---|---|---|---|
| 5622 | Genotoxic stress | 24.0 h | Roots | 2 |
| 6111 | Oxidative stress | 0.5 h | Shoots | 1 |
| 6112 | Oxidative stress | 0.5 h | Shoots | 2 |
| 6124 | Oxidative stress | 0.5 h | Roots | 1 |
| 6122 | Oxidative stress | 0.5 h | Roots | 2 |
| 6211 | Oxidative stress | 1.0 h | Shoots | 1 |
| 6212 | Oxidative stress | 1.0 h | Shoots | 2 |
| 6223 | Oxidative stress | 1.0 h | Roots | 1 |
| 6224 | Oxidative stress | 1.0 h | Roots | 2 |
| 6311 | Oxidative stress | 3.0 h | Shoots | 1 |
| 6312 | Oxidative stress | 3.0 h | Shoots | 2 |
| 6323 | Oxidative stress | 3.0 h | Roots | 1 |
| 6322 | Oxidative stress | 3.0 h | Roots | 2 |
| 6411 | Oxidative stress | 6.0 h | Shoots | 1 |
| 6412 | Oxidative stress | 6.0 h | Shoots | 2 |
| 6421 | Oxidative stress | 6.0 h | Roots | 1 |
| 6422 | Oxidative stress | 6.0 h | Roots | 2 |
| 6511 | Oxidative stress | 12.0 h | Shoots | 1 |
| 6512 | Oxidative stress | 12.0 h | Shoots | 2 |
| 6523 | Oxidative stress | 12.0 h | Roots | 1 |
| 6524 | Oxidative stress | 12.0 h | Roots | 2 |
| 6611 | Oxidative stress | 24.0 h | Shoots | 1 |
| 6612 | Oxidative stress | 24.0 h | Shoots | 2 |
| 6621 | Oxidative stress | 24.0 h | Roots | 1 |
| 6622 | Oxidative stress | 24.0 h | Roots | 2 |
| 7711 | UV-B stress | 0.25 h | Shoots | 1 |
| 7712 | UV-B stress | 0.25 h | Shoots | 2 |
| 7721 | UV-B stress | 0.25 h | Roots | 1 |
| 7722 | UV-B stress | 0.25 h | Roots | 2 |
| 7111 | UV-B stress | 0.5 h | Shoots | 1 |
| 7112 | UV-B stress | 0.5 h | Shoots | 2 |
| 7121 | UV-B stress | 0.5 h | Roots | 1 |
| 7122 | UV-B stress | 0.5 h | Roots | 2 |
| 7211 | UV-B stress | 1.0 h | Shoots | 1 |
| 7212 | UV-B stress | 1.0 h | Shoots | 2 |
| 7221 | UV-B stress | 1.0 h | Roots | 1 |
| 7222 | UV-B stress | 1.0 h | Roots | 2 |
| 7311 | UV-B stress | 3.0 h | Shoots | 1 |
| 7312 | UV-B stress | 3.0 h | Shoots | 2 |
| 7321 | UV-B stress | 3.0 h | Roots | 1 |
| 7322 | UV-B stress | 3.0 h | Roots | 2 |
| 7411 | UV-B stress | 6.0 h | Shoots | 1 |
| 7412 | UV-B stress | 6.0 h | Shoots | 2 |
| 7421 | UV-B stress | 6.0 h | Roots | 1 |
| 7422 | UV-B stress | 6.0 h | Roots | 2 |
| 7511 | UV-B stress | 12.0 h | Shoots | 1 |
| 7512 | UV-B stress | 12.0 h | Shoots | 2 |
| 7521 | UV-B stress | 12.0 h | Roots | 1 |
| 7522 | UV-B stress | 12.0 h | Roots | 2 |
| 7611 | UV-B stress | 24.0 h | Shoots | 1 |
| 7612 | UV-B stress | 24.0 h | Shoots | 2 |
| 7621 | UV-B stress | 24.0 h | Roots | 1 |
| 7622 | UV-B stress | 24.0 h | Roots | 2 |
| 8715 | Wounding stress | 0.25 h | Shoots | 1 |
| 8712 | Wounding stress | 0.25 h | Shoots | 2 |
| 8723 | Wounding stress | 0.25 h | Roots | 1 |
| 8724 | Wounding stress | 0.25 h | Roots | 2 |
| 8111 | Wounding stress | 0.5 h | Shoots | 1 |
| 8112 | Wounding stress | 0.5 h | Shoots | 2 |
| 8124 | Wounding stress | 0.5 h | Roots | 1 |
| 8126 | Wounding stress | 0.5 h | Roots | 2 |
| 8211 | Wounding stress | 1.0 h | Shoots | 1 |
| 8214 | Wounding stress | 1.0 h | Shoots | 2 |
| 8224 | Wounding stress | 1.0 h | Roots | 1 |
| 8225 | Wounding stress | 1.0 h | Roots | 2 |
| 8313 | Wounding stress | 3.0 h | Shoots | 1 |
| 8314 | Wounding stress | 3.0 h | Shoots | 2 |
| 8324 | Wounding stress | 3.0 h | Roots | 1 |
| 8325 | Wounding stress | 3.0 h | Roots | 2 |
| 8411 | Wounding stress | 6.0 h | Shoots | 1 |
| 8412 | Wounding stress | 6.0 h | Shoots | 2 |
| 8423 | Wounding stress | 6.0 h | Roots | 1 |
| 8424 | Wounding stress | 6.0 h | Roots | 2 |
| 8511 | Wounding stress | 12.0 h | Shoots | 1 |
| 8512 | Wounding stress | 12.0 h | Shoots | 2 |
| 8524 | Wounding stress | 12.0 h | Roots | 1 |
| 8525 | Wounding stress | 12.0 h | Roots | 2 |
| 8611 | Wounding stress | 24.0 h | Shoots | 1 |
| 8612 | Wounding stress | 24.0 h | Shoots | 2 |
| 8624 | Wounding stress | 24.0 h | Roots | 1 |
| 8624_repl_8623 | Wounding stress | 24.0 h | Roots | 2 |
| 9711 | Heat stress | 0.25 h | Shoots | 1 |
| 9712 | Heat stress | 0.25 h | Shoots | 2 |
| 9721 | Heat stress | 0.25 h | Roots | 1 |
| 9722 | Heat stress | 0.25 h | Roots | 2 |
| 9111 | Heat stress | 0.5 h | Shoots | 1 |
| 9112 | Heat stress | 0.5 h | Shoots | 2 |
| 9121 | Heat stress | 0.5 h | Roots | 1 |
| 9122 | Heat stress | 0.5 h | Roots | 2 |
| 9211 | Heat stress | 1.0 h | Shoots | 1 |
| 9212 | Heat stress | 1.0 h | Shoots | 2 |
| 9221 | Heat stress | 1.0 h | Roots | 1 |
| 9222 | Heat stress | 1.0 h | Roots | 2 |
| 9311 | Heat stress | 3.0 h | Shoots | 1 |
| 9312 | Heat stress | 3.0 h | Shoots | 2 |
| 9321 | Heat stress | 3.0 h | Roots | 1 |
| 9322 | Heat stress | 3.0 h | Roots | 2 |
| 9811 | Heat stress (3 h) + 1 h | 4.0 h | Shoots | 1 |
| 9812 | Heat stress (3 h) + 1 h | 4.0 h | Shoots | 2 |
| 9821 | Heat stress (3 h) + 1 h | 4.0 h | Roots | 1 |
| 9822 | Heat stress (3 h) + 1 h | 4.0 h | Roots | 2 |
| 9411 | Heat stress (3 h) + 3 h | 6.0 h | Shoots | 1 |
| 9412 | Heat stress (3 h) + 3 h | 6.0 h | Shoots | 2 |
| 9421 | Heat stress (3 h) + 3 h | 6.0 h | Roots | 1 |
| 9422 | Heat stress (3 h) + 3 h | 6.0 h | Roots | 2 |
| 9511 | Heat stress (3 h) + 9 h | 12.0 h | Shoots | 1 |
| 9512 | Heat stress (3 h) + 9 h | 12.0 h | Shoots | 2 |
| 9521 | Heat stress (3 h) + 9 h | 12.0 h | Roots | 1 |
| 9522 | Heat stress (3 h) + 9 h | 12.0 h | Roots | 2 |
| 9611 | Heat stress (3 h) + 21 h | 24.0 h | Shoots | 1 |
| 9612 | Heat stress (3 h) + 21 h | 24.0 h | Shoots | 2 |
| 9621 | Heat stress (3 h) + 21 h | 24.0 h | Roots | 1 |
| 9622 | Heat stress (3 h) + 21 h | 24.0 h | Roots | 2 |
| C0_1 | Control | 0 h | Cell culture | 1 |
| C0_2 | Control | 0 h | Cell culture | 2 |
| C1_1 | Control | 3.0 h | Cell culture | 1 |
| C1_2 | Control | 3.0 h | Cell culture | 2 |
| C2_1 | Control | 6.0 h | Cell culture | 1 |
| C2_2 | Control | 6.0 h | Cell culture | 2 |
| C3_1 | Control | 12.0 h | Cell culture | 1 |
| C3_2 | Control | 12.0 h | Cell culture | 2 |
| C4_1 | Control | 24.0 h | Cell culture | 1 |
| C4_2 | Control | 24.0 h | Cell culture | 2 |
| C5_1 | Heat stress | 0.25 h | Cell culture | 1 |
| C5_2 | Heat stress | 0.25 h | Cell culture | 2 |
| C6_1 | Heat stress | 0.5 h | Cell culture | 1 |
| C6_2 | Heat stress | 0.5 h | Cell culture | 2 |
| C7_1 | Heat stress | 1.0 h | Cell culture | 1 |
| C7_2 | Heat stress | 1.0 h | Cell culture | 2 |
| C8_1 | Heat stress | 3.0 h | Cell culture | 1 |
| C8_2 | Heat stress | 3.0 h | Cell culture | 2 |
| C9_1 | Heat stress (3 h) + 1 h | 4.0 h | Cell culture | 1 |
| C9_2 | Heat stress (3 h) + 1 h | 4.0 h | Cell culture | 2 |
| C10_1 | Heat stress (3 h) + 3 h | 6.0 h | Cell culture | 1 |
| C10_2 | Heat stress (3 h) + 3 h | 6.0 h | Cell culture | 2 |
| C11_1 | Heat stress (3 h) + 9 h | 12.0 h | Cell culture | 1 |
| C11_2 | Heat stress (3 h) + 9 h | 12.0 h | Cell culture | 2 |
| C12_1 | Heat stress (3 h) + 21 h | 24.0 h | Cell culture | 1 |

TABLE 5-continued

Abiotic Stress Key

| Code | Treatment | Time point | Organ | Sample |
|---|---|---|---|---|
| C12_2 | Heat stress (3 h) + 21 h | 24.0 h | Cell culture | 2 |

Treatment Codes
0—Control plants, Group Kudla
The plants were treated like the treated plants; e.g.: Transfer of Magenta boxes out of the climate chamber. Opening of the boxes and lifting the raft as long as the treatments last. Then boxes were transferred back to the climate chamber.
1—Cold stress (4° C.), Group Kudla
The Magenta boxes were placed on ice in the cold room (4° C.). The environmental light intensity was 20 µEinstein/cm2 sec. An extra light which was installed over the plants had 40 µEinstein/cm2 sec. The plants stayed there.
2—Osmotic stress, Group Kudla
Mannitol was added to a concentration of 300 mM in the Media. To add Mannitol the raft was lifted out A magnetic stir bar and a stirrer were used to mix the media and the added Mannitol. After the rafts were put back in the boxes, they were transferred back to the climate chamber.
3—Salt stress, Group Kudla
NaCl was added to a concentration of 150 mM in the Media. To add NaCl the raft was lifted out. A magnetic stir bar and a stirrer were used to mix the media and the added NaCl. After the rafts were put back in the boxes, they were transferred back to the climate chamber.
4—Drought stress, Group Kudla
The plants were stressed by 15 min. dry air stream (clean bench) until 10% loss of fresh weight; then incubation in closed vessels in the climate chamber.
5—Genotoxic stress, Group Puchta
Bleomycin + mitomycin (1.5 µg/ml bleomycin + 22 µg/ml mitomycin), were added to the indicated concentration in the Media. To add the reagents the raft was lifted out A magnetic stir bar and a stirrer were used to mix the media and the added reagents. After the rafts were put back in the boxes, they were transferred back to the climate chamber.
6—Oxidative stress, Group Bartels
Methyl Viologen was added to a final concentration of 10 µM in the Media. To add the reagent the raft was lifted out A magnetic stir bar and a stirrer were used to mix the media and the added reagent. After the rafts were put back in the boxes, they were transferred back to the climate chamber
7—UV-B stress, Group Harter
15 min. 1.18 W/m2 Philips TL40W/12
8—Wounding stress, Group Harter
Punctured with pins
9—Heat stress, Group Nover/von Koskull-Döring
38° C., samples taken at 0.25, 0.5, 1.0, 3.0 h of hs and +1, +3, +9, +21 h recovery at 25° C.
C—Heat stressed suspension culture, Group Nover/von Koskull-Döring
38° C., samples taken at 0.25, 0.5, 1.0, 3.0 h of hs and +1, +3, +9, +21 h recovery at 25° C.

Example 3

Testing Expression using Identified Regulatory Polynucleotides

Regulatory polynucleotide molecules may be tested using transient expression assays using tissue bombardment and protoplast transfections following standard protocols. Reporter constructs including the respective candidate regulatory polynucleotide molecules linked to GUS are prepared and bombarded into *Arabidopsis* tissue obtained from different plant organs using a PDS-1000 Gene Gun (BioRad). GUS expression is assayed to confirm expression from the candidate promoters.

To further assess the candidate regulatory polynucleotide molecules in stable transformed plants, the candidate molecules are synthesized and cloned into commercially available constructs using the manufacturer's instructions. Regulatory polynucleotide:: GFP fusions are generated in a binary vector containing a selectable marker using commercially available vectors and methods, such as those previously described (J. Y. Lee et al., *Proc Natl Acad Sci USA* 103, 6055 (Apr. 11, 2006)). The final constructs are transferred to *Agrobacterium* for transformation into *Arabidopsis* Columbia ecotype plants by the floral dip method (S. J. Clough, A. F. Bent, *Plant J* 16, 735 (December, 1998)). Transformed plants (T1) are selected by growth in the presence of the appropriate antibiotic or herbicide. Following selection, transformants are transferred to MS plates and allowed to recover.

For preliminary analysis, T1 root tips are excised, stained with propidium iodide and imaged for GFP fluorescence with a Zeiss 510 confocal microscope. Multiple T1 plants are analyzed per construct and multiple images along the longitudinal axis are taken in order to assess expression in the meristematic, elongation, and maturation zones of the root. In some cases expression may not be detectable as GFP fluorescence, but may detectable by qRT-PCR due to the higher sensitivity of the latter technique. Thus, qRT-PCR may also be used to detect the expression of GFP.

Example 4

Preparation and Expression Testing of Chimeric Regulatory Sequences

This example provides chimeric regulatory polynucleotides to test intron mediated enhancement (IME) in selected regulatory polynucleotides that lack a 5'-UTR intron (1 of the selected candidates lacks introns completely). Chimeric polynucleotide molecules were made in which the first intron from the coding sequence was fused to the 3' end of the 5'-UTR. Consensus intron splice sites were included in these constructs to ensure efficient excision of the intron. Exemplary chimeric regulatory polynucleotide molecules prepared in this manner include those having the following nucleic acid sequences: SEQ ID NO: 1, SEQ ID NO: 3, SEQ ID NO: 5, SEQ ID NO: 6, SEQ ID NO: 8, SEQ ID NO: 9, SEQ ID NO: 11, SEQ ID NO: 14, SEQ ID NO: 16, SEQ ID NO: 17, SEQ ID NO: 19, and SEQ ID NO: 20.

The identified regulatory polynucleotides can generally be subdivided into minimal or core promoters, and upstream activating sequences. To test whether the upstream activating sequences of the selected candidates could be used with different minimal promoters, chimeric regulatory polynucleotides were prepared in which the 35S-minimal promoter sequence (−46 to −1:5'-gcaagacccttcctctatataaggaagt-tcatttcatttggagagg) (SEQ ID NO: 23) was substituted for the −46 to −1 endogenous minimal promoter sequence relative to the transcription start site (as annotated in the TAIR database, http://www.Arabidopsis.org/) from each of the selected regulatory sequences. These substitutions were all made in the promoter cassette variants containing either an endogenous 5'-UTR intron or the first intron from the coding sequence. Exemplary chimeric regulatory polynucleotides prepared in this manner include those having the following nucleic acid sequences: SEQ ID NO: 5, SEQ ID NO: 8, SEQ ID NO: 11, SEQ ID NO: 13, SEQ ID NO: 16, and SEQ ID NO: 19.

A summary of the all of the chimeric regulatory constructs made and tested is provided in Table 6, with each construct identified by the SEQ ID NO representing the nucleic acid sequence of the regulatory polynucleotide in the construct:

TABLE 6

Regulatory Polynucleotides

| Sequence ID of Regulatory Polynucelotide in Construct | source gene ID | endogenous promoter-UTR seq. used (bp) | endogenous 5'-UTR intron (bp) | 1st intron added to A & C (bp) | 35S minimal promoter substituted |
|---|---|---|---|---|---|
| 1 | AT1G13440 | 1107 | — | 93 | — |
| 2 | AT1G13440 | 1107 | — | — | — |
| 3 | AT1G22840 | 293 | — | 479 | — |

TABLE 6-continued

Regulatory Polynucleotides

| Sequence ID of Regulatory Polynucelotide in Construct | source gene ID | endogenous promoter-UTR seq. used (bp) | endogenous 5'-UTR intron (bp) | 1st intron added to A & C (bp) | 35S minimal promoter substituted |
|---|---|---|---|---|---|
| 4 | AT1G22840 | 293 | — | — | — |
| 5 | AT1G22840 | 293 | — | 479 | Yes |
| 6 | AT1G52300 | 1099 | — | 102 | — |
| 7 | AT1G52300 | 1099 | — | — | — |
| 8 | AT1G52300 | 1099 | — | 102 | Yes |
| 9 | AT4G37830 | 858 | — | 343 | — |
| 10 | AT4G37830 | 858 | — | — | — |
| 11 | AT4G37830 | 858 | — | 343 | Yes |
| 12 | AT3G08580 | 707 | 493 | — | — |
| 13 | AT3G08580 | 707 | 493 | — | Yes |
| 14 | AT1G51650 | 815 | — | 749 | — |
| 15 | AT1G51650 | 815 | — | — | — |
| 16 | AT1G51650 | 815 | — | 749 | Yes |
| 17 | AT3G48140 | 1043 | — | 157 | — |
| 18 | AT3G48140 | 1043 | — | — | — |
| 19 | AT3G48140 | 1043 | — | 157 | Yes |
| 20 | AT3G08610 | 685 | — | 136 | — |
| 21 | AT3G08610 | 685 | | | |
| 22 | AT3G62250 | 185 | — | — | — |

Candidate regulatory polynucleotide molecules were synthesized by contract (Blue Heron Biotechnology) and operably linked to a green fluorescent protein (GFP) coding sequence in a plant transformation binary vector. The final constructs were transferred to *Agrobacterium* and transformed into *Arabidopsis* Columbia ecotype plants by the floral dip method (S. J. Clough, A. F. Bent, *Plant J* 16, 735 (December, 1998)). Transformed plants (T1) were selected by growth on BASTA plates for 8 days. Following selection, transformants were transferred to MS plates and allowed to recover for 7-8 days. For preliminary analysis, T1 root tips were excised, stained with propidium iodide and imaged for GFP fluorescence with a Zeiss 510 confocal microscope. Five T1s were analyzed per construct and multiple images along the longitudinal axis were taken in order to assess expression in the meristematic, elongation and maturation zones of the root. The same sensitivity settings were used in all cases to provide semi-quantitative comparisons between images.

Semi-quantitative results from GFP intensity rankings are summarized in Table 7, with each construct identified by the SEQ ID NO representing the nucleic acid sequence of the regulatory polynucleotide in the construct. Some representative images of individual T1 seedlings are shown in FIGS. 34A-B through 38A-B. The images of FIGS. 34A-B through 38A-B show two channels, red and green, superimposed. The red channel shows cell wall staining and the green channel shows expression of GFP. The signal from the red channel was converted to white. Signal from the green channel was converted to grayscale such that the gray background outside of the root shows zero expression of GFP while any gray shade that is darker than the gray background outside of the root indicates

TABLE 7

GFP fluorescence in stably transformed *Arabidopsis*

| Regulatory Polynucleotide Sequence ID in Construct | Degree of GFP Fluorescence |
|---|---|
| 1 | + |
| 2 | + |
| 3 | ++ |
| 4 | + |
| 5 | ++ |
| 6 | +++++ |
| 7 | +++ |
| 8 | + |
| 9 | ++++ |
| 10 | *[2] |
| 11 | +  |
| 12 | +++++ |
| 13 | ++++ |
| 14 | ++++ |
| 15 | *[2] |
| 16 | + |
| 17 | + |
| 18 | + |
| 19 | + |
| 20 | + |
| 21 | —[1] |
| 22 | +++ |
| 23 (35S control) | +++ |

[1] — = no fluorescence detected under these conditions; no qRT-PCR data
[2] * = no fluorescence detected under these conditions but expression detected by qRT-PCR GFP expression. FIGS. 34A-B through 38A-B show elongation and meristematic zones of representative plants containing constructs with the regulatory polynucleotides having the following nucleic acid sequences: SEQ ID NO: 6 (FIG. 34A: elongation zone, FIG. 34B: meristematic zone), SEQ ID NO: 9 (FIG. 35A: elongation zone, FIG. 35B: meristematic zone), SEQ ID NO: 12 (FIG. 36A: elongation zone, FIG. 36B: meristematic zone), SEQ ID NO: 13 (FIG. 37A: elongation zone, FIG. 37B: meristematic zone), and SEQ ID NO: 14 (FIG. 38A: elongation zone, FIG. 38B: meristematic zone).

All images were taken with the same microscope settings. Note that minimal differences were observed in T1s from the same construct. In some cases expression was not detectable as GFP fluorescence but was detectable by qRT-PCR due to the higher sensitivity of the latter technique.

Example 5

Generation of Derivative Regulatory Polynucleotides

This example illustrates the utility of derivatives of the native *Arabidopsis* regulatory polynucleotides. Derivatives of the *Arabidopsis* regulatory polynucleotides are generated by introducing mutations into the nucleotide sequence of the native regulatory polynucleotides. A plurality of mutagenized DNA segments derived from the *Arabidopsis* regulatory polynucleotides including derivatives with nucleotide deletions and modifications are generated and inserted into a plant transformation vector operably linked to a GUS marker gene. Each of the plant transformation vectors are prepared, for example, essentially as described in Example 3 above, except that the full length *Arabidopsis* polynucleotide is replaced by a mutagenized derivative of the *Arabidopsis* polynucleotide. *Arabidopsis* plants are transformed with each of the plant transformation vectors and analyzed for expression of the GUS marker to identify those mutagenized derivatives having regulatory activity.

Example 6

Identification of Regulatory Fragments

This example illustrates the utility of modified regulatory polynucleotides derived from the native *Arabidopsis* polynucleotides. Fragments of the polynucleotides are generated by designing primers to clone fragments of the native *Arabidopsis* regulatory polynucleotide. A plurality of cloned fragments of the polynucleotides ranging in size from 50 nucleotides up to about full length are obtained using PCR reactions with primers designed to amplify various size fragments instead of the full length polynucleotide. 3' fragments from the 3' end of the *Arabidopsis* regulatory polynucleotide comprising random fragments of about 50, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600 and 1650 nucleotides in length from various parts of the *Arabidopsis* regulatory polynucleotides are obtained and inserted into a plant transformation vector operably linked to a GUS marker gene. Each of the plant transformation vectors is prepared essentially as described, for example, in Example 3 above, except that the full length *Arabidopsis* polynucleotide is replaced by a fragment of the *Arabidopsis* regulatory polynucleotide or a combination of a 3' fragment and a random fragment. *Arabidopsis* plants are transformed with each of the plant transformation vectors and analyzed for expression of the GUS marker to identify those fragments having regulatory activity.

Example 7

Identification of Orthologs

This example illustrates the identification and isolation of regulatory polynucleotides from organisms other than *Arabidopsis* using the native *Arabidopsis* polynucleotide sequences and fragments to query genomic DNA from other organisms in a publicly available nucleotide data bases including GENBANK. Orthologous genes in other organisms can be identified using reciprocal best hit BLAST methods as described in Moreno-Hagelsieb and Latimer, Bioinformatics (2008) 24:319-324. The Gramene.org database could also be queried to identify rice (*Oryza sativa japonica*) orthologs corresponding to the *Arabidopsis* genes whose regulatory elements were identified in Example 1 above. In some cases, the *Arabidopsis* genes may lack a rice ortholog and in other cases the *Arabidopsis* genes may have more than one ortholog.

Once an ortholog gene is identified, its corresponding regulatory polynucleotide sequence can be selected using methods described for *Arabidopsis* in Example 1. The full length polynucleotides may be cloned and inserted into a plant transformation vector which is used to transform *Arabidopsis* plants essentially as illustrated in Examples 3 or 4 above to verify regulatory activity and expression patterns.

Example 8

*Arabidopsis* Ubiquitin Regulatory Sequences

One *Arabidopsis* sequence identified using the technique of Example 1 was AT4g05320 (also referred to as the *Arabidopsis* polyubiquitin gene UBQ10). FIG. 32A provides the nucleotide sequence of the regulatory polynucleotide of the *Arabidopsis* gene having Accession No. AT4g05320 (SEQ ID NO: 24), with the sequence being annotated as described in Example 1. The expression pattern of the *Arabidopsis* ubiquitin gene was shown to be constitutive at the cell type/tissue level by the methods described in Example 1. Plots B and C (FIGS. 32B and 32C, respectively) are derived from data published by Brady et al. (*Science*, 318:801-806 (2007)) as discussed in Example 2 above. Plot B (FIG. 32B) provides the expression values of this gene in different cell types which were sorted on the basis of expressing the indicated GFP markers. Plot C (FIG. 32C) provides the expression values of this gene from root sections along the longitudinal axis of the root. FIG. 32D provides the developmental specific expression of AT4G05320. FIG. 32E provides the expression of AT4G05320 in response to various abiotic stresses. Plots D and E in FIG. 32 are derived from publically available expression data of the AtGeneExpress project (available on the World Wide Web at weigelworld.org/resources/microarray/AtGenExpress) also as discussed in Example 2. Plot D (FIG. 32D) shows developmental specific expression as described by Schmid et al. (*Nat. Genet.*, 37: 501-506 (2005)). Plot E (FIG. 32E) shows expression in response to abiotic stress as described by Kilian et al. (*Plant J.*, 50: 347-363 (2007)) as discussed above in Example 2.

A recombinant construct containing an approximately 1.2 kb fragment (including a 304 bp endogenous 5'-UTR intron) of the regulatory region from the *Arabidopsis* ubiquitin gene UBQ10 (corresponding to Accession No. AT4g05320) operably linked to the green fluorescent protein (GFP) coding sequence was prepared, and is referred to as construct A. A summary of the sequence used in Construct A is provided in Table 8.

TABLE 8

| source gene ID | endogenous promoter-UTR seq. used (bp) | endogenous 5'-UTR intron (bp) |
| --- | --- | --- |
| AT4G05320 | 1201 | 304 |

Construct A was transferred to *Agrobacterium* and transformed into *Arabidopsis* Columbia ecotype plants by the floral dip method (S. J. Clough, A. F. Bent, *Plant J* 16, 735 (December, 1998)). Transformed plants (T1) were selected by growth on BASTA plates for 8 days. Following selection, transformants were transferred to MS plates and allowed to recover for 7-8 days. For preliminary analysis, T1 root tips were excised, stained with propidium iodide and imaged for GFP fluorescence with a Zeiss 510 confocal microscope. Five T1s were analyzed and multiple images along the longitudinal axis were taken in order to assess expression in the meristematic, elongation and maturation zones of the root. The same sensitivity settings were used in all cases to provide semi-quantitative comparisons between images.

Two representative images are shown in FIGS. 39A-B. The images show two channels, red and green, superimposed. The red channel shows cell wall staining and the green channel shows expression of GFP. The signal from the red channel was converted to white. Signal from the green channel was converted to grayscale such that the gray background outside of the root shows zero expression of GFP while any gray shade that is darker than the gray background outside of the root indicates GFP expression. FIG. 39A shows the elongation zone and FIG. 39B shows the meristematic zone for a representative plant containing Construct A.

Additional T1 seedlings transformed with Construct A were selected, transferred to soil, and allowed to set seed. T2 seed was harvested from multiple T1 lines and single insertion lines were identified by 3:1 segregation of the selection marker in T2 seedlings. T2 seedlings from single insertion lines were grown under standard Murashige and Skoog (MS) media conditions and roots were analyzed for GFP fluorescence with a Zeiss 510 confocal microscope expression. Seedlings were then kept in MS media or transferred to high salt (MS+20 mM NaCl), low nitrogen (MS containing 0.5 mM N), or low pH (MS pH 4.6) conditions for 24 h. The roots were then again analyzed for GFP fluorescence to test expression responses to abiotic stress. The 3 stress conditions were validated to confer differential expression of known stress-responsive genes. One to seven T2 seedlings containing the transgene were analyzed per line and multiple images along the longitudinal axis were taken in order to assess expression in the meristematic, elongation and maturation zones of the root. The same sensitivity settings were used in all cases to provide quantitative comparisons between images. GFP expression in different cell-types was, determined from the images using a predefined root template. The template was calculated using a series of images manually segmented to find the root's "tissue percentage profile" (TPP), in which each region of interest in the template is a percentage of the root thickness at the specified location relative to the quiescent center (QC). Using different TPPs for each root zone, the images were segmented into different regions of interest (ROI) corresponding to different root cell-types. The average grayscale intensity of each ROI from the GFP fluorescence channel was then calculated and presented as the GFP Expression Index (GEI). The GEI varies from 0 and 1, which corresponds to no GFP expression (GEI=0) and complete saturation of GFP signal (GEI=1), respectively. FIGS. 33A, 33B, and 33C show the average GEI (±SEM) in different cell-types in 3 longitudinal zones under standard and 3 stress conditions. Note that the average GEI across all root regions for non-transgenic *Arabidopsis* seedlings (i.e. the background signal) is 0.0244±0.0011. These data show that the regulatory region used in construct A drives constitutive expression of GFP that was generally unresponsive to abiotic stress.

Example 9

Preparation and Quantitative Root Expression Testing of Identified Regulatory Elements in Stably Transformed *Arabidopsis*

Six to sixteen additional BASTA resistant T1s, generated as described in Examples 4 and 5 and containing a construct with one of the regulatory polynucleotides represented by SEQ ID NOS: 1-22, 23, or 24, were selected per construct and allowed to set seed (T2 generation). At least two T2 lines per construct were identified that segregated 3:1 for herbicide resistance indicating they arose from single locus transgene insertion events. Plants from these lines were allowed to set seed (T3 generation) and homozygous T3 lines were identified for further characterization.

High resolution, quantitative measurements of GFP fluorescence in roots were then undertaken on two homozygous T3 lines for representative constructs. T3 seed from the two lines was grown in MS media in the RootArray, a device designed for confocal imaging of living plant roots under controlled conditions, and described in U.S. Patent Publication No. 2008/0141585 which is incorporated herein by reference in its entirety. After 5 days growth, the roots were stained with FM4-64 and imaged for GFP fluorescence in the meristematic zone, elongation zone and maturation zone with approximately 50 seedlings analyzed per line.

In order to yield quantitative results from image pixel intensities, imaging conditions and measurements were strictly controlled. The imaging normalization and calibration methods were based on two key measurements. First, on any day measurements are taken, a dilution series of an external reference fluorophore was quantitatively imaged. Second, the post objective laser intensity was directly measured before and after each RootArray experiment in order to account for variations in laser light intensity that may have occurred.

The dilution series that was imaged each day was prepared from a reference standard. The reference standard was prepared from a concentrated stock of Alexa Fluor 488® fluorophore in MES buffer (pH 6.0), with its concentration determined by spectrophotometry. Aliquots of the reference standard were stored at −20° C. as a master stock. For calibration use, a dilution series of the stock was prepared in a sealed, modified 96 well plate. The dilution series was stored at 4° C. in the dark and used for up to one month before being replaced. The Alexa Fluor® standard was verified to be stable under these conditions. The dilution series was imaged at the beginning of each day to characterize the performance of the detector and optics of the microscope as described below.

Tests have shown that laser light intensity can vary up to 10% at a given setting over the course of a RootArray experiment. To correct for this, laser power is measured before and after each RootArray experiment. The laser intensity is actively adjusted to 355±15 μW at 488 nm at the beginning of each experiment. The change in intensity measured at the end of a RootArray experiment was assumed to be due to a linear transition. Therefore, the estimated light intensity for a specific RootArray image was interpolated from that image's timestamp.

To correct for variations in laser intensity and detector response a model was developed to describe how Alexa Fluor® 488 fluorescence varied with laser intensity under the imaging conditions described herein. The laser correction model for Alexa Fluor 488® is based on the relative change of the dilution series slope versus the relative change of laser light intensity. Experiments have demonstrated that this relationship is independent of scan settings. This model was then adapted to GFP in root tissue with the addition of a GFP specific variable. This model is used to calculate a GFP expression index (GEI) as described in Equation 1 below (it is noted that the equation used to calculate the GFP Expression Index (GEI) in this example is slightly different from the equation used to calculate the GFP Expression Index in Example 8.

$$GEI = \frac{\mu(roi(Img) - bkg(Img))}{\alpha_{AF}^{DS} \beta_{Sat}} \gamma_{AF}^{DS} \gamma_{AF}^{Img} \delta_{GFP}^{Img} \qquad \text{Equation 1}$$

GFP expression index (GEI)

roi (1 mg): The pixel population for the quantification channel (green channel) over a selected region of interest. In this case each ROI is a tissue type.

bkg (1 mg): The background pixel value for every experimental image is characterized with a novel statistics based approach.

$\alpha_{AF}^{DS}$: Normalized slope of the dilution series standard.

$\gamma_{AF}^{DS}$: Laser correction factor for Alexa Fluor 488® fluorophore to normalize the dilution series to the reference laser power (355 µW at 488 nm).

$\gamma_{AF}^{Img}$: Laser correction factor for Alexa Fluor 488® fluorophore at the laser power the GFP image was taken.

$\delta_{GFP}^{Img}$: Relative laser correction factor for GFP fluorophore in the experimental image.

$\beta_{Sat}$: Normalization constant to prevent pixel oversaturation of the detector when the image was acquired.

The green channel image signal passes through this function to produce the GEI, a metric of fluorescent intensity that allows for comparison across RootArrays over time. The background of each experimental image was calculated as described below and subsequently subtracted from the pixel population of the region of interest. The negative values were zeroed to create an image with minimal background noise. The mean of corrected pixel intensities was divided by the slope of the dilution series to convert the pixel output to a metric of light intensity relative to the dilution series standard. The first gamma value ($\gamma_{AF}^{DS}$) is a laser correction factor that adjusts the slope of the dilution series to what it would be if the dilution series was imaged at exactly 355 µW. The next gamma ($\gamma_{AF}^{Img}$) and the delta values ($\delta_{GFP}^{Img}$) correct the GFP signal to what it would be if the root was imaged at exactly 355 µW. It is noted that all correction factors typically varied by less than 5% between experiments.

Regions of interest that have a strong signal near the point of pixel oversaturation of the detector did not exhibit a linear relationship with GFP expression. Therefore a normalization constant $\beta_{Sat}$ was included to limit the scope of the dynamic bit range of the detector and the GEI is capped at 1 to preserve its linear correlation with GFP expression for all reported values <1. To calculate the background of an image(bkg (Img)), the image was first split into a grid of squares and the pixel population of each square is examined. A small number of squares was initially selected based on having the lowest percentile rankings in terms of standard deviation, $95^{th}$ percentile pixel value, mean, median, and gradient magnitude. The pixel populations in the initial "seed" squares, which are assumed to be background, were then compared against the pixel populations of all other squares in a one tailed unpaired t test in order to categorize each square as "background" or "non-background". The median pixel intensity of all squares determined to be "background" was then used as the bkg (1 mg) value in Equation 1. Tests have shown that this algorithm robustly selected background pixel populations even if there were several roots in the field of view.

The correspondence of regions of interest to different cell-types was determined from the images using a predefined root template. The template was calculated using a series of images manually segmented to find the root's "tissue percentage profile" (TPP), in which each region of interest in the template is a percentage of the root thickness at the specified location relative to the quiescent center (QC). Using different TPPs for each root zone, the images were segmented into different regions of interest (ROI) corresponding to different root cell-types. Specifically, the regions determined in all three developmental zones were the epidermis, the cortex, the endodermis, and the stele. In addition to these four regions, the root cap and the quiescent center were also determined in the meristematic zone.

To determine if a particular transgenic line exhibited significant GFP expression in an ROI, the GEI measurements for each of the 14 tissue-zone ROIs were compared to the corresponding values determined from 48 non-transgenic *Arabidopsis* Columbia ecotype seedlings grown under identical conditions. Significance was determined using a one-tailed Welch's t-test with a cutoff of $p<0.01$.

The average GEI for each of the 14 tissue-zone ROIs for 2 representative lines of each regulatory molecule that passed prescreening is shown in Tables 9-11. All values represent significant expression ($p<0.01$) unless indicated by bold italics. The GEIS measured from seedlings containing a 35S promoter-GFP transgene are shown for comparison. The 35S promoter is widely used in plant biotechnology and considered a standard for strong promoters. The GEIs measured from seedlings containing the regulatory region from the UBQ10 gene (see Example 8) are also shown for comparison. These data show that the regulatory polynucleotides listed in Tables 9-11 generally drive constitutive expression in the root.

Table 9 shows the GEI values of promoter sequences in regions of the meristematic zone.

TABLE 9

| Promoter Sequence (SEQ ID NO) | Gene from which promoter is derived ("+ intron" is listed where the first intron from coding sequence was added as described above) | Meristem | | | | | |
|---|---|---|---|---|---|---|---|
| | | epidermis | cortex | endodermis | stele | QC | Root cap |
| 23 (35S control) | | 0.396 | 0.282 | 0.236 | 0.229 | 0.957 | 1.000 |
| 23 (35S control) | | 0.505 | 0.253 | 0.206 | 0.189 | 0.766 | 0.844 |
| 1 | AT1G13440 + intron | *0.008* | *0.008* | *0.007* | *0.005* | 0.014 | 0.008 |
| 1 | AT1G13440 + intron | 0.009 | 0.009 | 0.008 | 0.006 | 0.014 | 0.009 |
| 2 | AT1G13440 | 0.015 | 0.060 | 0.039 | 0.016 | 0.210 | 0.018 |
| 2 | AT1G13440 | 0.013 | 0.015 | 0.012 | 0.009 | 0.047 | 0.014 |
| 3 | AT1G22840 + intron | 0.068 | 0.059 | 0.057 | 0.048 | 0.056 | 0.070 |
| 3 | AT1G22840 + intron | 0.037 | 0.036 | 0.033 | 0.025 | 0.030 | 0.037 |
| 4 | AT1G22840 | 0.008 | 0.008 | 0.007 | *0.005* | *0.008* | 0.008 |
| 4 | AT1G22840 | 0.009 | 0.008 | 0.007 | 0.006 | 0.008 | 0.008 |
| 6 | AT1G52300 + intron | 0.889 | 0.850 | 0.808 | 0.657 | 0.421 | 0.471 |
| 6 | AT1G52300 + intron | 0.907 | 0.897 | 0.899 | 0.870 | 0.701 | 0.531 |
| 7 | AT1G52300 | 0.130 | 0.126 | 0.125 | 0.109 | 0.042 | 0.038 |
| 7 | AT1G52300 | 0.322 | 0.320 | 0.326 | 0.304 | 0.089 | 0.062 |
| 9 | AT4G37830 + intron | 0.522 | 0.445 | 0.425 | 0.382 | 0.494 | 0.584 |

TABLE 9-continued

| Promoter Sequence (SEQ ID NO) | Gene from which promoter is derived ("+ intron" is listed where the first intron from coding sequence was added as described above) | Meristem | | | | | |
|---|---|---|---|---|---|---|---|
| | | epidermis | cortex | endodermis | stele | QC | Root cap |
| 9 | AT4G37830 + intron | 0.143 | 0.128 | 0.123 | 0.112 | 0.147 | 0.167 |
| 10 | AT4G37830 | 0.009 | 0.008 | *0.007* | *0.005* | *0.008* | *0.008* |
| 10 | AT4G37830 | 0.009 | 0.008 | 0.008 | *0.006* | *0.008* | 0.008 |
| 12 | AT3G08580 | 0.850 | 0.792 | 0.753 | 0.678 | 0.858 | 0.891 |
| 12 | AT3G08580 | 0.991 | 0.993 | 0.992 | 0.992 | 0.997 | 0.999 |
| 14 | AT1G51650 + intron | 0.695 | 0.578 | 0.559 | 0.504 | 0.723 | 0.821 |
| 14 | AT1G51650 + intron | 0.645 | 0.466 | 0.435 | 0.381 | 0.603 | 0.646 |
| 15 | AT1G51650 | *0.007* | *0.006* | *0.006* | *0.005* | *0.007* | *0.007* |
| 15 | AT1G51650 | *0.007* | *0.006* | *0.005* | *0.004* | *0.007* | *0.007* |
| 17 | AT3G48140 + intron | 0.056 | 0.034 | 0.030 | 0.019 | 0.034 | 0.121 |
| 17 | AT3G48140 + intron | 0.027 | 0.019 | 0.016 | 0.013 | 0.021 | 0.054 |
| 18 | AT3G48140 | 0.010 | *0.008* | *0.007* | *0.006* | *0.008* | *0.010* |
| 18 | AT3G48140 | 0.011 | 0.008 | 0.007 | 0.006 | 0.011 | 0.037 |
| 20 | AT3G08610 + intron | 0.048 | 0.030 | 0.027 | 0.024 | 0.052 | 0.071 |
| 20 | AT3G08610 + intron | 0.041 | 0.028 | 0.026 | 0.023 | 0.044 | 0.064 |
| 21 | AT3G08610 | *0.007* | *0.007* | *0.006* | *0.005* | *0.008* | 0.008 |
| 21 | AT3G08610 | *0.008* | *0.007* | *0.007* | *0.005* | *0.008* | 0.008 |
| 22 | AT3G62250 | 0.295 | 0.277 | 0.263 | 0.186 | 0.198 | 0.150 |
| 22 | AT3G62250 | 0.292 | 0.286 | 0.269 | 0.195 | 0.206 | 0.165 |
| 24 | AT4G05320 (UBQ10) | 0.711 | 0.551 | 0.493 | 0.405 | 0.962 | 1 |
| 24 | AT4G05320 (UBQ10) | 0.313 | 0.219 | 0.194 | 0.129 | 0.296 | 0.798 |

Table 10 shows the GEI values of promoter sequences in regions of the elongation zone.

TABLE 10

| Promoter Sequence (SEQ ID NO) | Gene from which promoter is derived ("+intron" is listed where the first intron from coding sequence was added as described above) | Elongation | | | |
|---|---|---|---|---|---|
| | | epi-dermis | cortex | endo-dermis | stele |
| 23 (35S control) | | 0.240 | 0.083 | 0.084 | 0.195 |
| 23 (35S control) | | 0.137 | 0.045 | 0.051 | 0.132 |
| 1 | AT1G13440 + intron | *0.006* | *0.004* | *0.003* | 0.005 |
| 1 | AT1G13440 + intron | *0.006* | *0.004* | *0.003* | *0.003* |
| 2 | AT1G13440 | 0.006 | 0.012 | 0.011 | 0.007 |
| 2 | AT1G13440 | *0.006* | *0.004* | *0.003* | *0.003* |
| 3 | AT1G22840 + intron | 0.039 | 0.022 | 0.016 | 0.018 |
| 3 | AT1G22840 + intron | 0.022 | 0.013 | 0.011 | 0.011 |
| 4 | AT1G22840 | *0.005* | *0.004* | *0.003* | *0.003* |
| 4 | AT1G22840 | 0.006 | *0.004* | *0.004* | *0.004* |
| 6 | AT1G52300 + intron | 0.343 | 0.251 | 0.225 | 0.249 |
| 6 | AT1G52300 + intron | 0.339 | 0.225 | 0.196 | 0.251 |
| 7 | AT1G52300 | 0.038 | 0.025 | 0.020 | 0.025 |
| 7 | AT1G52300 | 0.078 | 0.050 | 0.044 | 0.057 |
| 9 | AT4G37830 + intron | 0.272 | 0.172 | 0.136 | 0.145 |
| 9 | AT4G37830 + intron | 0.064 | 0.043 | 0.035 | 0.037 |
| 10 | AT4G37830 | 0.006 | *0.004* | *0.003* | *0.003* |
| 10 | AT4G37830 | *0.006* | *0.004* | *0.003* | *0.003* |
| 12 | AT3G08580 | 0.556 | 0.374 | 0.293 | 0.285 |
| 12 | AT3G08580 | 0.987 | 0.863 | 0.687 | 0.693 |
| 14 | AT1G51650 + intron | 0.511 | 0.343 | 0.286 | 0.300 |
| 14 | AT1G51650 + intron | 0.315 | 0.212 | 0.174 | 0.195 |
| 15 | AT1G51650 | *0.005* | *0.004* | *0.004* | *0.004* |
| 15 | AT1G51650 | *0.005* | *0.004* | *0.004* | *0.004* |
| 17 | AT3G48140 + intron | 0.021 | 0.011 | 0.009 | 0.010 |
| 17 | AT3G48140 + intron | 0.011 | 0.007 | 0.007 | 0.008 |
| 18 | AT3G48140 | *0.006* | *0.005* | *0.004* | *0.004* |
| 18 | AT3G48140 | 0.007 | 0.005 | 0.005 | 0.005 |
| 20 | At3G08610 + intron | 0.034 | 0.019 | 0.014 | 0.014 |
| 20 | At3G08610 + intron | 0.027 | 0.016 | 0.012 | 0.013 |
| 21 | At3G08610 | 0.007 | 0.005 | *0.005* | *0.005* |
| 21 | At3G08610 | *0.006* | *0.005* | *0.004* | *0.005* |
| 22 | AT3G62250 | 0.099 | 0.056 | 0.043 | 0.043 |
| 22 | AT3G62250 | 0.078 | 0.054 | 0.043 | 0.042 |
| 24 | AT4G05320 (UBQ10) | 0.404 | 0.271 | 0.224 | 0.247 |
| 24 | AT4G05320 (UBQ10) | 0.223 | 0.171 | 0.131 | 0.116 |

Table 11 shows the GEI values of promoter sequences in regions of the maturation zone.

TABLE 11

| Promoter Sequence (SEQ ID NO) | Gene from which promoter is derived ("+intron" is listed where the first intron from coding sequence was added as described above) | Maturation | | | |
|---|---|---|---|---|---|
| | | epi-dermis | cortex | endo-dermis | stele |
| 23 (35S control) | | 0.235 | 0.216 | 0.310 | 0.545 |
| 23 (35S control) | | 0.271 | 0.289 | 0.439 | 0.674 |
| 1 | AT1G13440 + intron | *0.007* | *0.004* | *0.005* | 0.027 |
| 1 | AT1G13440 + intron | *0.006* | *0.004* | *0.004* | 0.010 |
| 2 | AT1G13440 | *0.007* | 0.011 | 0.015 | 0.012 |
| 2 | AT1G13440 | *0.007* | *0.005* | 0.007 | 0.015 |
| 3 | AT1G22840 + intron | 0.019 | 0.014 | 0.020 | 0.029 |
| 3 | AT1G22840 + intron | 0.014 | 0.010 | 0.014 | 0.019 |
| 4 | AT1G22840 | *0.007* | *0.004* | *0.004* | *0.004* |
| 4 | AT1G22840 | *0.007* | *0.004* | *0.004* | *0.004* |
| 6 | AT1G52300 + intron | 0.054 | 0.057 | 0.103 | 0.192 |
| 6 | AT1G52300 + intron | 0.074 | 0.052 | 0.076 | 0.211 |
| 7 | AT1G52300 | 0.011 | 0.008 | 0.011 | 0.018 |

TABLE 11-continued

| Promoter Sequence (SEQ ID NO) | Gene from which promoter is derived ("+intron" is listed where the first intron from coding sequence was added as described above) | Maturation | | | |
|---|---|---|---|---|---|
| | | epi-dermis | cortex | endo-dermis | stele |
| 7 | AT1G52300 | 0.015 | 0.013 | 0.019 | 0.041 |
| 9 | AT4G37830 + intron | 0.097 | 0.111 | 0.158 | 0.259 |
| 9 | AT4G37830 + intron | 0.027 | 0.030 | 0.042 | 0.067 |
| 10 | AT4G37830 | *0.007* | *0.004* | *0.005* | *0.004* |
| 10 | AT4G37830 | *0.007* | *0.004* | *0.004* | *0.004* |
| 12 | AT3G08580 | 0.175 | 0.162 | 0.221 | 0.470 |
| 12 | AT3G08580 | 0.327 | 0.327 | 0.457 | 0.846 |
| 14 | AT1G51650 + intron | 0.169 | 0.160 | 0.259 | 0.432 |
| 14 | AT1G51650 + intron | 0.142 | 0.104 | 0.161 | 0.267 |
| 15 | AT1G51650 | *0.006* | *0.004* | *0.004* | *0.005* |
| 15 | AT1G51650 | *0.006* | *0.004* | *0.004* | *0.005* |
| 17 | AT3G48140 + intron | 0.021 | 0.014 | 0.016 | 0.024 |
| 17 | AT3G48140 + intron | 0.012 | 0.008 | 0.009 | 0.015 |
| 18 | AT3G48140 | *0.008* | *0.006* | 0.006 | 0.006 |
| 18 | AT3G48140 | 0.010 | 0.006 | 0.006 | 0.007 |
| 20 | At3G08610 + intron | 0.014 | 0.011 | 0.015 | 0.023 |
| 20 | At3G08610 + intron | 0.014 | 0.010 | 0.013 | 0.020 |
| 21 | At3G08610 | *0.007* | *0.005* | *0.005* | *0.006* |
| 21 | At3G08610 | *0.007* | *0.005* | *0.005* | *0.006* |
| 22 | AT3G62250 | 0.022 | 0.014 | 0.018 | 0.074 |
| 22 | AT3G62250 | 0.015 | 0.013 | 0.016 | 0.040 |
| 24 | AT4G05320 (UBQ10) | 0.468 | 0.488 | 0.62 | 0.819 |
| 24 | AT4G05320 (UBQ10) | 0.291 | 0.386 | 0.469 | 0.626 |

Example 10

Expression Testing of Regulatory Polynucleotides in Aerial Tissue of Stably Transformed *Arabidopsis*

Expression of GFP in aerial tissue of stably transformed *Arabidopsis* was assessed by qRT-PCR in two homozygous T3 lines of some of the regulatory polynucleotides that were demonstrated to confer significant expression in all 14 tissue-zone ROIs of the root. T3 seeds from each line were grown on MS agar plates. After 7-11 days the aerial portions of approximately 10 plants were collected in triplicate for RNA extraction and cDNA synthesis. Tissue was homogenized in liquid nitrogen via bead milling and total RNA was extracted using the Allprep DNA/RNA kit (Qiagen). cDNA was generated from total RNA using the Superscript VILO cDNA synthesis kit (Invitrogen) per the manufacturer's instructions. Multiplex qPCR TaqMan® assays were conducted using either the CFX96 Real-Time PCR Detection System or the iCycler iQ Real-Time PCR Detection System (both instruments are from Bio-Rad Laboratories) with primers and probes specific for GFP and the "housekeeping" gene UBC9. Three technical qRT-PCR replicates were performed on each biological replicate, and data was processed using CFX Manager software (Bio-Rad).

To determine relative GFP expression level, PCR reaction efficiency was calculated using LinRegPCR software (Ruijter) and verified using a standard curve based method. Ct and baseline threshold values were obtained from the CFX Manager software. Data analysis was performed using the statistics package R, available at the R Project for Statistical Computing. After correcting the Ct values for reaction efficiency, the relative GFP expression was calculated by subtracting the Ct of the UBC control from that of GFP, followed by averaging across all replicates. To assess statistical significance of the data, the relative GFP expression of each line was compared to that determined from non-transgenic *Arabidopsis* ecotype Columbia seedlings using a one-tailed Welch's t-test. All statistical analysis was performed on the corrected Ct values, but these values were exponentiated to a linear expression scale for presentation. To normalize the linear expression scale, the data was expressed relative to a 35S-promoter control that was included in all experiments. The 35S-promoter control value was set to 100 on this scale.

Aerial expression data for regulatory polynucleotides that drove constitutive expression in *Arabidopsis* roots is shown in Table 12 (expression data for the regulatory region from the UBQ10 gene (see Example 8) is also shown for comparison). All expression measurements were statistically significant ($p<0.01$). These data show that regulatory polynucleotides that drove constitutive GFP expression in *Arabidopsis* roots also drove GFP expression in *Arabidopsis* aerial tissue.

TABLE 12

| Gene from which promoter is derived ("+intron" is listed where the first intron from coding sequence was added as described above) | Promoter Sequence (SEQ ID NO) | Relative Expression |
|---|---|---|
| AT4G05320 (UBQ 10) | 24 | 0.66 |
| AT4G05320 (UBQ 10) | 24 | 0.16 |
| AT1G52300 + intron | 6 | 0.03 |
| AT1G52300 + intron | 6 | 0.04 |
| AT4G37830 + intron | 9 | 0.10 |
| AT4G37830 + intron | 9 | 0.03 |
| AT3G62250 | 22 | 0.01 |
| AT3G62250 | 22 | 0.01 |

Thus, the methods disclosed herein are useful to identify regulatory polynucleotides that are capable of regulating constitutive expression of an operably linked polynucleotide.

While the invention has been described in detail and with reference to specific embodiments thereof, it will be apparent to one skilled in the art that various changes and modifications can be made without departing from the spirit and scope of the invention.

The invention claimed is:

1. A regulatory polynucleotide comprising a nucleic acid molecule of SEQ ID NOs: 9 wherein the nucleic acid molecule is capable of regulating transcription of an operably linked transcribable polynucleotide molecule.

2. A recombinant polynucleotide construct comprising the regulatory polynucleotide of claim 1 operably linked to a transcribable polynucleotide molecule.

3. The recombinant polynucleotide construct of claim 2, wherein the transcribable polynucleotide molecule encodes a protein of agronomic interest.

4. The recombinant polynucleotide construct of claim 2, wherein the transcribable polynucleotide molecule is operably linked to a 3' transcription termination polynucleotide molecule.

5. A chimeric polynucleotide molecule comprising the regulatory polynucleotide of claim 1 operably linked to a second polynucleotide molecule capable of regulating transcription of an operably linked polynucleotide molecule.

6. The chimeric polynucleotide of claim 5, wherein the second polynucleotide molecule is selected from the group consisting of a cis-element, an enhancer element, and an intron.

7. The chimeric polynucleotide of claim 6, wherein the second polynucleotide molecule comprises an intron.

8. A transgenic host cell comprising the recombinant polynucleotide construct of claim 2.

9. The transgenic host cell of claim 8, wherein the host cell is a plant cell.

10. A transgenic plant stably transformed with the recombinant polynucleotide construct of claim 2.

11. The transgenic plant of claim 10, wherein the plant is selected from the group consisting of a monocotyledonous and a dicotyledonous plant.

12. The transgenic plant of claim 11, wherein the plant is a monocotyledonous plant selected from the group consisting of wheat, corn, rice, turf grass, millet, sorghum, switchgrass, miscanthus, sugarcane, and Brachypodium.

13. transgenic plant of claim 11, wherein the plant is a dicotyledonous plant selected from the group consisting of soybean, cotton, canola, and potato.

14. A seed produced by the transgenic plant of claim 10, wherein said seed comprises said recombinant polynucleotide construct.

15. A method of directing expression of a transcribable polynucleotide molecule in a host cell comprising:
(a) introducing the recombinant polynucleotide construct of claim 2 into a host cell to produce a transgenic host cell; and
(b) selecting a transgenic host cell exhibiting expression of the transcribable polynucleotide molecule.

16. The method of claim 15, wherein the transcribable polynucleotide molecule is selected from the group consisting of a coding sequence and a functional RNA.

17. The method of claim 15, wherein the host cell is a plant cell.

18. The method of claim 17, further comprising regenerating a plant comprising the introduced recombinant polynucleotide construct.

19. A method of directing expression of a transcribable polynucleotide molecule in a plant comprising:
(a) introducing the recombinant polynucleotide construct of claim 2 into a plant cell;
(b) regenerating a plant from the plant cell; and
(c) selecting a transgenic plant exhibiting expression of the transcribable polynucleotide molecule.

20. The method of claim 19, wherein the transcribable polynucleotide molecule is selected from the group consisting of a coding sequence and a functional RNA.

* * * * *

SEQUENCE LISTING

<160> NUMBER OF SEQ ID NOS: 24

<210> SEQ ID NO 1
<211> LENGTH: 1205
<212> TYPE: DNA
<213> ORGANISM: Arabidopsis thaliana

<400> SEQUENCE: 1

```
gttttataac cattcaccta acaaaaatga aatggaaaaa gaaagagag caaataagag      60 gaggagaaga agaagacttt tgcaaaagc caagagtcat acctattagt ctattacata    120
aggtgtgatg ttttttttg ctgtcacatt ccatctgacc taccaaagct ctcaaagtgg    180
agcatctatt gtgtcttggt atagagtcac gattagataa atatacaaca ccatatgtac    240
ttgtgtcaaa ttataaatat ttgaaacagt aagcaaccag taattcgata aagacgtcta    300
caagcatcta cacatctaaa ttgattaaaa caaaacacct ttaaatatag tgtttatgaa    360
gtcaaatctt caccttgatt attctaaaac aatggttgga gtaatgttgc tgaatgttga    420
gtgagaattg acatttgaga gtaactttca ctataatgaa ctggatgata agttgatcc    480 gataataatt gaatttacca tgaatggtat cacaagatac atgtatagaa gacagtggtg    540
ttacttgtta cgcaaaatta aaaatgagc atactattgc agttactttg gatttattaa    600
ggaaaattat ggtttgacaa caacaataat acaaaatctt atgaaaatta aataaaaga    660 aaaacaaatt tggctattgg caaagctcat tggctgtcaa aaggaatata tacaaaatct    720
gctacgttgc agtcttgcgt gcaccggccc agcccatagg attagagtat taaacctcga    780
atattccatc agcctgcgcg tgaatccaag cgccattagt ttccccaaat cagttcttaa    840
tcctacccat aaacgatggg taaaaatggt aaataagaaa gaaagtaaag tacaatatag    900
taatattaat tagtgaatct aatctattag ccttttttccc aagaaaaaat ctcagccact    960
cgatcatatt ttcaattttc atcatcacgt tcttcttctc ttttaaataa ccctaaatcc   1020
tcaccaaacc caaaccctca ctcactatt tcacattctc ttctctctcg atatcatcta   1080
aatctctctc gatctcaatt tcgcaaacag gtaagcttct cgctcttgtt gatctgcgat   1140
tcttcgattt attgttcttt cgttgatact ttttgaatct gatcgtaatt ttggtttgtg   1200
taggt                                                               1205
```

<210> SEQ ID NO 2
<211> LENGTH: 1107
<212> TYPE: DNA
<213> ORGANISM: Arabidopsis thaliana

<400> SEQUENCE: 2

```
gttttataac cattcaccta acaaaaatga aatggaaaaa gaaagagag caaataagag      60 gaggagaaga agaagacttt tgcaaaagc caagagtcat acctattagt ctattacata    120
aggtgtgatg ttttttttg ctgtcacatt ccatctgacc taccaaagct ctcaaagtgg    180
agcatctatt gtgtcttggt atagagtcac gattagataa atatacaaca ccatatgtac    240
ttgtgtcaaa ttataaatat ttgaaacagt aagcaaccag taattcgata aagacgtcta    300
caagcatcta cacatctaaa ttgattaaaa caaaacacct ttaaatatag tgtttatgaa    360
gtcaaatctt caccttgatt attctaaaac aatggttgga gtaatgttgc tgaatgttga    420
gtgagaattg acatttgaga gtaactttca ctataatgaa ctggatgata agttgatcc    480 gataataatt gaatttacca tgaatggtat cacaagatac atgtatagaa gacagtggtg    540
ttacttgtta cgcaaaatta aaaatgagc atactattgc agttactttg gatttattaa    600
ggaaaattat ggtttgacaa caacaataat acaaaatctt atgaaaatta aataaaaga    660 aaaacaaatt tggctattgg caaagctcat tggctgtcaa aaggaatata tacaaaatct    720
gctacgttgc agtcttgcgt gcaccggccc agcccatagg attagagtat taaacctcga    780
atattccatc agcctgcgcg tgaatccaag cgccattagt ttccccaaat cagttcttaa    840
tcctacccat aaacgatggg taaaaatggt aaataagaaa gaaagtaaag tacaatatag    900
```

```
taatattaat tagtgaatct aatctattag cctttttccc aagaaaaaat ctcagccact    960
cgatcatatt ttcaatttc atcatcacgt tcttcttctc ttttaaataa ccctaaatcc   1020
tcaccaaacc caaaccctca ctcactattt tcacattctc ttctctctcg atatcatcta   1080
aatctctctc gatctcaatt tcgcaaa                                       1107
```

<210> SEQ ID NO 3
<211> LENGTH: 776
<212> TYPE: DNA
<213> ORGANISM: Arabidopsis thaliana

<400> SEQUENCE: 3

```
ttatatacaa caagttttaa ttgcatgatt tcctgtaaac ataagtttac atgaactagg     60
ggatggtcct tcgcaagtat gagtaacaag cataaacagc attatatatg aaataaatat    120
gagcccacct aaacccatta agggcccatt aagattggag atactgcttt tttaagagag    180 gtcactttt ccacagtgaa accctaagga aacttcggca agctccagag aaacgagagt     240
tccgtaatca ttttctcttg ttgttcctga tcgcgtagct caagcgaaaa aacaggtttt    300
cactcatcga tctctctcac tcttgaattc tatttctatg gttgattttc gcaatttatc    360 tgaatttta tcgggccttt gttttacatc gctttataat cgatttgttc atgttaatca    420
aaaatctctg atgtgatctg gttaacggat tcttcgatta gatcatagat ctgatccaat    480
aacctcgatg tcttactcgt gtttatcctt aaatcttcag ctcaatgcat gtgacgaatt    540
tctgaggttt ttatatacaa cttttcgcat ttttgtggaa cttgattctc gaattctaag    600
taatgataca acaatgattt gagctagttg cgtcacagat tctcattttt tcttgaaatt    660
gcgtgaaatt agaaaacact gttgctcaat ggtttctatt gttttcgtag cttttgtaga    720
atgtgatttg cgtcacattg ttgctcaaca cttgaccttg ttgttttaat ataggt        776
```

<210> SEQ ID NO 4
<211> LENGTH: 292
<212> TYPE: DNA
<213> ORGANISM: Arabidopsis thaliana

<400> SEQUENCE: 4

```
ttatatacaa caagttttaa ttgcatgatt tcctgtaaac ataagtttac atgaactagg     60
ggatggtcct tcgcaagtat gagtaacaag cataaacagc attatatatg aaataaatat    120
gagcccacct aaacccatta agggcccatt aagattggag atactgcttt tttaagagag    180 gtcactttt ccacagtgaa accctaagga aacttcggca agctccagag aaacgagagt     240
tccgtaatca ttttctcttg ttgttcctga tcgcgtagct caagcgaaaa aa            292
```

<210> SEQ ID NO 5
<211> LENGTH: 776
<212> TYPE: DNA
<213> ORGANISM: Arabidopsis thaliana

<400> SEQUENCE: 5

```
ttatatacaa caagttttaa ttgcatgatt tcctgtaaac ataagtttac atgaactagg     60
ggatggtcct tcgcaagtat gagtaacaag cataaacagc attatatatg aaataaatat    120
gagcccacct aaacccatta agggcccatg caagacccct cctctatata aggaagttca    180
tttcatttgg agagggtgaa accctaagga aacttcggca agctccagag aaacgagagt    240
tccgtaatca ttttctcttg ttgttcctga tcgcgtagct caagcgaaaa aacaggtttt    300
```

```
cactcatcga tctctctcac tcttgaattc tatttctatg gttgattttc gcaatttatc      360 tgaatttta tcgggccttt gttttacatc gctttataat cgatttgttc atgttaatca       420
aaaatctctg atgtgatctg gttaacggat tcttcgatta gatcatagat ctgatccaat      480
aacctcgatg tcttactcgt gtttatcctt aaatcttcag ctcaatgcat gtgacgaatt      540
tctgaggttt ttatatacaa cttttcgcat ttttgtggaa cttgattctc gaattctaag      600
taatgataca acaatgattt gagctagttg cgtcacagat tctcattttt tcttgaaatt      660
gcgtgaaatt agaaaacact gttgctcaat ggtttctatt gttttcgtag cttttgtaga      720
atgtgatttg cgtcacattg ttgctcaaca cttgaccttg ttgttttaat ataggt          776
```

<210> SEQ ID NO 6
<211> LENGTH: 1203
<212> TYPE: DNA
<213> ORGANISM: Arabidopsis thaliana

<400> SEQUENCE: 6

```
cgacacataa aattaaaac aaatcaaaaa caaacaattg atcaaattct taagaaataa       60
aaaaggtgaa taacatacat gtagactttt atcacaccaa aaaaaacaca cacacatgta      120 gagaatttt gtggtatttt gtcttgtcct cctaaaatca tatgctatgt gaaagtataa       180
catcgacttg aatattagaa aattgggaaa ctcaaacaac tagtatataa aatattttgt      240
atgtgaacca ttgttctact tacatgttgt gattgtaaaa tttatggagg caaagagaga      300
aaaatgtacc atgaacgagg aatgatggat taatggttcc ttgacttgag aagaaggttt      360
atgactctat cgtgtccaaa atcaaaactt ctcttgacga tctcttggga gcttcttttg      420
agactcaaag atatattaaa ggaaaataca agctgaaaaa aaagtaaaaa tcaaaatccc      480
tgtaatcgac gaccaaaaaa aaagatttat tgatacttac ttggaggaaa aaaccaacat      540
ttatggaata aattgttccc caagtattca attaatactt cagttgtgaa aatttgagac      600
tcaaatcaca aattttctta atatattttt tttttttatca tccgatttta atctgaggaa      660
tgttgtttac ataaatgata ggaaacggtt tagtgcaaaa ttttctcaat ataattgtta      720
ttgcaattag ttttttttatt ttttattttt tattttggt ttaaaagtta aaacaacaca      780
atttaataaa gtataaaata taatactcac ctaaattatt gttacaaatt ctattgtaaa      840
ccggcacaac aatggtaaaa agtaaaaaca aatcgtttcc tggttaagtc ttcgaaatga      900
gtcccgcaca aaaaggctta ttaagtatta aggcccatgg gcctgactta tcgatccaat      960
aaagaattca caaccctaat aaaaaggacg aaacccctagc tttatataaa ctttgttaa      1020 cctaccgtcg tcacttcctt ctcttgaagc cggaaacctt aaggttttat atctgggaaa     1080
aaactcgcat ccgcttcagg tgatctacga ttctcctctc tatctttcta tttcatctct     1140
atgcttcgtt gatttcatta ctctgatatc tgttttatcg ctttgttttt gagattctca     1200
ggt                                                                     1203
```

<210> SEQ ID NO 7
<211> LENGTH: 1098
<212> TYPE: DNA
<213> ORGANISM: Arabidopsis thaliana

<400> SEQUENCE: 7

```
cgacacataa aattaaaac aaatcaaaaa caaacaattg atcaaattct taagaaataa       60
aaaaggtgaa taacatacat gtagactttt atcacaccaa aaaaaacaca cacacatgta      120 gagaatttt gtggtatttt gtcttgtcct cctaaaatca tatgctatgt gaaagtataa       180
```

```
catcgacttg aatattagaa aattgggaaa ctcaaacaac tagtatataa aatattttgt    240
atgtgaacca ttgttctact tacatgttgt gattgtaaaa tttatggagg caaagagaga    300
aaaatgtacc atgaacgagg aatgatggat taatggttcc ttgacttgag aagaaggttt    360
atgactctat cgtgtccaaa atcaaaactt ctccttgacga tctcttggga gcttcttttg    420
agactcaaag atatattaaa ggaaaataca agctgaaaaa aaagtaaaaa tcaaaatccc    480
tgtaatcgac gaccaaaaaa aaagatttat tgatacttac ttggaggaaa aaaccaacat    540
ttatggaata aattgttccc caagtattca attaatactt cagttgtgaa aatttgagac    600
tcaaatcaca aattttctta atatatttt tttttttatca tccgattta atctgaggaa    660 tgttgtttac ataaatgata ggaaacggtt tagtgcaaaa ttttctcaat ataattgtta    720
ttgcaattag tttttttatt tttattttt tattttggt ttaaaagtta aaacaacaca    780
atttaataaa gtataaaata taatactcac ctaaattatt gttacaaatt ctattgtaaa    840
ccggcacaac aatggtaaaa agtaaaaaca aatcgtttcc tggttaagtc ttcgaaatga    900
gtcccgcaca aaaaggctta ttaagtatta aggcccatgg gcctgactta tcgatccaat    960
aaagaattca caaccctaat aaaaaggacg aaacccctagc tttatataaa cttttgttaa    1020
cctaccgtcg tcacttcctt ctcttgaagc cggaaacctt aaggttttat atctgggaaa    1080
aaactcgcat ccgcttca                                                 1098

<210> SEQ ID NO 8
<211> LENGTH: 1203
<212> TYPE: DNA
<213> ORGANISM: Arabidopsis thaliana

<400> SEQUENCE: 8
cgacacataa aaattaaaac aaatcaaaaa caaacaattg atcaaattct taagaaataa     60
aaaaggtgaa taacatacat gtagactttt atcacaccaa aaaaaacaca cacacatgta    120 gagaatttt gtggtatttt gtcttgtcct cctaaaatca tatgctatgt gaaagtataa    180
catcgacttg aatattagaa aattgggaaa ctcaaacaac tagtatataa aatattttgt    240
atgtgaacca ttgttctact tacatgttgt gattgtaaaa tttatggagg caaagagaga    300
aaaatgtacc atgaacgagg aatgatggat taatggttcc ttgacttgag aagaaggttt    360
atgactctat cgtgtccaaa atcaaaactt ctcttgacga tctcttggga gcttcttttg    420
agactcaaag atatattaaa ggaaaataca agctgaaaaa aaagtaaaaa tcaaaatccc    480
tgtaatcgac gaccaaaaaa aaagatttat tgatacttac ttggaggaaa aaaccaacat    540
ttatggaata aattgttccc caagtattca attaatactt cagttgtgaa aatttgagac    600
tcaaatcaca aattttctta atatatttt tttttttatca tccgattta atctgaggaa    660 tgttgtttac ataaatgata ggaaacggtt tagtgcaaaa ttttctcaat ataattgtta    720
ttgcaattag tttttttatt tttatttt tattttggt ttaaaagtta aaacaacaca    780
atttaataaa gtataaaata taatactcac ctaaattatt gttacaaatt ctattgtaaa    840
ccggcacaac aatggtaaaa agtaaaaaca aatcgtttcc tggttaagtc ttcgaaatga    900
gtcccgcaca aaaaggctta ttaagtatta aggcccatgg gcctgactta tcgatccaat    960
aaagaattca gcaagaccct tcctctatat aaggaagttc atttcatttg gagaggttaa   1020
cctaccgtcg tcacttcctt ctcttgaagc cggaaacctt aaggttttat atctgggaaa   1080
aaactcgcat ccgcttcagg tgatctacga ttctcctctc tatctttcta tttcatctct   1140
```

```
atgcttcgtt gatttcatta ctctgatatc tgttttatcg ctttgttttt gagattctca   1200
ggt                                                                 1203

<210> SEQ ID NO 9
<211> LENGTH: 1205
<212> TYPE: DNA
<213> ORGANISM: Arabidopsis thaliana

<400> SEQUENCE: 9
tgcgagtggg cgaattccgg agcactctga ttggctgaaa aatagaaat agtagtgatg     60 ttgctcctcc tctcctcctc tattattaat ttttcgtcgt tcttcttctg aaagttgtgt   120 ggttttttaga ggtcaccaaa aaaaatctat tttgagatac taaaaatatt tcgttttgca  180
ttttgttgtg cagccatttg ttacacaggt tgaagcttat aactgaaaat tggattcaaa   240
gaatcgtaga tgaagaaatc gaagtgagtt gaatattttc tgaacatatg aaaattggaa   300 caagttttt ctcattttgc tagtttcctg tttttatgtt ttcttgactt taggagatga    360
catatggagg tgaactatac aaaggttgtt gcaacgataa cattctcctt aattcagttt   420
ttgcaactcg gttacaagca ctcagtggac ttttggccaa gacaattttt tttttttttt   480
ctctctctct aaaatgttat agatacgaat cctttgttga ataaggaaa aagttgaaca    540 tttgattaca cataagactt taacataatc caactttttt ttatatgaag ctacaaacaa   600
gatttaaaac atcaaagatt ccatctaaac ttcattcatc ttcaatcttc aacatccttc   660
aatgactagt atgtatgtac ataagtaaaa ttgttgataa gaaaacaaaa caatgatggg   720
ctaaaatagc ccataaaagg cccattaaac tggggttttag actttagatt caacgacgcc  780
agattagtga gtcacataac cctcttggaa agagtctcaa cacttgcaga gaaaagaac    840 aaggaagatc ccggaaacag gtaatttctc tcctctctat ttttaccatt ttccattgac   900
gacgatctag gttttctgat ttgatttttgg agaacgcctc gatgagttta tagattcgta  960
gattggtttt gagattcagt ataatttcac ccgattcca attttttgaac cgatacctaa   1020 ttttgaattg atttggtaga tcgattggtc aaatttgaaa ttgatttttc tccataatat   1080
ctgaagcgtc ttattggatc aaatctacaa catttctctg ttgaaaggat cgattttttt   1140
tttcttggaa catgataact tttgattatt catcaaagtt ttgttctttt taatatttca   1200
caggt                                                               1205

<210> SEQ ID NO 10
<211> LENGTH: 857
<212> TYPE: DNA
<213> ORGANISM: Arabidopsis thaliana

<400> SEQUENCE: 10
tgcgagtggg cgaattccgg agcactctga ttggctgaaa aatagaaat agtagtgatg     60 ttgctcctcc tctcctcctc tattattaat ttttcgtcgt tcttcttctg aaagttgtgt   120 ggttttttaga ggtcaccaaa aaaaatctat tttgagatac taaaaatatt tcgttttgca  180
ttttgttgtg cagccatttg ttacacaggt tgaagcttat aactgaaaat tggattcaaa   240
gaatcgtaga tgaagaaatc gaagtgagtt gaatattttc tgaacatatg aaaattggaa   300 caagttttt ctcattttgc tagtttcctg tttttatgtt ttcttgactt taggagatga    360
catatggagg tgaactatac aaaggttgtt gcaacgataa cattctcctt aattcagttt   420
ttgcaactcg gttacaagca ctcagtggac ttttggccaa gacaattttt tttttttttt   480
ctctctctct aaaatgttat agatacgaat cctttgttga ataaggaaa aagttgaaca    540
```

| | |
|---|---|
| tttgattaca cataagactt taacataatc caacttttt ttatatgaag ctacaaacaa | 600 |
| gatttaaaac atcaaagatt ccatctaaac ttcattcatc ttcaatcttc aacatccttc | 660 |
| aatgactagt atgtatgtac ataagtaaaa ttgttgataa gaaaacaaaa caatgatggg | 720 |
| ctaaaatagc ccataaaagg cccattaaac ttgggtttag actttagatt caacgacgcc | 780 |
| agattagtga gtcacataac cctcttggaa agagtctcaa cacttgcaga gaaaaagaac | 840 |
| aaggaagatc ccggaaa | 857 |

<210> SEQ ID NO 11
<211> LENGTH: 1205
<212> TYPE: DNA
<213> ORGANISM: Arabidopsis thaliana

<400> SEQUENCE: 11

| | |
|---|---|
| tgcgagtggg cgaattccgg agcactctga ttggctgaaa aaatagaaat agtagtgatg | 60 |
| ttgctcctcc tctcctcctc tattattaat ttttcgtcgt tcttcttctg aaagttgtgt | 120 |
| ggttttaga ggtcaccaaa aaaaatctat tttgagatac taaaaatatt tcgttttgca | 180 |
| ttttgttgtg cagccatttg ttacacaggt tgaagcttat aactgaaaat tggattcaaa | 240 |
| gaatcgtaga tgaagaaatc gaagtgagtt gaatattttc tgaacatatg aaaattggaa | 300 |
| caagtttttt ctcatttgc tagtttcctg ttttatgtt ttcttgactt taggagatga | 360 |
| catatggagg tgaactatac aaaggttgtt gcaacgataa cattctcctt aattcagttt | 420 |
| ttgcaactcg gttacaagca ctcagtggac ttttggccaa gacaattttt ttttttttt | 480 |
| ctctctctct aaaatgttat agatacgaat cctttgttga ataaggaaa aagttgaaca | 540 |
| tttgattaca cataagactt taacataatc caacttttt ttatatgaag ctacaaacaa | 600 |
| gatttaaaac atcaaagatt ccatctaaac ttcattcatc ttcaatcttc aacatccttc | 660 |
| aatgactagt atgtatgtac ataagtaaaa ttgttgataa gaaaacaaaa caatgatggg | 720 |
| ctaaaatagc ccataaaagg caagacccctt cctctatata aggaagttca tttcatttgg | 780 |
| agaggagtga gtcacataac cctcttggaa agagtctcaa cacttgcaga gaaaaagaac | 840 |
| aaggaagatc ccggaaacag gtaatttctc tcctctctat ttttaccatt ttccattgac | 900 |
| gacgatctag gttttctgat ttgattttgg agaacgcctc gatgagttta tagattcgta | 960 |
| gattggtttt gagattcagt ataatttcac ccggattcca atttttgaac cgatacctaa | 1020 |
| ttttgaattg atttggtaga tcgattggtc aaatttgaaa ttgattttc tccataatat | 1080 |
| ctgaagcgtc ttattggatc aaatctacaa catttctctg ttgaaaggat cgattttttt | 1140 |
| tttcttggaa catgataact tttgattatt catcaaagtt ttgttctttt taatatttca | 1200 |
| caggt | 1205 |

<210> SEQ ID NO 12
<211> LENGTH: 1200
<212> TYPE: DNA
<213> ORGANISM: Arabidopsis thaliana

<400> SEQUENCE: 12

| | |
|---|---|
| caaatatcat attcatatag aagaaaataa acaaagttgt aaaaatctgg catttaaaat | 60 |
| aaaattgaac acttcaattt atttcctttc ataataataa ttttggcata agatatttgc | 120 |
| aaattgatct ggttcggtat ggtcgacaaa ataattttcc acgctaccct tccagccgtc | 180 |
| cattcactat ttgccctcaa cgttaccaaa taacggtcca gattcctagg gcaagatcta | 240 |

```
acggttagca agtaaagtcg taccatcaga aagaataaca attctttcac aaagtaaaca      300
taaccaacgg ttaacaagtt cttagggtta aatcagtaag atccaacgga tattaaattg      360
caaggcccaa atagttttt tgcagcagat aataactcgt ccccactggc gagtgacgac       420
cgagactctg tgaccctatt tttcgagacg ataaaagggc aaacaatcgc tcttttcaaa      480
gctcgcctct tcaccacaga gaaaacttcg tctctcttct ctgcttcgcc ctctcatttc      540
ctgtgagata aaggcggagt ctctctccag ttattttgct catccatcga ttcttaggta      600
tgactcgttt ctctcagatc tgtgattctt tataatctcg tcgttcttca aatcattgtt      660
atattcgttt cttcgatctg tgttttttag atctgtaagg taaatgagac gtttcgatct      720
gtagatctga ttgttatatt gatagattat gttatctgct ttgcttaaag tccgatcgga     780
atgttttgtg ctcattgtcg aatatctgat gtatcggttt catagatctg cttcttttg       840 tgcgtttcgt tgatctgata atcttctagt gatcaaaatc gtttggatct gttgacttta      900
gtttaaaatg tatccgatct gatgtcgagg cttcattatt ggaagttgtt attgttgtaa      960
tcctgattta agttgctgtt cttaaattta tatgatcttt gcgttataat atgacatggt     1020
agatcttggt tcatggttca ctgttttcca ataaacttgg tttgtttggt tggatagcgt     1080
tctgtgatac gaccatgtct tgtgttggat aagaattctc tgaatttcct tggctggttt    1140
gtagtatgtt attcacgtct ggtttctcat caatgattat gtgattttgc agagttcaaa    1200
```

<210> SEQ ID NO 13
<211> LENGTH: 1200
<212> TYPE: DNA
<213> ORGANISM: Arabidopsis thaliana

<400> SEQUENCE: 13

```
caaatatcat attcatatag aagaaaataa acaaagttgt aaaaatctgg catttaaaat       60
aaaattgaac acttcaattt atttcctttc ataataataa ttttggcata agatatttgc      120
aaattgatct ggttcggtat ggtcgacaaa ataattttcc acgctaccct tccagccgtc      180
cattcactat ttgccctcaa cgttaccaaa taacggtcca gattcctagg gcaagatcta      240
acggttagca agtaaagtcg taccatcaga aagaataaca attctttcac aaagtaaaca      300
taaccaacgg ttaacaagtt cttagggtta aatcagtaag atccaacgga tattaaattg      360
caaggcccaa atagttttt tgcagcagat aataactcgt ccccactggc gagtgacgac       420
cgagactctg tgaccctatt tttcgagacg ataaaagggc aaacaatcgc tcttttcaaa      480
gctcgcctct tcaccacaga gaaaacttcg tctctcttct ctgcttcgcc ctctcatttc      540
ctgtgagata aaggcggagt ctctctccag ttattttgct catccatcga ttcttaggta      600
tgactcgttt cgcaagaccc ttcctctata taaggaagtt catttcattt ggagagggtt     660
atattcgttt cttcgatctg tgttttttag atctgtaagg taaatgagac gtttcgatct      720
gtagatctga ttgttatatt gatagattat gttatctgct ttgcttaaag tccgatcgga     780
atgttttgtg ctcattgtcg aatatctgat gtatcggttt catagatctg cttcttttg       840 tgcgtttcgt tgatctgata atcttctagt gatcaaaatc gtttggatct gttgacttta      900
gtttaaaatg tatccgatct gatgtcgagg cttcattatt ggaagttgtt attgttgtaa      960
tcctgattta agttgctgtt cttaaattta tatgatcttt gcgttataat atgacatggt     1020
agatcttggt tcatggttca ctgttttcca ataaacttgg tttgtttggt tggatagcgt     1080
tctgtgatac gaccatgtct tgtgttggat aagaattctc tgaatttcct tggctggttt    1140
gtagtatgtt attcacgtct ggtttctcat caatgattat gtgattttgc agagttcaaa    1200
```

<210> SEQ ID NO 14
<211> LENGTH: 1569
<212> TYPE: DNA
<213> ORGANISM: Arabidopsis thaliana

<400> SEQUENCE: 14

| | | | | | |
|---|---|---|---|---|---|
| ggaggaggat | atgattgttg | cttcaacaac | tatatatgga | tttgataaca | atcctttatc | 60 |
| ctcggaagat | aaaccaaatt | tcttaccaaa | cccaccaaaa | taagtaatta | ccagtgttct | 120 |
| tcttctaaag | acttctataa | accaaaacaa | gatcacatat | aatcattaac | ttaaagcaaa | 180 |
| acccaaagtc | ttgttttatt | tgttagtcag | ctcaaccatc | tttatctgaa | actaaactgt | 240 |
| ttctctcttc | tttgtttctg | acaagtcaat | gagattggtg | tcttctctct | gttgcacatt | 300 |
| taatattaac | ttttgaaaaa | ctacaaaacg | aaacaaaaca | aagaaaagca | gacatttaca | 360 |
| cgaaattatg | cagacatata | cacgaaattc | aatctacctg | aaaatgagaa | taagttttga | 420 |
| gtaaatttcg | tggagactcc | tggaaataag | tttgtttgtt | ttcctatttt | tatgtaactt | 480 |
| cgcttaaatt | tctaattgcc | taatcaaggt | attaaaatag | caaagcttgg | tttggctcag | 540 |
| tcttcgcgta | aactccaaga | aacaatcata | aaaacaaata | aaaaagacaa | gaaaccaaaa | 600 |
| aaaaaaaaaa | agttgagaga | tttcagtaga | tgaaagttgg | atagaagatt | cgtgtagtta | 660 |
| gctacttaat | gggccgttaa | aatatttaat | aaggcccatt | gggtctaaac | tgtgttagga | 720 |
| ttactagggc | acagaatcgg | tctctgtccc | atttcgcgaa | ctttctcctt | agaatcggaa | 780 |
| cggacgaaga | aggaagacaa | ggaagaagat | cggagcaggt | aagccttttc | gatcctttaa | 840 |
| tcgtcgatgt | tggatcttag | atctggattc | ttcacgttct | tgtgttctcg | attcctgatt | 900 |
| tgttttttgag | taatttgttg | gaataatctg | atttcctaaa | agttatcgga | attaagtgga | 960 |
| aagtgaatca | tctgcttctg | gatttgatct | tcgattttgc | atttaacctt | tcctctgctt | 1020 |
| ctggatttga | tcagttcaat | actatcttca | tacaatgttg | ttatgtccaa | attgttgaat | 1080 |
| ttttcattta | gagttagctt | cagagaaaac | aacaaaacta | gtagtatgtg | tgaaacaaga | 1140 |
| acatgaagaa | gatggaaagc | tgattgggaa | cattgcattt | agatgtcttt | tctcgtttat | 1200 |
| gtttggatct | gaattcttca | tgttcttgtt | gtgtgtcatt | gaaattgttg | gaatacgtag | 1260 |
| atatcagagt | aggtcatttt | gggaaagcta | ttgaatttaa | gaggaagatg | aatcatttta | 1320 |
| acaagctcca | tcgattttgc | gcttaatctg | tctctcttct | gcttctggat | ttgattaatt | 1380 |
| tcattctatt | ttgttttctc | ataagttgtt | gttatgttca | aattgttgaa | tttggaatga | 1440 |
| tttcatttct | caaatagggt | ttactgagac | aatgattcca | gatttagtct | atctgaaaat | 1500 |
| ggttcagctt | tcttcttgtt | gatccatttg | tctaacattc | tctcatgttt | tgttttttcc | 1560 |
| ttgacaggt | | | | | 1569 |

<210> SEQ ID NO 15
<211> LENGTH: 815
<212> TYPE: DNA
<213> ORGANISM: Arabidopsis thaliana

<400> SEQUENCE: 15

| | | | | | |
|---|---|---|---|---|---|
| ggaggaggat | atgattgttg | cttcaacaac | tatatatgga | tttgataaca | atcctttatc | 60 |
| ctcggaagat | aaaccaaatt | tcttaccaaa | cccaccaaaa | taagtaatta | ccagtgttct | 120 |
| tcttctaaag | acttctataa | accaaaacaa | gatcacatat | aatcattaac | ttaaagcaaa | 180 |
| acccaaagtc | ttgttttatt | tgttagtcag | ctcaaccatc | tttatctgaa | actaaactgt | 240 |

```
ttctctcttc tttgtttctg acaagtcaat gagattggtg tcttctctct gttgcacatt      300
taatattaac ttttgaaaaa ctacaaaacg aaacaaaaca agaaaaagca gacatttaca      360
cgaaattatg cagacatata cacgaaattc aatctacctg aaaatgagaa taagttttga      420
gtaaatttcg tggagactcc tggaaataag tttgtttgtt ttcctatttt tatgtaactt      480
cgcttaaatt tctaattgcc taatcaaggt attaaaatag caaagcttgg tttggctcag      540
tcttcgcgta aactccaaga aacaatcata aaaacaaata aaaagacaa gaaaccaaaa       600 aaaaaaaaaa agttgagaga tttcagtaga tgaaagttgg atagaagatt cgtgtagtta      660
gctacttaat gggccgttaa aatatttaat aaggcccatt gggtctaaac tgtgttagga     720
ttactagggc acagaatcgg tctctgtccc atttcgcgaa cttctccctt agaatcggaa      780
cggacgaaga aggaagacaa ggaagaagat cggag                                815

<210> SEQ ID NO 16
<211> LENGTH: 1569
<212> TYPE: DNA
<213> ORGANISM: Arabidopsis thaliana

<400> SEQUENCE: 16
ggaggaggat atgattgttg cttcaacaac tatatatgga tttgataaca atcctttatc       60
ctcggaagat aaaccaaatt tcttaccaaa cccaccaaaa taagtaatta ccagtgttct      120
tcttctaaag acttctataa accaaaacaa gatcacatat aatcattaac ttaaagcaaa      180
acccaaagtc ttgttttatt tgttagtcag ctcaaccatc tttatctgaa actaaactgt      240
ttctctcttc tttgtttctg acaagtcaat gagattggtg tcttctctct gttgcacatt      300
taatattaac ttttgaaaaa ctacaaaacg aaacaaaaca agaaaaagca gacatttaca      360
cgaaattatg cagacatata cacgaaattc aatctacctg aaaatgagaa taagttttga      420
gtaaatttcg tggagactcc tggaaataag tttgtttgtt ttcctatttt tatgtaactt      480
cgcttaaatt tctaattgcc taatcaaggt attaaaatag caaagcttgg tttggctcag      540
tcttcgcgta aactccaaga aacaatcata aaaacaaata aaaagacaa gaaaccaaaa       600 aaaaaaaaaa agttgagaga tttcagtaga tgaaagttgg atagaagatt cgtgtagtta      660
gctacttaat gggccgttaa aatatttaat aaggcccatt gggtgcaaga cccttcctct      720
atataaggaa gttcatttca tttggagagg atttcgcgaa cttctccctt agaatcggaa      780
cggacgaaga aggaagacaa ggaagaagat cggagcaggt aagccttttc gatcctttaa      840
tcgtcgatgt tggatcttag atctggattc ttcacgttct tgtgttctcg attcctgatt      900
tgtttttgag taatttgttg gaataatctg atttcctaaa agttatcgga attaagtgga      960
aagtgaatca tctgcttctg gatttgatct tcgattttgc atttaacctt tcctctgctt     1020
ctggatttga tcagttcaat actatcttca tacaatgttg ttatgtccaa attgttgaat     1080
ttttcattta gagttagctt cagagaaaac aacaaaacta gtagtatgtg tgaaacaaga     1140
acatgaagaa gatggaaagc tgattgggaa cattgcattt agatgtcttt tctcgtttat     1200
gtttggatct gaattcttca tgttcttgtt gtgtgtcatt gaaattgttg gaatacgtag     1260
atatcagagt aggtcatttt gggaaagcta ttgaatttaa gaggaagatg aatcatttta     1320
acaagctcca tcgattttgc gcttaatctg tctctcttct gcttctggat ttgattaatt     1380
tcattctatt tgttttctc ataagttgtt gttatgttca aattgttgaa tttggaatga     1440
tttcatttct caaatagggt ttactgagac aatgattcca gatttagtct atctgaaaat     1500
ggttcagctt tcttcttgtt gatccatttg tctaacattc tctcatgttt ttgttttttcc     1560
``` ttgacaggt                                                                   1569

<210> SEQ ID NO 17
<211> LENGTH: 1203
<212> TYPE: DNA
<213> ORGANISM: Arabidopsis thaliana

<400> SEQUENCE: 17
aaaattaata ttaataaaat aaatggcttt ttggcaagac ggatttggag gaatgggttt     60
ttggatcaac attaagaaaa agtaaaatat aattaatcca ccgtttcaat acgggttaaa    120
tctttaattt attattttt aagactacta atattaaaca tatcaaatca tcctaattta    180
gaaaagatta tataaaacca aaaatgttat gtggtatgta taatgttact atatataaaa    240
ttaaactata aaatatatat tagagaatga tacaatttac aaaactttta tatataataa    300
ataattctta aattttaaaa attactactt taaaaaaaat tcacggaacg ggtaaagaaa    360
ttatagaata ggttttatt ttggaattga gttatatggt ggatgtattt gaatcaatat    420
ttataaaatt ctaaaatatt attaatatga tgttttaata aggattaaaa cttcagtttt    480
ttaacaattg tcgcatagat tcgtggtata gcgttactta ataacaatta taaactgaaa    540
aatttaaata ttttataaaa ataaaattta caagttttaa tatatattaa ctttaaaata    600
taaatcgtcc cgcggtatac cgcggattaa aatctagttt gctataaaaa aagtaacgta    660
aaaattgttg ccaattagat attaccaata aagaaattta aaatatatgg gttgaaaaaa    720
gagaagaaga taagaatcgt atcttattac aacttgccaa tttgctatcg tttcgtaaca    780
gctaaacagt tcaaataaaa cggtgtctcg aaacactaaa tagacagatg tcaataccctc    840 attggattta agcataacgc ctcgctgcca attagaattc agcattccaa tttcatttta    900
ttttctcaca aaattctcca aaaaacctaa aagtcaaata aatataaagt gaggtctttt    960
ctacgtctct tcaacattct cagagaagcc gtcttcttcc tccttcaatc tctctcgttc   1020
gtatcatctg ctctgcgatt tcaggtacta cttcattttg atctttgatt ttccctaaat   1080
cgaaatccat cggttgattc tctgttgact acgtcttatt tctaaatcct tagatctaga   1140
ttcgattctt gtaagaatta gcctcgtgaa tcaatatgat aacgtgtttc attgttttta   1200
ggt                                                                 1203

<210> SEQ ID NO 18
<211> LENGTH: 1043
<212> TYPE: DNA
<213> ORGANISM: Arabidopsis thaliana

<400> SEQUENCE: 18
aaaattaata ttaataaaat aaatggcttt ttggcaagac ggatttggag gaatgggttt     60
ttggatcaac attaagaaaa agtaaaatat aattaatcca ccgtttcaat acgggttaaa    120
tctttaattt attattttt aagactacta atattaaaca tatcaaatca tcctaattta    180
gaaaagatta tataaaacca aaaatgttat gtggtatgta taatgttact atatataaaa    240
ttaaactata aaatatatat tagagaatga tacaatttac aaaactttta tatataataa    300
ataattctta aattttaaaa attactactt taaaaaaaat tcacggaacg ggtaaagaaa    360
ttatagaata ggttttatt ttggaattga gttatatggt ggatgtattt gaatcaatat    420
ttataaaatt ctaaaatatt attaatatga tgttttaata aggattaaaa cttcagtttt    480
ttaacaattg tcgcatagat tcgtggtata gcgttactta ataacaatta taaactgaaa    540

```
aatttaaata ttttataaaa ataaaattta caagttttaa tatatattaa ctttaaaata      600
taaatcgtcc cgcggtatac cgcggattaa aatctagttt gctataaaaa aagtaacgta      660
aaaattgttg ccaattagat attaccaata aagaaattta aaatatatgg gttgaaaaaa      720
gagaagaaga taagaatcgt atcttattac aacttgccaa tttgctatcg tttcgtaaca      780
gctaaacagt tcaaataaaa cggtgtctcg aaacactaaa tagacagatg tcaatacctc      840
attggattta agcataacgc ctcgctgcca attagaattc agcattccaa tttcattta      900 ttttctcaca aaattctcca aaaaacctaa aagtcaaata aatataaagt gaggtctttt      960
ctacgtctct tcaacattct cagagaagcc gtcttcttcc tccttcaatc tctctcgttc     1020
gtatcatctg ctctgcgatt tca                                             1043

<210> SEQ ID NO 19
<211> LENGTH: 1203
<212> TYPE: DNA
<213> ORGANISM: Arabidopsis thaliana

<400> SEQUENCE: 19
aaaattaata ttaataaaat aaatggcttt ttggcaagac ggatttggag gaatgggttt       60
ttggatcaac attaagaaaa agtaaaaatat aattaatcca ccgtttcaat acgggttaaa     120 tctttaatttt attatttttt aagactacta atattaaaca tatcaaatca tcctaattta    180
gaaaagatta tataaaacca aaaatgttat gtggtatgta taatgttact atatataaaa     240
ttaaactata aaatatatat tagagaatga tacaatttac aaaacttttta tatataataa    300 ataattctta aattttaaaa attactactt taaaaaaat tcacggaacg ggtaaagaaa      360
ttatagaata ggttttattt ttggaattga gttatatggt ggatgtattt gaatcaatat     420
ttataaaatt ctaaaatatt attaatatga tgtttttaata aggattaaaa cttcagtttt    480
ttaacaattg tcgcatagat tcgtggtata gcgttactta ataacaatta taaactgaaa     540
aatttaaata ttttataaaa ataaaattta caagttttaa tatatattaa ctttaaaata     600
taaatcgtcc cgcggtatac cgcggattaa aatctagttt gctataaaaa aagtaacgta     660
aaaattgttg ccaattagat attaccaata aagaaattta aaatatatgg gttgaaaaaa     720
gagaagaaga taagaatcgt atcttattac aacttgccaa tttgctatcg tttcgtaaca     780
gctaaacagt tcaaataaaa cggtgtctcg aaacactaaa tagacagatg tcaatacctc     840
attggattta agcataacgc ctcgctgcca attagaattc aggcaagacc cttcctctat     900
ataaggaagt tcatttcatt tggagaggaa aagtcaaata aatataaagt gaggtctttt     960
ctacgtctct tcaacattct cagagaagcc gtcttcttcc tccttcaatc tctctcgttc    1020
gtatcatctg ctctgcgatt tcaggtacta cttcattttg atctttgatt ttccctaaat    1080
cgaaatccat cggttgattc tctgttgact acgtcttatt tctaaatcct tagatctaga    1140
ttcgattctt gtaagaatta gcctcgtgaa tcaatatgat aacgtgtttc attgttttta    1200
ggt                                                                   1203

<210> SEQ ID NO 20
<211> LENGTH: 826
<212> TYPE: DNA
<213> ORGANISM: Arabidopsis thaliana

<400> SEQUENCE: 20
actaaaaccc tacatttcct ttttgcgttt ttatggccgt aacttccggt tcacggtgtt       60
actttatcgt actaaatata agttttaacg tctgatatat ataaatcgtg tcaaacaaga     120
```

```
aaatatatca ttaataaaca gagattttaa tttgtaacgt gtcaatctga tataactgtc    180
cgtagatttt ctttatttac taatttattt gtgtatctcg tgtcttaaat atccgtagat    240
tctcgtttac ttgcttagtt tgacatattt catttcttac tcggtactcg ccttttaatc    300
gatcgtgttt aatatcttct ataagaaaac attacttcca agtgtatact gtcttcatca    360
tccagcttca tacggttgtg ggataaaatt tgattactag ggaaagctta catgtactaa    420
cttggggtca taagtcataa cactagtact accaagtagg ttatctagtt attaccaccg    480
tccgtgacca tgtatccatc caatccatga aaaagtcaaa acatttcat ttggatgtat     540 tgggctttga gatttacgtt tcattaaaaa tgaagcccaa aagcccatta ttatccaatt    600
gactagagtg gtctctgatc ccaaatcttt aacttggatc ttaacacaga gaagaagcac    660
aatcggaaga aaggagaaga cgaagcaggt atgaatttcc cccttttcg attcattgct     720 ctctctctct cctagggttt gctcgatttg atccggttta tacaaatttg ggtactctat    780
tgaacatttg gttgatgatt tgatttgaat ttgtgattgg gcaggt                   826

<210> SEQ ID NO 21
<211> LENGTH: 685
<212> TYPE: DNA
<213> ORGANISM: Arabidopsis thaliana

<400> SEQUENCE: 21
actaaaaccc tacatttcct ttttgcgttt ttatggccgt aacttccggt tcacggtgtt    60
actttatcgt actaaatata agttttaacg tctgatatat ataaatcgtg tcaaacaaga    120
aaatatatca ttaataaaca gagattttaa tttgtaacgt gtcaatctga tataactgtc    180
cgtagatttt ctttatttac taatttattt gtgtatctcg tgtcttaaat atccgtagat    240
tctcgtttac ttgcttagtt tgacatattt catttcttac tcggtactcg ccttttaatc    300
gatcgtgttt aatatcttct ataagaaaac attacttcca agtgtatact gtcttcatca    360
tccagcttca tacggttgtg ggataaaatt tgattactag ggaaagctta catgtactaa    420
cttggggtca taagtcataa cactagtact accaagtagg ttatctagtt attaccaccg    480
tccgtgacca tgtatccatc caatccatga aaaagtcaaa acatttcat ttggatgtat     540 tgggctttga gatttacgtt tcattaaaaa tgaagcccaa aagcccatta ttatccaatt    600
gactagagtg gtctctgatc ccaaatcttt aacttggatc ttaacacaga gaagaagcac    660
aatcggaaga aaggagaaga cgaag                                          685

<210> SEQ ID NO 22
<211> LENGTH: 185
<212> TYPE: DNA
<213> ORGANISM: Arabidopsis thaliana

<400> SEQUENCE: 22
tttttatttt cttttttta taactttggg tgagcttaat ggcccaatag actgctctgt     60
gaaagcccaa aactaagccc aaataaaata agggtagtaa cgtaattgag ctaagaaacc    120
ctagaggtct ccttcgccta caaaatcccc attttgataa tcttcagcag ccgttgcctc    180
aaaag                                                                185

<210> SEQ ID NO 23
<211> LENGTH: 46
<212> TYPE: DNA
<213> ORGANISM: Artificial Sequence
<220> FEATURE:
```

<223> OTHER INFORMATION: Description of Artificial Sequence: Synthetic
      promoter oligonucleotide

<400> SEQUENCE: 23
gcaagaccct tcctctatat aaggaagttc atttcatttg gagagg         46

<210> SEQ ID NO 24
<211> LENGTH: 1202
<212> TYPE: DNA
<213> ORGANISM: Arabidopsis thaliana

<400> SEQUENCE: 24
gttttgtgta tcattcttgt tacattgtta ttaatgaaaa aatattattg gtcattggac    60
tgaacacgag tgttaaatat ggaccaggcc ccaaataaga tccattgata tatgaattaa   120
ataacaagaa taaatcgagt caccaaacca cttgccttt ttaacgagac ttgttcacca   180
acttgataca aaagtcatta tcctatgcaa atcaataatc atacaaaaat atccaataac   240
actaaaaaat taaagaaat ggataatttc acaatatgtt atacgataaa gaagttactt   300
ttccaagaaa ttcactgatt ttataagccc acttgcatta gataaatggc aaaaaaaaac   360
aaaaaggaaa agaaataaag cacgaagaat tctagaaaat acgaaatacg cttcaatgca   420
gtgggaccca cggttcaatt attgccaatt ttcagctcca ccgtatattt aaaaaataaa   480
acgataatgc taaaaaaata taaatcgtaa cgatcgttaa atctcaacgg ctggatctta   540
tgacgaccgt tagaaattgt ggttgtcgac gagtcagtaa taaacggcgt caaagtggtt   600
gcagccggca cacgagtc gtgtttatca actcaaagca caaatacttt tcctcaacct   660
aaaaataagg caattagcca aaaacaactt tgcgtgtaaa caacgctcaa tacacgtgtc   720
attttattat tagctattgc ttcaccgcct tagctttctc gtgacctagt cgtcctcgtc   780
ttttcttctt cttcttctat aaaacaatac ccaaagagct cttcttcttc acaattcaga   840
tttcaatttc tcaaaatctt aaaaacttc tctcaattct ctctaccgtg atcaaggtaa   900
atttctgtgt tccttattct ctcaaaatct tcgattttgt tttcgttcga tcccaattc   960 gtatatgttc tttggtttag attctgttaa tcttagatcg aagacgattt tctgggtttg  1020
atcgttagat atcatcttaa ttctcgatta gggtttcata gatatcatcc gatttgttca  1080
aataatttga gttttgtcga ataattactc ttcgatttgt gatttctatc tagatctggt  1140
gttagtttct agtttgtgcg atcgaatttg tcgattaatc tgagttttc tgattaacag  1200 gt                                                               1202